(12) United States Patent
Cladingboel et al.

(10) Patent No.: US 7,164,017 B2
(45) Date of Patent: Jan. 16, 2007

(54) OXABISPIDINE COMPOUNDS USEFUL IN THE TREATMENT OF CARDIAC ARRHYTHMIAS

(75) Inventors: David Cladingboel, Mountsorrel (GB); John Pavey, Loughborough (GB); Colin Thomson, Loughborough (GB)

(73) Assignee: AstraZeneca AB, Sordertalje (SE)

( * ) Notice: Subject to any disclaimer, the term of this patent is extended or adjusted under 35 U.S.C. 154(b) by 472 days.

(21) Appl. No.: 10/317,195

(22) Filed: Dec. 12, 2002

(65) Prior Publication Data

US 2003/0153564 A1 Aug. 14, 2003

Related U.S. Application Data

(62) Division of application No. 09/688,251, filed on Oct. 16, 2000, now Pat. No. 6,559,143.

(30) Foreign Application Priority Data

Oct. 18, 1999 (SE) .................................... 9903759

(51) Int. Cl.
*C07D 265/36* (2006.01)
*C07D 498/02* (2006.01)
(52) U.S. Cl. ..................................... 544/105
(58) Field of Classification Search ................ 540/469, 540/472; 544/74, 80
See application file for complete search history.

(56) References Cited

U.S. PATENT DOCUMENTS

| | | | |
|---|---|---|---|
| 3,196,154 A | 7/1965 | Steck | |
| 3,503,939 A | 3/1970 | Williams | |
| 4,459,301 A | 7/1984 | Binnig et al. | |
| 4,556,662 A | 12/1985 | Binnig et al. | |
| 5,140,033 A | 8/1992 | Schriewer et al. | |
| 5,468,858 A | 11/1995 | Berlin et al. | |
| 5,831,099 A | 11/1998 | Dave et al. | |
| 6,291,475 B1 * | 9/2001 | Alstermark et al. | 514/300 |
| 6,492,382 B1 * | 12/2002 | Bjore et al. | 514/300 |
| 6,559,162 B1 * | 5/2003 | Bjorsne et al. | 514/299 |
| 6,887,881 B1 * | 5/2005 | Bjor et al. | 514/278 |

FOREIGN PATENT DOCUMENTS

| | | |
|---|---|---|
| EP | 0 125 826 | 11/1984 |
| EP | 0 308 843 | 9/1989 |
| GB | 1 256 850 | 12/1971 |
| JP | 62-84070 | 4/1987 |
| WO | WO 91/07405 | 5/1991 |
| WO | 99/31100 | 6/1999 |
| WO | WO 00/61569 | 4/2000 |
| WO | WO 01/28992 A2 | 4/2001 |
| WO | WO 01/28992 A3 | 4/2001 |

OTHER PUBLICATIONS

Paudler, W.W. et al., "3,7-Disubstituted Octahydro-1,5-diazocines . . . " J. Org. Chem., Aug. 1967, vol. 32, pp. 2425-2430.*
Mueller, Claus D., et al; "Eljárás biszpidin-származékok elöállítására"; *Hungarian Patent Office*; Application No. P8200945 (Mar. 26, 1982), Publication No. 29934 (Feb. 28, 1984) (abstract).
Nemec et al.; "Pharmacotherapy of atrial fibrillation"; Expert Opinion on Pharmacotherapy; Ashley Publications Ltd., ISSN 1465-6566; 1999.
"Special Report; Preliminary Report: Effect of encainide and flecainide . . . ," New England Journal of Medicine, vol. 321, No. 6, pp. 406-412 (1989).
Zh. Obshch. Khim., vol. 33, No. 9, pp. 3110-3112 (1963).
J. Med. Chem., vol. 39, p. 2559 (1996).
Pharmacol. Res., vol. 24, p. 149 (1991).
Circulation 90, p. 2032 (1994).
Anal. Sci., vol. 9, p. 429 (1993).
Stetter et al, "Synthese des 1,3-Diaza-6-oxa-adamantans," Chem. Ber. vol. 96, No. 11, pp. 2827-2830 (1963).
Villa et al, "3,8-Diazabicyclo . . . ," Eur. J. Med. Chem., vol. 36, pp. 495-506 (2001).
Stetter et al, "Syntheses des 1,3-Diaza-6-oxa-adamantans," Chem. Ber. vol. 96, No. 11, pp. 2829-2830 (1963).
Sorokin et al, "Reaction ob Bis(2,3-epoxypropyl)butylamine . . . ," J. Org. Chem. USSR (Eng. transl.) 2150-2153 (1971).
Chapman, et al, Difluoramination of Heterocyclic Ketones: Control . . . , J. Org. Chem. vol. 63, pp. 1566-1570 (1998).
Chapman et al, "Nitrolysis of a Highly Deactivated Amide . . . ," J. Org. Chem., vol. 64, pp. 960-965 (1999).
Dave et al, "Facile Preparation of 3,7-Diazabicyclo[3.3.0] octane . . . , " J. Org. Chem., vol. 61, pp. 8897-8903 (1996).
Nelson et al, "The Synthesis of 2,5- and 2,6- . . . " J. Org. Chem. vol. 36, No. 22, pp. 3361-3365 (1971).
Paulder et al, "3,7-Disubstituted Octahydro . . . ," pp. 2425-2431 (1967).
Paulder et al, "1,5-Bis-p-toluenesfonyl) . . . , " pp. 277-281 (1966).

(Continued)

*Primary Examiner*—Bruck Kifle
(74) *Attorney, Agent, or Firm*—Nixon & Vanderhye

(57) ABSTRACT

There is provided compounds of formula I,

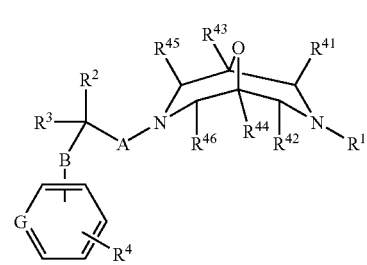

wherein $R^1$, $R^2$, $R^3$, $R^4$, $R^{41}$ to $R^{46}$, A, B and G have meanings given in the description, which are useful in the prophylaxis and in the treatment of arrhythmias, in particular atrial and ventricular arrhythmias.

1 Claim, No Drawings

OTHER PUBLICATIONS

Abstract No. 1987:637909.
Abstract No. 1987-146842.
Lange et al, "Facile Conversion of Primary . . . ," Synthetic Communications, vol. 20, No. 10, pp. 1473-1479 (1990).
Steck, et al; *J. Org. Chem.*; 28(9)2233-8 (1963).
Chem. Abs. vol. 56, 1962, No. 154911, Nikitskya et al,Zh. Obshich, 31, 3202-5 (1961).
Chem. Abs. vol. 59, 1963, No. 7474h, Cignarelli et al; Gazz. Chim. Ital, 93(4), 320-8 (1963).
Chem. Abs. vol. 59, 1963, No. 2822c, Cignarelli et al, Chim. Ital, 93, 226-37 (1963).
Chem. Abs. vol. 46, 1952, No. 992f, Zu-Yoong Kyi et al, J. Chem. Soc. (1963) 1706-8.
Chem. Abs. vol. 48, 1954, No. 2068d, Roderick A. Barnes et al, J.Am. Chem. Soc. 75, 975-7 (1953).
Chem. Abs. vol. 55, 1961, No. 19010d, M.V. Rubtsov et al, J. Med. Pharm. Chem. 3, 441-60 (1961).
Paritosh, R. Dave et al; J. Org. Chem. 1996, 61, 8897-8903.

* cited by examiner

OXABISPIDINE COMPOUNDS USEFUL IN THE TREATMENT OF CARDIAC ARRHYTHMIAS

This application is a Divisional of application Ser. No. 09/688,251, filed Oct. 16, 2000, the entire content of which is hereby incorporated by reference in this application.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in New England Journal of Medicine, 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 655 228 and U.S. Pat. Nos. 3,962,449, 4,556,662, 4,550,112, 4,459,301 and 5,468,858, as well as journal articles including inter alia J. Med. Chem. 39, 2559, (1996), Pharmacol. Res., 24, 149 (1991), Circulation, 90, 2032 (1994) and Anal. Sci. 9, 429, (1993). Oxabispidine compounds are neither disclosed nor suggested in any of these documents.

Certain oxabispidine compounds are disclosed as chemical curiosities in *Chem. Ber.*, 96, 2872 (1963). That these compounds may be used in the treatment of arrhythmias is neither mentioned nor suggested.

We have surprisingly found that a novel group of oxabispidine-based compounds exhibit electrophysiological activity, preferably class III electrophysiological activity, and are therefore expected to be useful in the treatment of cardiac arrhythmias.

DISCLOSURE OF THE INVENTION

According to the invention there is provided compounds of formula I,

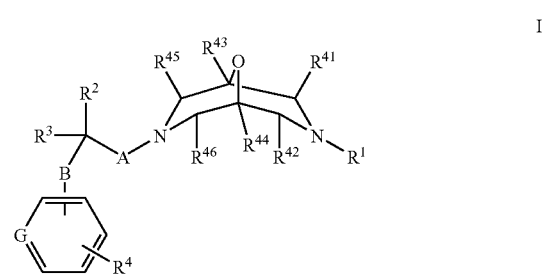

wherein $R^1$ represents $C_{1-12}$ alkyl (which alkyl group is optionally substituted and/or terminated by one or more groups selected from halo, cyano, nitro, aryl, $Het^1$, $-C(O)R^{5a}$, $-OR^{5b}$, $-N(R^6)R^{5c}$, $-C(O)XR^7$, $-C(O)N(R^8)R^{5d}$, and $-S(O)_2R^9$), or $R^1$ represents $-C(O)XR^7$, $-C(O)N(R^8)R^{5d}$ or $-S(O)_2R^9$;

$R^{5a}$ to $R^{5d}$ independently represent, at each occurrence, H, $C_{1-6}$ alkyl (which latter group is optionally substituted and/or terminated by one or more substituents selected from $-OH$, halo, cyano, nitro, aryl and $Het^2$), aryl or $Het^3$, or $R^{5d}$, together with $R^8$, represents $C_{3-6}$ alkylene (which alkylene group is optionally interrupted by an O atom and/or is optionally substituted by one or more $C_{1-3}$ alkyl groups);

$R^6$ represents H, $C_{1-6}$ alkyl (optionally substituted and/or terminated by one or more substituents selected from $-OH$, halo, cyano, nitro and aryl), aryl, $-C(O)R^{10a}$, $-C(O)OR^{10b}$ or $-C(O)N(H)R^{10c}$;

$R^{10a}$, $R^{10b}$ and $R^{10c}$ independently represent $C_{1-6}$ alkyl (optionally substituted and/or terminated by one or more substituents selected from $-OH$, halo, cyano, nitro and aryl), aryl, or $R^{10a}$ represents H;

$R^7$ represents $C_{1-12}$ alkyl (optionally substituted and/or terminated by one or more substituents selected from $-OH$, halo, cyano, nitro, aryl, $C_{1-6}$ alkoxy and $Het^4$);

$R^8$ represents H, $C_{1-12}$ alkyl, $C_{1-6}$ alkoxy (which latter two groups are optionally substituted and/or terminated by one or more substituents selected from $-OH$, halo, cyano, nitro, $C_{1-4}$ alkyl and $C_{1-4}$ alkoxy), $-D$-aryl, $-D$-aryloxy, $-D-Het^5$, $-D-N(H)C(O)R^{11a}$, $-D-S(O)_2R^{12a}$, $-D-C(O)R^{11b}$, $-D-C(O)OR^{12b}$, $-D-C(O)N(R^{11c})R^{11d}$, or $R^8$, together with $R^{5d}$, represents $C_{3-6}$ alkylene (which alkylene group is optionally interrupted by an O atom and/or is optionally substituted by one or more $C_{1-3}$ alkyl groups);

$R^{11a}$ to $R^{11d}$ independently represent H, $C_{1-6}$ alkyl (optionally substituted and/or terminated by one or more substituents selected from $-OH$, halo, cyano, nitro and aryl), aryl, or $R^{11c}$ and $R^{11d}$ together represent $C_{3-6}$ alkylene;

$R^9$, $R^{12a}$ and $R^{12b}$ independently represent $C_{1-6}$ alkyl (optionally substituted and/or terminated by one or more substituents selected from $-OH$, halo, cyano, nitro and aryl) or aryl;

D represents a direct bond or $C_{1-6}$ alkylene;

X represents O or S;

$R^2$ represents H, halo, $C_{1-6}$ alkyl, —$OR^{13}$, —E—$N(R^{14})R^{15}$ or, together with $R^3$, represents =O;

$R^3$ represents H, $C_{1-6}$ alkyl or, together with $R^2$, represents =O;

$R^{13}$ represents H, $C_{1-6}$ alkyl, —E-aryl, —E—$Het^6$, —C(O)$R^{16a}$, —C(O)$OR^{16b}$ or —C(O)N($R^{17a}$)$R^{17b}$;

$R^{14}$ represents H, $C_{1-6}$ alkyl, —E-aryl, —E—$Het^6$, —C(O)$R^{16a}$, —C(O)$OR^{16b}$, —S(O)$_2R^{16c}$, —[C(O)]$^p$N($R^{17a}$)$R^{17b}$ or —C(NH)NH$_2$;

$R^{15}$ represents H, $C_{1-6}$ alkyl, —E-aryl or —C(O)$R^{16d}$;

$R^{16a}$ to $R^{16d}$ independently represent, at each occurrence when used herein, $C_{1-6}$ alkyl (optionally substituted and/or terminated by one or more substituents selected from halo, aryl and $Het^7$), aryl, $Het^8$, or $R^{16a}$ and $R^{16d}$ independently represent H;

$R^{17a}$ and $R^{17b}$ independently represent, at each occurrence when used herein, H or $C_{1-6}$ alkyl (optionally substituted and/or terminated by one or more substituents selected from halo, aryl and $Het^9$), aryl, $Het^{10}$, or together represent $C_{3-6}$ alkylene, optionally interrupted by an O atom;

E represents, at each occurrence when used herein, a direct bond or $C_{1-4}$ alkylene;

p represents 1 or 2;

$Het^1$ to $Het^{10}$ independently represent five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, —N($R^{18a}$)$R^{18b}$, —C(O)$R^{18c}$, —C(O)$OR^{18d}$, —C(O)N($R^{18e}$)$R^{18f}$, —N($R^{18g}$)C(O)$R^{18h}$ and —N($R^{18i}$)S(O)$_2R^{18j}$;

$R^{18a}$ to $R^{18j}$ independently represent $C_{1-6}$ alkyl, aryl or $R^{18a}$ to $R^{18i}$ independently represent H;

A represents a direct bond, —J—, —J—N($R^{19}$)— or —J—O— (in which latter two groups, N($R^{19}$) or O— is attached to the carbon atom bearing $R^2$ and $R^3$);

B represents —Z—, —Z—N($R^{20}$)—, —N($R^{20}$)—Z—, —Z—S(O)$_n$—, —Z—O— (in which latter two groups, Z is attached to the carbon atom bearing $R^2$ and $R^3$), —N($R^{20}$)C(O)O—Z—, (in which latter group, —N($R^{20}$) is attached to the carbon atom bearing $R^2$ and $R^3$) or —C(O)N($R^{20}$)— (in which latter group, —C(O) is attached to the carbon atom bearing $R^2$ and $R^3$);

J represents $C_{1-6}$ alkylene optionally substituted by one or more substituents selected from —OH, halo and amino;

Z represents a direct bond or $C_{1-4}$ alkylene;

n represents 0, 1 or 2;

$R^{19}$ and $R^{20}$ independently represent H or $C_{1-6}$ alkyl;

G represents CH or N;

$R^4$ represents one or more optional substituents selected from —OH, cyano, halo, nitro, $C_{1-6}$ alkyl (optionally terminated by —N(H)C(O)$OR^{21a}$), $C_{1-6}$ alkoxy, —N($R^{22a}$)$R^{22b}$, —C(O)$R^{22c}$, —C(O)$OR^{22d}$, —C(O)N($R^{22e}$)$R^{22f}$, —N($R^{22g}$)C(O)$R^{22h}$, —N($R^{22i}$)C(O)N($R^{22j}$)$R^{22k}$, —N($R^{22m}$)S(O)$_2R^{21b}$, —S(O)$_2R^{21c}$, and/or —OS(O)$_2R^{21d}$;

$R^{21a}$ to $R^{21d}$ independently represent $C_{1-6}$ alkyl;

$R^{22a}$ and $R^{22b}$ independently represent H, $C_{1-6}$ alkyl or together represent $C_{3-6}$ alkylene, resulting in a four- to seven-membered nitrogen-containing ring;

$R^{22c}$ to $R^{22m}$ independently represent H or $C_{1-6}$ alkyl; and $R^{41}$ to $R^{46}$ independently represent H or $C_{1-3}$ alkyl;

wherein each aryl and aryloxy group, unless otherwise specified, is optionally substituted;

provided that (a) the compound is not: 3,7-dibenzoyl-9-oxa-3,7-diazabicyclo[3.3.1]nonane;

(b) when A represents —J—N($R^{19}$)— or —J—O—, then:
 (i) J does not represent $C_1$ alkylene; and
 (ii) B does not represent —N($R^{20}$)—, —N($R^{20}$)—Z— (in which latter group N($R^{20}$) is attached to the carbon atom bearing $R^2$ and $R^3$), —S(O)$_n$—, —O— or —N($R^{20}$)C(O)O—Z— when $R^2$ and $R^3$ do not together represent =O; and (c) when $R^2$ represents —$OR^{13}$ or —N($R^{14}$)($R^{15}$), then:
 (i) A does not represent —J—N($R^{19}$)— or —J—O—; and
 (ii) B does not represent —N($R^{20}$)—, —N($R^{20}$)—Z— (in which latter group N($R^{20}$) is attached to the carbon atom bearing $R^2$ and $R^3$), —S(O)$_n$—, —O— or —N($R^{20}$)C(O)O—Z—;

or a pharmaceutically acceptable derivative thereof;

which compounds are referred to hereinafter as "the compounds of the invention".

Unless otherwise specified, alkyl groups and alkoxy groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, halo, cyano, nitro, $C_{1-6}$ alkyl, $C_{1-6}$ alkoxy, —N($R^{22a}$)$R^{22b}$, —C(O)$R^{22c}$, —C(O)$OR^{22d}$, —C(O)N($R^{22e}$)$R^{22f}$, —N($R^{22g}$)C(O)$R^{22h}$, —N($R^{22m}$)S(O)$_2R^{21b}$, —S(O)$_2R^{21c}$, and/or —OS(O)$_2R^{21d}$ (wherein $R^{21b}$ to $R^{21d}$ and $R^{22a}$ to $R^{22m}$ are as hereinbefore defined). When substituted, aryl and aryloxy groups are preferably substituted by between one and three substitutents.

The term "halo", when used herein, includes fluoro, chloro, bromo and iodo.

Het ($Het^1$, $Het^2$, $Het^3$, $Het^4$, $Het^5$, $Het^6$, $Het^7$, $Het^8$, $Het^9$ and $Het^{10}$) groups that may be mentioned include those containing 1 to 4 heteroatoms (selected from the group oxygen, nitrogen and/or sulfur) and in which the total number of atoms in the ring system are between five and twelve. Het ($Het^1$, $Het^2$, $Het^3$, $Het^4$, $Het^5$, $Het^6$, $Het^7$, $Het^8$, $Het^9$ and $Het^{10}$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzimidazolyl, benzomorpholinyl, benzoxazinonyl, benzothiophenyl, chromanyl, cinnolinyl, dioxanyl, furanyl, imidazolyl, imidazo[1,2-α]pyridinyl, indolyl, isoquinolinyl, isoxazolyl, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, tetrahydropyranyl, tetrahydrofuranyl, thiazolyl, thienyl, thiochromanyl, triazolyl and the like. Values of $Het^1$ that may be mentioned include pyridinyl, benzodioxanyl, imidazolyl, imidazo[1,2-α]pyridinyl, piperazinyl, pyrazolyl, pyrrolyl, pyrrolidinyl, tetrahydropyranyl and thiazolyl. Values of $Het^3$ that may be mentioned include benzodioxanyl and benzomorpholinyl. Values of $Het^4$ that may be mentioned include piperazinyl. Substituents on Het ($Het^1$, $Het^2$, $Het^3$, $Het^4$, $Het^5$, $Het^6$, $Het^7$, $Het^8$, $Het^9$ and $Het^{10}$) groups may, where appropriate, be located on any atom in the ring system including a heteroatom. The point of attachment of Het ($Het^1$, $Het^2$, $Het^3$, $Het^4$, $Het^5$, $Het^6$, $Het^7$, $Het^8$, $Het^9$ and $Het^{10}$) groups may be via any atom in the ring system including (where appropriate) a heteroatom, or an atom on any fused carbocyclic ring that may be present as part of the ring system. Het ($Het^1$, $Het^2$, $Het^3$, $Het^4$, $Het^5$, $Het^6$, $Het^7$, $Het^8$, $Het^9$ and $Het^{10}$) groups may also be in the N- or S-oxidised form.

Pharmaceutically acceptable derivatives include salts and solvates. Salts which may be mentioned include acid addition salts. Specific salts that may be mentioned include arylsulfonate salts, such as toluenesulfonate and, especially, benzenesulfonate salts. Solvates that may be mentioned include hydrates, such as monohydrates of the compounds of the invention.

Pharmaceutically acceptable derivatives also include, at the oxabispidine or (when G represents N) pyridyl nitrogens, $C_{1-4}$ alkyl quaternary ammonium salts and N-oxides, provided that when a N-oxide is present:
(a) no $Het$ ($Het^1$, $Het^2$, $Het^3$, $Het^4$, $Het^5$, $Het^6$, $Het^7$, $Het^8$, $Het^9$ and $Het^{10}$) group contains an unoxidised S-atom; and/or
(b) n does not represent 0 when B represents —Z—S(O)$_n$—.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Abbreviations are listed at the end of this specification.

Compounds of formula I that may be mentioned include those in which, when $R^2$ and $R^3$ together represent =O, then A and B do not simultaneously represent direct bonds.

Preferred compounds of the invention include those in which:
$R^1$ represents $C_{1-8}$ alkyl (which alkyl group is optionally substituted and/or terminated by one or more groups selected from halo, optionally substituted aryl, optionally substituted $Het^1$, —C(O)$R^{5a}$, —OR$^{5b}$, —N(R$^6$)R$^{5c}$, —C(O)N(R$^8$)R$^{5d}$, and —S(O)$_2$R$^9$), or $R^1$ represents —C(O)OR$^7$, —C(O)N(R$^8$)R$^{5d}$ or —S(O)$_2$R$^9$;

$R^{5a}$ to $R^{5d}$ independently represent, at each occurrence, H, $C_{1-6}$ alkyl (which latter group is optionally substituted and/or terminated by one or more substituents selected from halo, cyano, nitro and aryl), aryl (which latter group is optionally substituted by one or more substituents selected from halo, hydroxy, cyano, nitro, N(R$^{22a}$)R$^{22b}$ (in which latter group R$^{22a}$ and R$^{22b}$ together represent $C_{3-6}$ alkylene), $C_{1-4}$ alkyl and $C_{1-4}$ alkoxy (which latter two groups are optionally substituted by one or more halo atoms)), Het$^3$, or R$^{5d}$, together with R$^8$, represents $C_{4-5}$ alkylene (which alkylene group is optionally interrupted by an O atom);

$R^6$ represents H, $C_{1-6}$ alkyl, aryl (which latter group is optionally substituted by one or more substituents selected from halo, cyano, nitro, $C_{1-4}$ alkyl and $C_{1-4}$ alkoxy), —C(O)R$^{10a}$, —C(O)OR$^{10b}$ or C(O)N(H)R$^{10c}$;

$R^{10a}$ and $R^{10b}$ independently represent $C_{1-4}$ alkyl (optionally substituted by one or more substituents selected from halo and aryl) or aryl (which latter group is optionally substituted by or more substituents selected from halo, cyano, nitro. $C_{1-4}$ alkyl and $C_{1-4}$ alkoxy);

$R^{10c}$ represents $C_{1-4}$ alkyl;

$R^7$ represents $C_{1-6}$ alkyl optionally substituted and/or terminated by one or more substituents selected from halo, aryl, $C_{1-4}$ alkoxy and Het$^4$;

$R^8$ represents H, $C_{1-6}$ alkyl (which latter group is optionally substituted and/or terminated by one or more substituents selected from halo, cyano and nitro), —D-aryl, —D-aryloxy, —D—Het$^5$, —D—N(H)C(O)R$^{11a}$, —D—C(O)R$^{11b}$, or R$^8$, together with R$^{5d}$, represents $C_{4-5}$ alkylene (which alkylene group is optionally interrupted by an O atom);

$R^{11a}$ and $R^{11b}$ independently represent $C_{1-4}$ alkyl (optionally substituted and/or terminated by one or more substituents selected from halo, cyano, nitro and aryl) or aryl;

D represents a direct bond or $C_{1-3}$ alkylene;

$R^9$ represents $C_{1-6}$ alkyl (optionally substituted by one or more halo groups) or aryl (which latter group is optionally substituted by one or more substituents selected from $C_{1-4}$ alkyl, $C_{1-4}$ alkoxy, halo, nitro and cyano);

$R^2$ represents H, halo, $C_{1-3}$ alkyl, —OR$^{13}$, —N(H)R$^{14}$ or, together with R$^3$, represents =O;

$R^3$ represents H, $C_{1-3}$ alkyl or, together with R$^2$, represents =O;

$R^{13}$ represents H, $C_{1-4}$ alkyl, —E-aryl (optionally substituted by one or more substituents selected from cyano, halo, nitro, $C_{1-4}$ alkyl and $C_{1-4}$ alkoxy), or —E—Het$^6$;

$R^{14}$ represents H, $C_{1-6}$ alkyl, —E-aryl (which aryl group is optionally substituted by one or more substituents selected from cyano, halo, nitro, $C_{1-4}$ alkyl and $C_{1-4}$ alkoxy), —C(O)R$^{16a}$, —C(O)OR$^{16b}$, —S(O)$_2$R$^{16c}$, —C(O)N(R$^{17a}$)R$^{17b}$ or —C(NH)NH$_2$;

$R^{16a}$ to $R^{16c}$ independently represent $C_{1-6}$ alkyl, or R$^{16a}$ represents H;

$R^{17a}$ and $R^{17b}$ independently represent H or $C_{1-4}$ alkyl;

E represents a direct bond or $C_{1-2}$ alkylene;

Het$^1$ to Het$^6$ are optionally substituted by one or more substituents selected from oxo, halo, cyano, nitro, $C_{1-4}$ alkyl, $C_{1-4}$ alkoxy, —N(R$^{18a}$)R$^{18b}$, —C(O)R$^{18c}$ or —C(O)OR$^{18d}$;

$R^{18a}$ to $R^{18d}$ independently represent H, $C_{1-4}$ alkyl or aryl;

A represents —J—, —J—N(R$^{19}$)— or —J—O—;

B represents —Z—, —Z—N($R^{20}$)—, —N($R^{20}$)—Z—, —Z—S(O)$_n$—, —Z—O— or —N($R^{20}$)C(O)O—Z—;

J represents $C_{1-4}$ alkylene;

Z represents a direct bond or $C_{1-3}$ alkylene;

n represents 0 or 2;

$R^{19}$ and $R^{20}$ independently represent H or $C_{1-4}$ alkyl;

when G represents N, G is in the ortho- or, in particular, the para-position relative to the point of attachment of B;

when G represents N, $R^4$ is absent or represents a single cyano group;

$R^4$ is selected from —OH, cyano, halo, nitro, $C_{1-6}$ alkyl $C_{1-6}$ alkoxy, —C(O)N($R^{22e}$)$R^{22f}$, —N($R^{22g}$)C(O)$R^{22h}$, and/or —N($R^{22m}$)S(O)$_2$—$C_{1-4}$ alkyl;

$R^{22e}$ to $R^{22m}$ independently represent H or $C_{1-4}$ alkyl;

$R^{41}$ to $R^{46}$ independently represent H.

More preferred compounds of the invention include those in which:

$R^1$ represents straight-chain or branched-chain or part cyclic/acyclic $C_{1-6}$ alkyl optionally interrupted by oxygen and/or optionally substituted and/or terminated by: (i) one or more halo or —OR$^{5b}$ groups; and/or (ii) one group selected from phenyl (which latter group is optionally substituted by one or more substituents selected from halo, cyano and $C_{1-4}$ alkoxy (which latter group is optionally substituted by one or more halo atoms)), Het$^1$, —C(O)R$^{5a}$, —N(H)R$^6$, —C(O)N(R$^8$)R$^{5d}$, and —S(O)$_2$—$C_{1-4}$ alkyl, or $R^1$ represents —C(O)OR$^7$, —C(O)N(R$^8$)R$^{5d}$ or —S(O)$_2$—$C_{1-5}$ alkyl;

Het$^1$ represents a four- (e.g. five-) to ten-membered heterocyclic group containing one or two heteroatoms selected from oxygen, nitrogen and/or sulfur, which group is optionally substituted by one or more substituents selected from $C_{1-2}$ alkyl and —C(O)—$C_{1-4}$ alkyl;

$R^{5a}$, $R^{5b}$ and $R^{5d}$ independently represent H, $C_{1-5}$ alkyl, phenyl (which latter group is optionally substituted by one or more substituents selected from halo, hydroxy, cyano, pyrrolidinyl, $C_{1-4}$ alkyl and $C_{1-5}$ alkoxy (which latter group is optionally substituted by one or more halo atoms)) or Het$^3$;

Het$^3$ represents a five- to ten-membered heterocyclic group containing one or two heteroatoms selected from oxygen and nitrogen, which group is optionally substituted by one or more substituents selected from oxo, $C_{1-2}$ alkyl and —C(O)—$C_{1-4}$ alkyl;

$R^6$ represents H, $C_{1-4}$ alkyl, phenyl (which latter group is optionally substituted by one or more cyano groups) or —C(O)O—$C_{1-5}$ alkyl;

$R^7$ represents $C_{1-5}$ alkyl optionally substituted or terminated by Het$^4$;

Het$^4$ represents a five- to ten-membered heterocyclic group containing one or two heteroatoms selected from oxygen and nitrogen, which group is optionally substituted by one or more substituents selected from $C_{1-2}$ alkyl and —C(O)—$C_{1-4}$ alkyl;

$R^8$ represents H or $C_{1-4}$ alkyl;

$R^2$ represents H, —OR$^{13}$ or —N(H)R$^{14}$;

$R^3$ represents H;

$R^{13}$ represents H or phenyl (optionally substituted by one or more substituents selected from cyano and $C_{1-2}$ alkoxy);

$R^{14}$ represents H, phenyl (optionally substituted by one or more cyano groups) or —C(O)O—$C_{1-5}$ alkyl;

A represents $C_{1-3}$ alkylene;

B represents —Z—, —Z—N(H)—, —Z—S(O)$_2$—, or —Z—O— (in which latter three groups, Z is attached to the carbon atom bearing $R^2$ and $R^3$);

Z represents a direct bond or $C_{1-2}$ alkylene;

G represents CH;

$R^4$ represents one or two cyano groups in the ortho- and/or, in particular, the para-position relative to B.

Particularly preferred compounds of the invention include those in which:

$R^1$ represents straight-chain or branched-chain or part cyclic/acyclic $C_{1-6}$ alkyl optionally interrupted by oxygen and/or optionally substituted and/or terminated by: (i) one or more halo or —OR$^{5b}$ groups; and/or (ii) one group selected from phenyl (which latter group is optionally substituted by one or more substituents selected from halo, cyano and $C_{1-4}$ alkoxy (which latter group is optionally substituted by one or more halo atoms)), Het$^1$, —C(O)R$^{5a}$, —N(H)R$^6$, —C(O)N(R$^8$)R$^{5d}$, and —S(O)$_2$—$C_{1-4}$ alkyl.

Especially preferred compounds of the invention include those in which:

$R^1$ represents straight- or branched-chain $C_{1-4}$ alkyl (e.g. $C_{1-3}$ alkyl) terminated by —C(O)R$^{5a}$ or —N(H)C(O)OR$^{10b}$;

$R^{5a}$ and $R^{10b}$ independently represent straight- or branched-chain $C_{2-6}$ alkyl (e.g. $C_{3-5}$ alkyl, such butyl (e.g. t-butyl));

$R^2$ represents H or OH;

A represents $C_{1-2}$ alkylene;

B represents —Z—, —Z—N(H)— or —Z—O— (in which latter two groups, Z is attached to the carbon atom bearing $R^2$ and $R^3$, and represents $C_{1-2}$ alkylene);

$R^4$ is a single cyano group in the para-position relative to B.

Preferred compounds of the invention include the compounds of the Examples disclosed hereinafter.

Preferred compounds of the invention also include those in which:

$R^6$ does not represent —C(O)N(H)R$^{10c}$;

$R^{22a}$ and $R^{22b}$ do not together represent $C_{3-6}$ alkylene.

Preferred compounds of the invention also include those which are not:

tert-butyl 7-benzyl-9-oxa-3,7-diazabicyclo[3.3.1]nonane-3-carboxylate; or ethyl 7-[(2S)-3-(4-cyanophenoxy)-2-hydroxypropyl]-9-oxa-3,7-diaza-bicyclo[3.3.1]nonane-3-carboxylate;

PREPARATION

According to the invention there is also provided a process for the preparation of compounds of formula I which comprises:

(a) reaction of a compound of formula II,

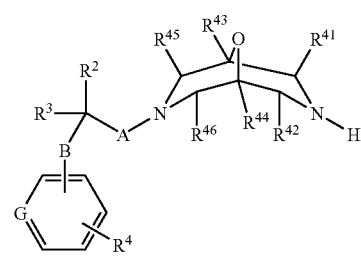

II wherein $R^2$, $R^3$, $R^4$, $R^{41}$ to $R^{46}$, A, B and G are as hereinbefore defined, with a compound of formula III, $R^1$—$L^1$    III wherein $L^1$ represents a leaving group such as halo, alkanesulfonate, perfluoroalkanesulfonate, arenesulfonate, —OC(O)XR$^7$, imidazole or R$^{23}$O— (wherein R$^{23}$ represents, for example, $C_{1-10}$ alkyl or aryl, which groups are optionally substituted by one or more halo or nitro groups) and X, $R^1$ and $R^7$ are as hereinbefore defined, for example at between room and reflux temperature in the presence of a suitable base (e.g. triethylamine, potassium carbonate or a bicarbonate, such as sodium bicarbonate) and an appropriate solvent (e.g. dichloromethane, chloroform, acetonitrile, N,N-dimethylformamide, THF, toluene, water, a lower alkyl alcohol (e.g. ethanol) or mixtures thereof;

(b) for compounds of formula I in which $R^1$ represents —C(O)X$R^7$ or —C(O)N($R^8$)$R^{5d}$, reaction of a compound of formula IV,

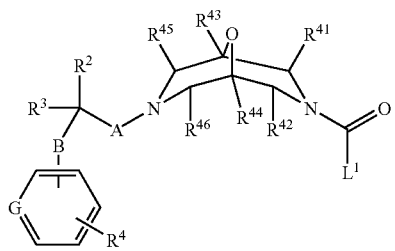

IV wherein $R^2$, $R^3$, $R^4$, $R^{41}$ to $R^{46}$, A, B, G and $L^1$ are as hereinbefore defined, with a compound of formula V, $R^{24}$—H      V wherein $R^{24}$ represents —X$R^7$ or —N($R^8$)$R^{5d}$ and $R^{5d}$, $R^7$, $R^8$ and X are as hereinbefore defined, for example under similar conditions to those described hereinbefore (process step (a));

(c) for compounds in which $R^1$ represents —C(O)N(H)$R^8$, reaction of a compound of formula II, as hereinbefore defined, with a compound of formula VI, $R^8$—N=C=O      VI wherein $R^8$ is as hereinbefore defined, for example at between 0° C. and reflux temperature in the presence of an appropriate organic solvent (e.g. dichloromethane), or via solid phase synthesis under conditions known to those skilled in the art;

(d) reaction of a compound of formula VII,

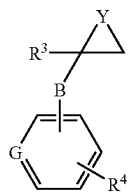

VII wherein $R^1$ and $R^{41}$ to $R^{46}$ are as hereinbefore defined, with a compound of formula VIII,

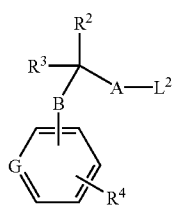

VIII wherein $L^2$ represents a leaving group such as halo, alkanesulfonate (e.g. mesylate), perfluoroalkanesulfonate or arenesulfonate (e.g. 2- or 4-nitrobenzenesulfonate, toluenesulfonate or benzenesulfonate) and $R^2$, $R^3$, $R^4$, A, B and G are as hereinbefore defined, for example at elevated temperature (e.g. between 35° C. and reflux temperature) in the presence of a suitable base (e.g. triethylamine or potassium carbonate) and an appropriate organic solvent (e.g. acetonitrile, dichloromethane, chloroform, dimethylsulfoxide, N,N-dimethylformamide, a lower alkyl alcohol (e.g. ethanol), isopropyl acetate or mixtures thereof);

(e) for compounds of formula I in which A represents $CH_2$ and $R^2$ represents —OH or —N(H)$R^{14}$, reaction of a compound of formula VII, as hereinbefore defined, with a compound of formula IX,

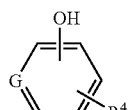

IX wherein Y represents O or N($R^{14}$) and $R^3$, $R^4$, $R^{14}$, B and G are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(f) for compounds of formula I in which B represents —Z—O—, reaction of a compound of formula X,

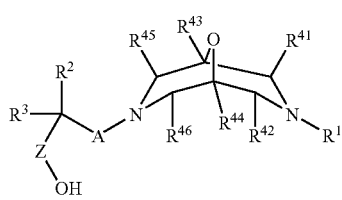

X wherein $R^1$, $R^2$, $R^3$, $R^{41}$ to $R^{46}$, A and Z are as hereinbefore defined, with a compound of formula XI,

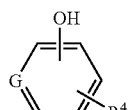

XI wherein $R^4$ and G are as hereinbefore defined, for example under Mitsunobu-type conditions e.g. at between ambient (e.g. 25° C.) and reflux temperature in the presence of a tertiary phosphine (e.g. tributylphosphine or triphenylphosphine), an azodicarboxylate derivative (e.g. diethylazodicarboxylate or 1,1'-(azodicarbonyl)dipiperidine) and an appropriate organic solvent (e.g. dichloromethane or toluene);

(g) for compounds of formula I in which G represents N and B represents —Z—O—, reaction of a compound of formula X, as hereinbefore defined, with a compound of formula XII,

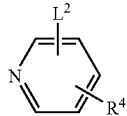
XII wherein $R^4$ and $L^2$ are as hereinbefore defined, for example at between 10° C. and reflux temperature in the presence of a suitable base (e.g. sodium hydride) and an appropriate solvent (e.g. N,N-dimethylformamide);
(h) for compounds of formula I in which $R^2$ represents —$OR^{13}$, in which $R^{13}$ represents $C_{1-6}$ alkyl, —E-aryl or —E—$Het^6$, reaction of a compound of formula I in which $R^2$ represents OH with a compound of formula XIII, $$R^{13a}OH \qquad XIII$$

wherein $R^{13a}$ represents $C_{1-6}$ alkyl, —E-aryl or —E—$Het^6$ and E and $Het^6$ are as hereinbefore defined, for example under Mitsunobu-type conditions (e.g. as described hereinbefore in process step (f));
(i) for compounds of formula I in which $R^2$ represents —$OR^{13}$, in which $R^{13}$ represents $C_{1-6}$ alkyl, —E-aryl or —E—$Het^6$, reaction of a compound of formula XIV,

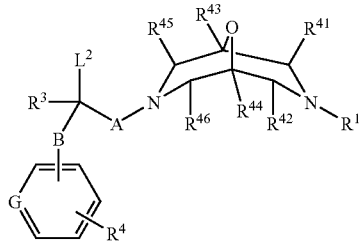
XIV wherein $R^1$, $R^3$, $R^4$, $R^{41}$ to $R^{46}$, A, B, G and $L^2$ are as hereinbefore defined, with a compound of formula XIII, as hereinbefore defined, for example at between ambient (e.g. 25° C.) and reflux temperature, under Williamson-type conditions (i.e. in the presence of an appropriate base (e.g. KOH or NaH) and a suitable organic solvent (e.g. dimethylsulfoxide or N,N-dimethylformamide)) (the skilled person will appreciate that certain compounds of formula XIV (e.g. those in which $L^2$ represents halo) may also be regarded as compounds of formula I as hereinbefore defined);
(j) for compounds of formula I in which $R^2$ represents —E—$NH_2$, reduction of a compound of formula XV,

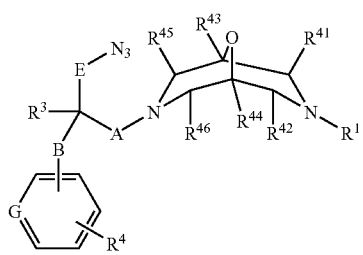
XV wherein $R^1$, $R^3$, $R^4$, $R^{41}$ to $R^{46}$, A, B, E and G are as hereinbefore defined, is for example by hydrogenation at a suitable pressure in the presence of a suitable catalyst (e.g. palladium on carbon) and an appropriate solvent (e.g. a water-ethanol mixture);

(k) for compounds of formula I in which $R^2$ represents —E—$N(R^{14})R^{15}$, wherein $R^{14}$ represents $C_{1-6}$ alkyl, —E-aryl —E—$Het^6$, —$C(O)R^{16a}$, —$C(O)OR^{16b}$, —$S(O)_2R^{16c}$ or —$C(O)N(R^{17a})R^{17b}$, reaction of a compound of formula I in which $R^2$ represents —E—$N(H)R^{15}$ with a compound of formula XVI, $$R^{14a}\text{—}L^1 \qquad XVI$$

wherein $R^{14a}$ represents $C_{1-6}$ alkyl, —E-aryl —E—$Het^6$, —$C(O)R^{16a}$, —$C(O)OR^{16b}$, —$S(O)_2R^{16c}$ or —$C(O)N(R^{17a})R^{17b}$, and $R^{16a}$, $R^{16b}$, $R^{16c}$, $R^{17a}$, $R^{17b}$, $Het^6$, E and $L^1$ are as hereinbefore defined, for example under conditions described hereinbefore (process step (a));
(l) for compounds of formula I in which $R^2$ represents —E—$N(R^{15})C(O)N(H)R^{17a}$, reaction of a compound of formula I in which $R^2$ represents —E—$N(H)R^{15}$ with a compound of formula XVII, $$R^{17a}\text{—}N{=}C{=}O \qquad XVII$$

wherein $R^{17a}$ is as hereinbefore defined, for example under conditions described hereinbefore (process step (c));
(m) for compounds of formula I in which $R^2$ represents —E—$N(H)[C(O)]_2NH_2$, reaction of a compound of formula I in which $R^2$ represents —E—$NH_2$ with oxalic acid diamide, for example at between −10 and 25° C. in the presence of a suitable coupling agent (e.g. 1-(3-dimethylaminopropyl)-3-ethylcarbodiimide), an appropriate activating agent (e.g. 1-hydroxybenzotriazole), a suitable base (e.g. triethylamine) and a reaction-inert solvent (e.g. N,N-dimethylformamide);
(n) for compounds of formula I in which $R^2$ represents —E—$N(H)C(NH)NH_2$, reaction of a compound of formula I in which $R^2$ represents —E—$NH_2$ with a compound of formula XVIII, $$R^{23}O\text{—}C({=}NH)NH_2 \qquad XVIII$$

or an N-protected derivative thereof, wherein $R^{23}$ is as hereinbefore defined, for example at between room and reflux temperature, optionally in the presence of a suitable solvent (e.g. toluene) and/or an appropriate acidic catalyst (e.g. acetic acid at, for example, 10 mol %);
(o) for compounds of formula I in which $R^2$ represents —$OR^{13}$, in which $R^{13}$ represents —$C(O)R^{16a}$, —$C(O)OR^{16b}$ or —$C(O)N(R^{17a})R^{17b}$, reaction of a compound of formula I in which $R^2$ represents —OH with a compound of formula XIX, $$R^{13b}\text{—}L^3 \qquad XIX$$

wherein $R^{13b}$ represents —$C(O)R^{16a}$, —$C(O)OR^{16b}$ or —$C(O)N(R^{17a})R^{17b}$, $L^3$ represents a leaving group such as halo, p-nitrophenoxy, —$OC(O)R^{16a}$, —$OC(O)OR^{16b}$, —OH or imidazole and $R^{16a}$, $R^{16b}$, $R^{17a}$ and $R^{17b}$ are as hereinbefore defined, for example at between −10° C. and reflux temperature in the presence of a suitable base (e.g. triethylamine, pyridine or potassium carbonate), an appropriate organic solvent (e.g. THF, dichloromethane or acetonitrile) and (where appropriate) a suitable coupling agent (e.g. 1-(3-dimethylaminopropyl)-3-ethylcarbodiimide);
(p) for compounds of formula I in which $R^2$ represents H or —OH and $R^3$ represents H, reduction of a compound of formula I in which $R^2$ and $R^3$ together represent =O, in the presence of a suitable reducing agent and under appropriate reaction conditions; for example, for formation of compounds of formula I in which $R^2$ represents OH, reduction may be performed under mild reaction conditions in the presence of e.g. sodium borohydride and an appropriate organic solvent (e.g. THF); for formation of compounds of formula I in which $R^2$ represents OH, wherein the compound is enantiomerically enriched (or is a single enantiomer) at the chiral centre to which $R^2$ is attached, reduction may be performed enzymatically (for example under conditions known to those skilled in the art, such as in the presence of horse liver alcohol dehydrogenase and NADPH) or by hydrogenation in the presence of a suitable solution-phase (homogeneous) catalyst under conditions known to those skilled in the art; and for formation of compounds of formula I in which $R^2$ represents H, reduction may be performed either under Wolff-Kischner conditions known to those skilled in the art or by activating the relevant C=O group using an appropriate agent (such as tosylhydrazine) in the presence of a suitable reducing agent (e.g. sodium borohydride or sodium cyanoborohydride) and an appropriate organic solvent (e.g. a lower (e.g. $C_{1-6}$) alkyl alcohol);

(q) for compounds of formula I in which $R^2$ represents halo, substitution of a corresponding compound of formula I in which $R^2$ represents —OH, using an appropriate halogenating agent (e.g. for compounds in which $R^2$ represents fluoro, reaction with (diethylamino)sulfur trifluoride);

(r) for compounds of formula I in which $R^2$ and $R^3$ represent H, A represents —J— and B represents —N($R^{20}$)—Z— (wherein —N($R^{20}$) is attached to the carbon atom bearing $R^2$ and $R^3$), reaction of a compound of formula XX,

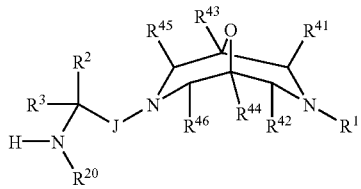

XX wherein $R^1$, $R^2$, $R^3$, $R^{20}$, $R^{41}$ to $R^{46}$ and J are as hereinbefore defined, with a compound of formula XXI,

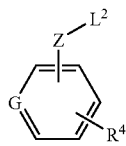

XXI wherein $R^4$, G, Z and $L^2$ are as hereinbefore defined, for example at elevated temperature (e.g. 40° C. to reflux) in the presence of a suitable organic solvent (e.g. acetonitrile);

(s) for compounds of formula I in which A represents $C_2$ alkylene and $R^2$ and $R^3$ together represent =O, reaction of a compound of formula VII, as hereinbefore defined, with a compound of formula XXII,

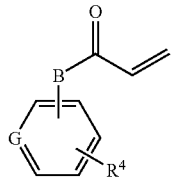

XXII wherein B, G and $R^4$ are as hereinbefore defined, for example at between room and reflux temperature in the presence of a suitable base (e.g. triethylamine, potassium carbonate or tetrabutylammonium hydroxide) and an appropriate organic solvent (e.g. a lower alkyl (e.g. $C_{1-6}$) alcohol);

(t) for compounds of formula I in which $R^1$ represents —C(O)$XR^7$, —C(O)N($R^8$)$R^{5d}$ or —S(O)$_2R^9$, reaction of a compound of formula XXIII,

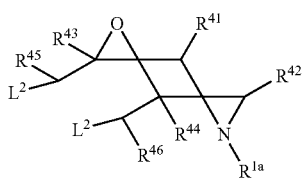

XXIII wherein $R^{1a}$ represents —C(O)$XR^7$, —C(O)N($R^8$)$R^{5d}$ or —S(O)$_2R^9$ and $R^{5d}$, $R^7$, $R^8$, $R^9$, $R^{41}$ to $R^{46}$ and $L^2$ are as herein before defined, with a compound of formula XXIV,

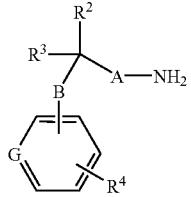

XXIV wherein $R^2$, $R^3$, $R^4$, A, B and G are as hereinbefore defined, for example at between room and reflux temperature in the presence of a suitable base (e.g. sodium hydrogencarbonate or potassium carbonate) and an appropriate organic solvent (e.g. acetonitrile);

(u) for compounds of formula I which are oxabispidine-nitrogen N-oxide derivatives, oxidation of the corresponding oxabispidine nitrogen of a corresponding compound of formula I, in the presence of a suitable oxidising agent (e.g. mCPBA), for example at 0° C. in the presence of a suitable organic solvent (e.g. dichloromethane);

(v) for compounds of formula I which are $C_{1-4}$ alkyl quaternary ammonium salt derivatives, in which the alkyl group is attached to a oxabispidine nitrogen, reaction, at the oxabispidine nitrogen, of a corresponding compound of formula I with a compound of formula XXV, $$R^{25}—L^4 \qquad \text{XXV}$$

wherein $R^{25}$ represents $C_{1-4}$ alkyl and $L^4$ is a leaving group such as halo, alkanesulfonate or arenesulfonate, for example at room temperature in the presence of an appropriate organic solvent (e.g. N,N-dimethylformamide), followed by purification (using e.g. HPLC) in the presence of a suitable counter-ion provider (e.g. $NH_4OAc$);

(w) conversion of one $R^4$ substituent to another using techniques well known to those skilled in the art; or (x) introduction of one or more (further) $R^4$ substituents to the aromatic ring using techniques well known to those skilled in the art (e.g. chlorination).

Compounds of formula II may be prepared by reaction of a compound of formula XXVI,

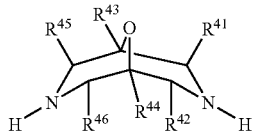 XXVI wherein $R^{41}$ to $R^{46}$ are as hereinbefore defined, with a compound of formula VIII as hereinbefore defined, for example as described hereinbefore for the synthesis of compounds of formula I (process step (d)), or, in the case of compounds of formula II wherein A represents $CH_2$ and $R^2$ represents —OH or $N(H)R^{14}$, wherein $R^{14}$ is as hereinbefore defined, with a compound of formula IX as hereinbefore defined, for example as described hereinbefore for the synthesis of compounds of formula I (process step (e)).

Compounds of formula IV may be prepared by reaction of a compound of formula II, as hereinbefore defined, with a compound of formula XXVII,

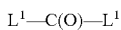 XXVII wherein $L^1$ is as hereinbefore defined, and in which the two $L^1$ groups may be the same or different, for example at between 0° C. and reflux temperature in the presence of a suitable base (e.g. triethylamine or potassium carbonate) and an appropriate organic solvent (e.g. toluene or dichloromethane).

Compounds of formula VII may be prepared by reaction of a compound of formula XXVI, as hereinbefore defined, with a compound of formula III, as hereinbefore defined, for example as described hereinbefore for the synthesis of compounds of formula I (process step (a)), or, in the case of compounds of formula VII wherein $R^1$ represents —C(O)N(H)$R^8$, with a compound of formula VI, as hereinbefore defined, for example as described hereinbefore for the synthesis of compounds of formula I (process step (c)).

Compounds of formula VII wherein $R^1$ represents —C(O)XR$^7$ or —C(O)N(R$^8$)R$^{5d}$ may alternatively be prepared by reaction of a compound of formula XXVI, as hereinbefore defined, with a compound of formula XXVII, as hereinbefore defined, for example as described hereinbefore for the synthesis of compounds of formula IV, followed by reaction of the resultant intermediate with a compound of formula V, as hereinbefore defined, for example as described hereinbefore for the synthesis of compounds of formula I (process step (b)).

Compounds of formula VIII may be prepared by standard techniques. For example, compounds of formula VIII in which:

(1) B represents —Z—O— may be prepared by coupling a compound of formula XI, as hereinbefore defined, to a compound of formula XXVIII,

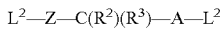 XXVIII wherein $R^2$, $R^3$, A, Z and $L^2$ are as hereinbefore defined, and the two $L^2$ groups may be the same or different; or (2) B represents —C(O)N(R$^{20}$)— may be prepared by coupling a compound of formula XXIX,

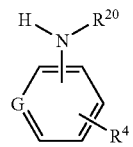 XXIX wherein G, $R^4$ and $R^{20}$ are as hereinbefore defined, to a compound of formula XXX,

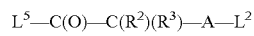 XXX wherein $L^5$ represents a suitable leaving group (e.g. —OH or halo) and $R^2$, $R^3$, A and $L^2$ are as hereinbefore defined;

in both cases, under conditions which are well known to those skilled in the art.

Compounds of formula VIII in which A represents —(CH$_2$)$_2$—, $R^2$ and $R^3$ both represent H, B represents —CH$_2$— and G represents CH may be prepared by reaction of a compound of formula XXXA,

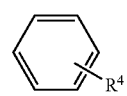 XXXA wherein $R^4$ as is hereinbefore defined, but preferably comprises a single ortho- or para-directing substitutable group, such as halo, with succinic anhydride under standard Friedel-Crafts acylation conditions, followed by:

(i) reduction of the resultant intermediate (which may be a two-step process);
(ii) conversion of the terminal hydroxy group to an appropriate $L^2$ group; and, if necessary,
(iii) conversion of one $R^4$ group to another, all of which steps may be carried out under conditions that are well known to those skilled in the art.

Compounds of formula VIII in which A represents $C_{1-6}$ alkylene, B represents a direct bond or $C_{1-4}$ alkylene, $R^2$ and $R^3$ independently represent H or $C_{1-6}$ alkyl, provided that when A represents $C_1$ alkylene and B represents a single bond, $R^2$ and $R^3$ both represent H, and G represents CH, may be prepared by coupling a compound of formula XXXB,

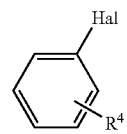 XXXB wherein Hal represents fluoro, chloro, bromo or iodo and $R^4$ is as hereinbefore defined, to a compound of formula XXXC,

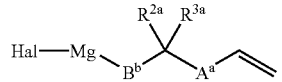 XXXC wherein $R^{2a}$ and $R^{3a}$ represent H or $C_{1-6}$ alkyl as appropriate, $A^a$ represents a direct bond or $C_{1-4}$ alkylene, $B^b$ represents a direct bond or $C_{1-4}$ alkylene, and Hal, $R^2$ and $R^3$ are as hereinbefore defined, or with a vinyl magnesium halide, for example at between −25° C. and room temperature in the presence of a suitable zinc(II) salt (e.g. anhydrous $ZnBr_2$), an appropriate catalyst (e.g. $Pd(PPh_3)_4$ or $Ni(PPh_3)_4$) and a reaction-inert organic solvent (e.g. THF, toluene or diethyl ether), followed by:

(i) reduction of the resultant intermediate, in the presence of a suitable borane or borane-Lewis base complex (e.g. borane-dimethyl sulfide), an appropriate solvent (e.g. diethyl ether, THF, or a mixture thereof;

(ii) oxidation of the resulting borane adduct with a suitable oxidising agent (e.g. sodium perborate); and (iii) conversion of the resulting OH group to an $L^2$ group under conditions known to those skilled in the art.

Compounds of formula VIII in which A represents a direct bond or $C_{1-6}$ alkylene, B represents $C_{2-4}$ alkylene, $R^2$ and $R^3$ independently represent H or $C_{1-6}$ alkyl and G represents CH may be prepared by coupling a compound of formula XXXD,

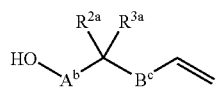

XXXD wherein $A^b$ represents a direct bond or $C_{1-6}$ alkylene, $B^c$ represents a direct bond or $C_{1-2}$ alkylene, and $R^{2a}$ and $R^{3a}$ are as hereinbefore defined, or a terminal alkyne equivalent thereof, with a compound of formula XXXB as hereinbefore defined, for example under standard metal-catalysed vinylation conditions, such as Heck conditions (for example in the presence of suitable palladium catalyst system (e.g. $Pd(OAc)_2$ and o-tolylphosphine), for example at between room and reflux temperature in the presence of a suitable solvent (e.g. THF, DMF, dimethyl ether, toluene, water, ethanol or mixtures thereof) and optionally in the presence of an appropriate base (e.g. triethylamine)), or, where the reaction is carried out using a terminal alkyne, under coupling conditions that will be known to those skilled in the art (for example at between room and reflux temperature in the presence of a suitable solvent (e.g. THF, DMF, dimethyl ether, toluene, water, ethanol or mixtures thereof), an appropriate base (e.g. diethylamine) and optionally in the presence of a suitable catalyst (e.g. a copper salt such as copper(I) iodide)), followed by:

(i) hydrogenation of the resultant alkene (or alkyne) intermediate, for example in the presence of a suitable supported palladium catalyst (e.g. Pd on $CaCO_3$ or Pd/C), for example at room temperature in the presence of a suitable solvent (e.g. a lower alkyl alcohol, such as methanol); and (ii) conversion of the OH group to an $L^2$ group, under conditions known to those skilled in the art.

Compounds of formula VIII in which the group —A—C($R^2$)($R^3$)—B— represents —$(CH_2)_{3-11}$— may be prepared by reaction of a corresponding compound of formula VIII in which the group —A—C($R^2$)($R^3$)—B— represents —$(CH_2)_{1-9}$— with diethylmalonate using standard malonic ester synthesis, followed by:

(i) reduction of the resultant intermediate; and (ii) conversion of the terminal hydroxy group to an appropriate $L^2$ group, both of which steps may be carried out under conditions that are well known to those skilled in the art.

Compounds of formula VIII in which A represents $C_{1-6}$ alkylene, B represents —Z—N($R^{20}$)— (in which latter case, Z is attached to the carbon atom bearing $R^2$ and $R^3$), G represents CH and Z and $R^{20}$ are as hereinbefore defined, may be prepared by coupling a compound of formula XXXB as hereinbefore defined, to a compound of formula XXXE,

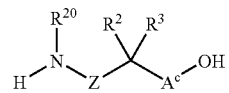

XXXE wherein $A^c$ represents $C_{1-6}$ alkylene and Z, $R^{20}$, $R^2$ and $R^3$ are as hereinbefore defined, for example at elevated temperature under conditions well known to those skilled in the art, followed by conversion of the hydroxy group to an $L^2$ group under conditions known to those skilled in the art (for example, where the $L^2$ group is p-toluenesulfonato, the conversion may be carried out by reaction between the intermediate hydroxy compound and p-toluenesulfonyl chloride in the presence of a suitable base (e.g. triethylamine) and an appropriate solvent (e.g. dichloromethane), and optionally in the presence of a suitable catalyst (e.g. DMAP, for example at between 0.1 and 10% (w/w) (e.g. 1% (w/w)) relative to mass of the intermediate hydroxy compound).

Compounds of formula VIII in which A represents a direct bond or $C_{1-6}$ alkylene, B represents $C_{1-4}$ alkylene and G represents N may be prepared by coupling a compound of formula XXXF

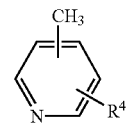

XXXF wherein $R^4$ is as hereinbefore defined, to a compound of formula XXXG,

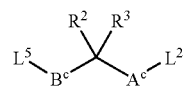

XXXG wherein $B^c$ represents a direct bond or $C_{1-3}$ alkylene and $A^c$, $L^2$, $L^5$, $R^2$ and $R^3$ are as hereinbefore defined, for example by reacting the compound of formula XXXF with a strong base such as butyl lithium or phenyl lithium (e.g. at −60° C., in the presence of a polar solvent, such as THF), followed by addition of the deprotonated intermediate to a compound of formula XXXG (e.g. at −65° C.) in the presence of a suitable solvent (such as THF).

Compounds of formula VIII in which A represents $C_2$ alkylene and $R^2$ represents —$OR^{13}$, in which $R^{13}$ represents $C_{1-6}$ alkyl —E-aryl or —E—$Het^6$ may alternatively be prepared by reaction of a compound of formula XIII, as hereinbefore defined, with a compound of formula XXXI,

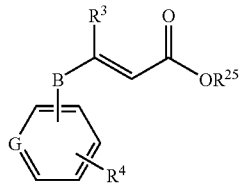

XXXI wherein $R^3$, $R^4$, $R^{25}$, B and G are as hereinbefore defined, for example at between ambient temperature (e.g. 25° C.) and reflux temperature in the presence of a suitable base (e.g. potassium carbonate) and an appropriate organic solvent (e.g. acetonitrile), followed by conversion of the ester functionality to an $L^2$ group (in which $L^2$ is as hereinbefore defined), under conditions that are well known to those skilled in the art.

Compounds of formula IX may be prepared in accordance with techniques which are known to those skilled in the art. For example, compounds of formula IX in which:

(1) B represents —$CH_2O$— and Y represents O may be prepared by reaction of a compound of formula XI, as hereinbefore defined, with a compound of formula XXXII

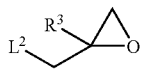

XXXII wherein $R^3$ and $L^2$ are as hereinbefore defined, for example at elevated temperature (e.g. between 60° C. and reflux temperature) in the presence of a suitable base (e.g. potassium carbonate or NaOH) and an appropriate organic solvent (e.g. acetonitrile or toluene/water), or as otherwise described in the prior art;

(2) $R^3$ represents H, B represents a direct bond, $C_{1-4}$ alkylene, —Z—N($R^{20}$)—, —Z—S(O)$_n$— or —Z—O— (in which, in each case, the group —Z represents $C_{1-4}$ alkylene attached to the carbon atom bearing $R^3$) and Y represents O may be prepared by reduction of a compound of formula XXXIIIA or XXXIIIB,

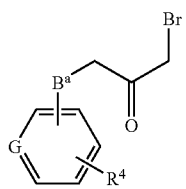

XXXIIIA

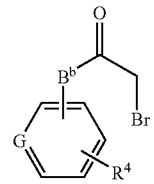

XXXIIIB wherein $B^a$ represents —$Z^a$—N($R^{20}$), —$Z^a$—S(O)$_n$— or —$Z^a$—O— (in which groups $Z^a$ represents a direct bond or $C_{1-3}$ alkylene attached to the carbon atom bearing $R^3$), and $B^b$, $R^4$, $R^{20}$, G and n are as hereinbefore defined, for example at between −15° C. and room temperature in the presence of a suitable reducing agent (e.g. $NaBH_4$) and an appropriate organic solvent (e.g. THF), followed by an internal displacement reaction in the resultant intermediate, for example at room temperature in the presence of a suitable base (e.g. potassium carbonate) and an appropriate organic solvent (e.g. acetonitrile);

(3) B represents a direct bond, $C_{1-4}$ alkylene, —Z—N($R^{20}$)—, —Z—S(O)$_2$— or —Z—O— (in which, in each case, the group Z represents $C_{1-4}$ alkylene attached to the carbon atom bearing $R^3$) and Y represents O may be prepared by oxidation of a compound of formula XXXIVA or XXXIVB,

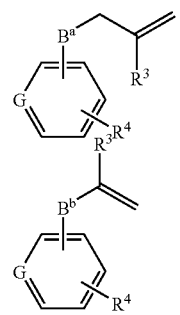

XXXIVA

XXXIVB wherein $R^3$, $R^4$, $B^a$, $B^b$ and G are as hereinbefore defined, in the presence of a suitable oxidising agent (e.g. mCPBA), for example by refluxing in the presence of a suitable organic solvent (e.g. dichloromethane); or (4) B represents —Z—O—, in which group Z represents $C_{1-4}$ alkylene attached to the carbon atom bearing $R^3$, and Y represents —N($R^{14}$), wherein $R^{14}$ represents —C(O)$OR^{16b}$ or —S(O)$_2R^{16c}$, may be prepared by cyclisation of a compound of formula XXXV,

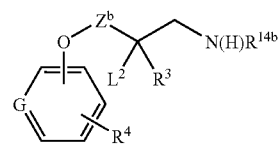

XXXV wherein $R^{14b}$ represents —C(O)$OR^{16b}$ or —S(O)$_2R^{16c}$, $Z^b$ represents $C_{1-4}$ alkylene attached to the carbon atom bearing $R^3$ and $R^3$, $R^4$, $R^{16b}$, $R^{16c}$, G and $L^2$ are as hereinbefore defined, for example at between 0° C. and reflux temperature in the presence of a suitable base (e.g. sodium hydroxide), an appropriate solvent (e.g. dichloromethane, water, or a mixture thereof) and, if necessary, a phase transfer catalyst (such as tetrabutylammonium hydrogensulfate).

Compounds of formula X may be prepared in a similar fashion to compounds of formula I (see, for example process steps (a) to (e)).

Compounds of formula XIV may be prepared by replacement of the —OH group of a compound of formula I in which $R^2$ represents —OH with an $L^2$ group under conditions that are known to those skilled in the art.

Compounds of formula XV in which E represents a direct bond may be prepared by reaction of a compound of formula I in which $R^2$ represents —OH with a compound of formula XXXVI,

  XXXVI wherein $R^{26}$ represents $C_{1-4}$ alkyl or aryl (which two groups are optionally substituted by one or more substituents selected from $C_{1-4}$ alkyl, halo and nitro), for example at between −10 and 25° C. in the presence of a suitable solvent (e.g. dichloromethane), followed by reaction with a suitable source of the azide ion (e.g. sodium azide), for example at between ambient and reflux temperature in the presence of an appropriate solvent (e.g. N,N-dimethylformamide) and a suitable base (e.g. sodium hydrogencarbonate).

Compounds of formula XV may alternatively be prepared by reaction of a compound of formula VII, as hereinbefore defined, with a compound of formula XXXVII,

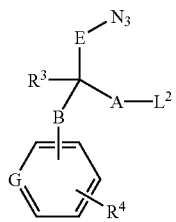  XXXVII wherein $R^3$, $R^4$, A, B, E, G and $L^2$ are as hereinbefore defined, for example under analogous conditions to those described hereinbefore for the synthesis of compounds of formula I (process step (d)).

Compounds of formula XX may be prepared by removing an optionally substituted benzyloxycarbonyl unit from (i.e. deprotecting) a corresponding compound of formula I in which B represents —N($R^{20}$)C(O)OCH$_2$— and A represents J, wherein $R^{20}$ and J are as hereinbefore defined, for example under conditions which are known to those skilled in the art.

Compounds of formula XXIII may be prepared by reaction of a compound of formula XXXVIII,

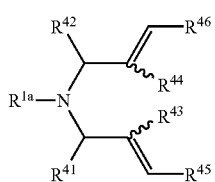  XXXVIII wherein the wavy bonds indicate optional E—, Z— or mixed E— and Z— geometry about the double bonds, and $R^{1a}$ and $R^{41}$ to $R^{46}$ are as hereinbefore defined, with water and a suitable source of the mercury(II) ion (e.g. mercury(II) acetate), for example at between 0 and 30° C., optionally in the presence of an appropriate organic solvent (e.g. THF), followed by the conversion of the two resulting mercurialkyl functions to $L^2$ groups, wherein $L^2$ is as hereinbefore defined, under conditions known to those skilled in the art (for example, in the case where $L^2$ represents iodo, reaction with iodine at between room and reflux temperature in the presence of a suitable solvent (e.g. chloroform, water or a mixture thereof)).

Compounds of formula XXIII may alternatively be prepared by reaction of a compound of formula XXXIX,

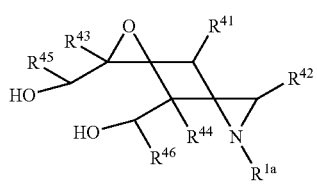  XXXIX wherein $R^{1a}$ and $R^{41}$ to $R^{46}$ are as hereinbefore defined, with a reagent that will convert the two —OH functionalities to $L^2$ groups under conditions known to those skilled in the art. For example, this conversion may be achieved, in the case of compounds of formula XXIII wherein $L^2$ represents chloro, bromo or iodo, by reaction of a compound of formula XXXIX with a suitable halogenating agent (for example: triphenylphosphine or bis(diphenylphosphino)ethane combined with the halogen (e.g. bromine or iodine)) in the presence of a suitable base (e.g. imidazole) and a suitable to solvent (e.g. dichloromethane, ether and/or acetonitrile), for example as described in *Synth. Commun.* 1990, 20(10), 1473. Suitable halogenating agents also include: triphenylphosphine combined with carbon tetrachloride, carbon tetrabromide, hexachloroethane or hexachloroacetone; triphenylphosphine dibromide; or triphenylphosphine combined with diethylazodicarboxylate and methyl iodide. In the case of compounds of formula XXIII wherein $L^2$ represents an arenesulfonate or alkanesulfonate (e.g. p-toluenesulfonate, 2- or 4-nitrobenzenesulfonate, methanesulfonate or trifluoromethanesulfonate), the conversion may alternatively be achieved by reaction of a compound of formula XXXIX with an appropriate arenesulfonyl or alkanesulfonyl derivative (e.g. p-toluenesulfonyl chloride, 4-nitrobenzenesulfonyl chloride or trifluoromethanesulfonic anhydride), in the presence of a suitable base (e.g. triethylamine, pyridine or N,N-diisopropylethylamine) and an appropriate organic solvent (e.g. dichloromethane or acetonitrile).

Compounds of formula XXVI (or an N-protected derivative thereof) may be prepared from a corresponding compound of formula XL,

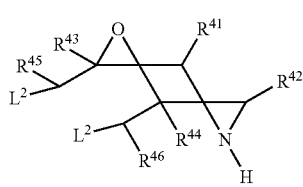  XL or an N-protected derivative thereof (e.g. where the protecting group is an $R^{1a}$ group, wherein $R^{1a}$ is as hereinbefore defined), wherein $R^{41}$ to $R^{46}$ and $L^2$ are as hereinbefore defined, with ammonia (or a protected derivative thereof (e.g. benzylamine)), for example under conditions described hereinbefore for the synthesis of compounds of formula I (process step (t)).

Compounds of formula XXXVII may be prepared in analogous fashion to compounds of formula XV (i.e. from the corresponding alcohol).

Compounds of formula XXXVIII may be prepared by reaction of a compound of formula XLI,

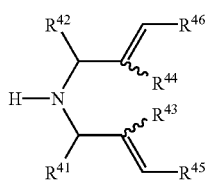

XLI wherein the wavy bonds indicate optional E—, Z— or mixed E— and Z— geometry about the double bonds, and $R^{41}$ to $R^{46}$ are as hereinbefore defined, with a compound of formula III in which $R^1$ represents —C(O)$XR^7$, —C(O)N($R^8$)$R^{5d}$ or —S(O)$_2R^9$, wherein $R^{5d}$, $R^7$, $R^8$ and $R^9$ are as hereinbefore defined, for example at between −10 and 25° C. in the presence of a suitable base (e.g. NaOH, triethylamine, pyridine or potassium carbonate) and an appropriate solvent (e.g. ether, water, dichloromethane, THF, or mixtures thereof).

Compounds of formula XXXIX may be prepared by reaction of a compound of formula XLII,

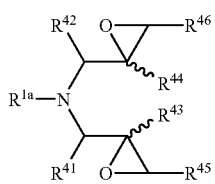

XLII wherein the wavy bonds indicate optional R—, S— or mixed R— and S— stereochemistry at the asymmetric carbon atoms, and $R^{1a}$ and $R^{41}$ to $R^{46}$ are as hereinbefore defined, with water, for example at between room and reflux temperature in the presence of a suitable catalyst (e.g. a protic acid such as sulfuric, methanesulfonic or trifluoroacetic acid, an acidic ion-exchange resin such as Amberlyst® 15 or Nafion®, a Lewis acid such as $ZnSO_4$ or Yb(III) trifluoromethanesulfonate or a base such as sodium hydroxide or tetrabutylammonium hydroxide), an appropriate solvent (e.g. THF, water, 1,4-dioxane or 1-methyl-2-pyrrolidinone, or mixtures thereof (e.g. THF/water)), and optionally (when a basic catalyst is used) in the presence of a suitable phase transfer catalyst (e.g. Triton® B).

The reaction may be advantageously be performed using compounds of formula XLII having enantiomeric (or diastereomeric) enrichment at the chiral centres identified above. The use of such enantiomerically- (or diastereomerically-) enriched compounds of formula XLII in the formation of compounds of formula XXXIX may have the advantage that a greater proportion of the product diol is obtained as the cis-isomer (i.e. the conformation of compounds of formula XXXIX depicted above). Those skilled in the art will appreciate that such an increased proportion of cis-isomer may be retained in the conversion of compounds of formula XXXIX to compounds of formula XXIII, and thus may eventually lead to a higher yield of compounds of formula I (via process step (t)).

The reaction may also be advantageously performed using compounds of formula XLII wherein $R^{1a}$ represents —S(O)$_2R^9$ (e.g. wherein $R^9$ represents optionally substituted phenyl, such as 2- or 4-fluorophenyl, 2- or 4-chlorophenyl, 4-bromophenyl, 4-methylphenyl, 4-methoxyphenyl, 2- or 4-nitrophenyl, 2,4,6-trimethylphenyl). The use of such ring-substituted benzenesulfonyl derivatives may have the advantage that purification of the resulting compound of formula XXXIX may be made more straightforward (e.g. requiring only a simple recrystallisation step) and/or that, in a compound of formula I (synthesised via compounds of formulae XXXIX and XXIII), removal of the —S(O)$_2R^9$ group (allowing its replacement with another $R^1$ group) may be made more straightforward (e.g. enabling the use of milder reaction conditions).

Compounds of formula XL may be prepared in an analogous fashion to compounds of formula XXIII, as hereinbefore defined (i.e. from e.g. the corresponding diallylamine).

Compounds of formula XLII in which the substituent $R^{42}$ has the same identity as $R^{41}$, $R^{44}$ has the same identity as $R^{43}$ and $R^{46}$ has the same identity as $R^{45}$ may be prepared by reaction of two or more equivalents of a compound of formula XLIII,

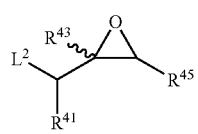

XLIII wherein the wavy bond indicates optional R—, S— or mixed R— and S— stereochemistry at the asymmetric carbon atom, and $R^{41}$, $R^{43}$, $R^{45}$ and $L^2$ are as hereinbefore defined, with one equivalent of a compound of formula XLIV, $R^{1a}NH_2$

XLIV wherein $R^{1a}$ is as hereinbefore defined, for example at between room and reflux temperature in the presence of a suitable base (e.g. an alkali metal carbonate such as cesium carbonate, sodium hydroxide, sodium hydride or lithium diisopropylamide), an appropriate solvent (e.g. acetonitrile, N,N-dimethylformamide, THF, toluene, water or mixtures thereof), and optionally in the presence of a phase transfer catalyst (e.g. tricaprylyl-methylammonium chloride). Preferred bases include sodium hydroxide and preferred solvents include water. The reaction is advantageously performed with compounds of formula XLIV wherein $R^{1a}$ represents —S(O)$_2R^9$ (e.g. wherein $R^9$ represents optionally substituted phenyl, such as 2- or 4-fluorophenyl, 2- or 4-chlorophenyl, 4-bromophenyl, 4-methylphenyl, 4-methoxyphenyl, 2- or 4-nitrophenyl, 2,4,6-trimethylphenyl). The use of such ring-substituted benzenesulfonyl derivatives may have the advantage that purification of the resulting compound of formula XLII may be made more straightforward (e.g. requiring only a simple recrystallisation step).

Compounds of formulae XLIII and XLIV may also be reacted together in this way in the presence of water in order to give a direct, "one-pot" process providing a compound of formula XXXIX. Such "one-pot" reactions may be carried out, for example, by using a biphasic reaction mixture comprising a solution of XLIII and XLIV in an organic solvent (e.g. toluene), and an aqueous solution of a base (e.g. sodium hydroxide). Alternatively, the aqueous solution of base may, after the formation of the intermediate compound of formula XLII is complete, be exchanged for an aqueous solution of an acid (e.g. either a protic or a Lewis acid). Any of the reaction steps in such biphasic mixtures may be carried out in the presence of a suitable phase transfer catalyst.

Compounds of formula XLII having enantiomeric (or diastereomeric) enrichment at the chiral centres identified above may be prepared by reaction of a compound of formula XLIV, as hereinbefore defined, with a compound of formula XLIII, as hereinbefore defined, having enantiomeric enrichment at the carbon atom to which $R^{43}$ is attached. Those skilled in the art will realise that this will lead to more of the isomer(s) required for further elaboration to compounds of formula I.

Compounds of formula XLII may alternatively be prepared by reaction of a compound of formula XXXVIII, as hereinbefore defined, with a suitable oxidising agent. Suitable conditions for this oxidation include, for example, reaction at between −25° C. and reflux temperature with a suitable peroxide or peracid (e.g. hydrogen peroxide, tert-butyl hydroperoxide or mCPBA), optionally in the presence of an appropriate solvent (e.g. dichloromethane, t-butanol, nitromethane, toluene, water, or mixtures thereof, a suitable catalyst (for example a protic acid, a Lewis acid, or a metal complex capable of forming a peroxide adduct, such as methyltrioxorhenium(VII) or a combination of sodium tungstate and (aminomethyl)phosphonic acid), and/or further appropriate additives (for example: in the case of oxidations carried out with methyltrioxorhenium(VII) and hydrogen peroxide, a basic additive such as pyridine or pyrazole; and in the case of oxidations with sodium tungstate and hydrogen peroxide, a phase transfer catalyst such as methyltri-n-octylammonium hydrogensulfate). Particular embodiments of this oxidation are described in patent applications EP A1 0 380 085 and WO 98/33786 A1, the disclosures in which documents are hereby incorporated by reference. When the oxidation is carried out in the presence of both a catalyst and water, one embodiment of the reaction involves a "one-pot" conversion of the compound of formula XXXVIII to a compound of formula XXXIX, as hereinbefore defined. This reaction proceeds via the catalysed hydrolysis of the intermediate compound of formula XLII.

Compounds of formula XLII in which the two epoxide chains are not identical (e.g. where $R^{41}$ and $R^{42}$ are not identical) may be prepared by reaction of a compound of formula XLIII, as hereinbefore defined, with a compound of formula XLV,

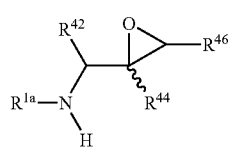

XLV wherein the wavy bond indicates optional R—, S— or mixed R— and S— stereochemistry at the asymmetric carbon atom, and $R^{1a}$, $R^{42}$, $R^{44}$, and $R^{46}$ are as hereinbefore defined, for example under conditions described hereinbefore for the synthesis of symmetrical compounds of formula XLII.

Compounds of formula XLV may be prepared by reaction of one or more equivalents of a compound of formula XLIV, as hereinbefore defined, with one equivalent of a compound of formula XLIII, for example under conditions as described hereinbefore for reaction between these two compounds.

Compounds of formula XLV may alternatively be prepared by oxidation of a corresponding compound of formula XLVI,

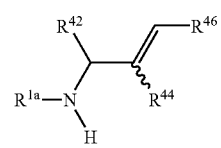

XLVI wherein the wavy bond indicates optional E—, Z— or mixed E— and Z— geometry about the double bond, and $R^{1a}$, $R^{42}$, $R^{44}$ and $R^{46}$ are as hereinbefore defined, for example under conditions as hereinbefore described for the synthesis of compounds of formula XLII.

Compounds of formula I may also be prepared, advantageously, by dehydrative cyclisation of compound of formula XLVII,

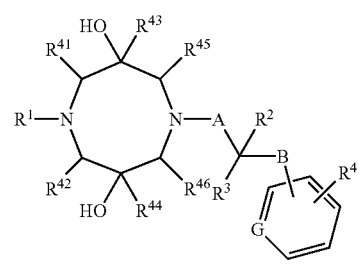

XLVII wherein A, B, G, $R^1$, $R^2$, $R^3$, $R^4$ and $R^{41}$ to $R^{46}$ are as hereinbefore defined, for example in the presence of a suitable dehydrating agent (such as: a strong acid (e.g. sulfuric acid (e.g. concentrated sulfuric acid), methanesulfonic acid (e.g. anhydrous methanesulfonic acid) and the like; an acid anhydride such as acetic anhydride or trifluoromethane-sulfonic anhydride; $P_2O_5$ in methanesulfonic acid; a phosphorous-based halogenating agent such as P(O)Cl$_3$, PCl$_3$ or PCl$_5$; and thionyl chloride).

This cyclisation process may be carried out in the presence of a suitable organic solvent system, which solvent system should not significantly react chemically with, or significantly give rise to stereochemical changes in, the reactants or product once formed, or significantly give rise to other side reactions. Preferred solvent systems include aromatic hydrocarbons (e.g. toluene or xylene).

This cyclisation process may be carried out at elevated temperature (e.g. up to the reflux temperature of the relevant solvent system, or higher if a pressurised system is employed). Clearly, appropriate reaction times and reaction temperatures depend upon the solvent system that is employed, as well as the reactants that are used and the compound that is to be formed, but these may be determined routinely by the skilled person.

Compounds of formula XLVII may advantageously be prepared by reaction of a compound of formula XLVIII,

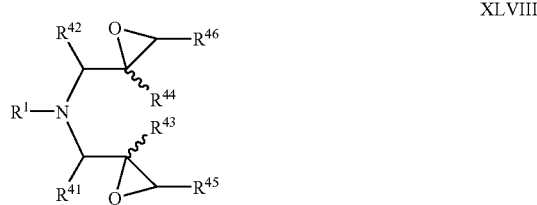

XLVIII wherein the wavy bonds indicate optional R—, S— or mixed R— and S— stereochemistry at the asymmetric carbon atoms, and $R^1$ and $R^{41}$ to $R^{46}$ are as hereinbefore defined, with a compound of formula XXIV as hereinbefore defined. This reaction may be carried out at between room temperature and the reflux temperature of any solvent that is employed. Suitable solvent systems that may be employed include organic solvent systems, which system should not significantly react chemically with, or significantly give rise to stereochemical changes in, the reactants or product once formed, or significantly give rise to other side reactions. Preferred solvent systems include lower alkyl alcohols (particularly primary alcohols (e.g. ethanol)) optionally in the presence of water, IMS, aromatic hydrocarbons (e.g. toluene) or mixtures thereof.

Compounds of formula XXIV may be prepared as described herein.

Compounds of formula XLVIII may be prepared according to or by analogy with the procedures described herein in relation to the preparation of compounds of formula XLII.

The formation of compounds of formula XLVII may be also be performed using compounds of formula XLVIII having enantiomeric (or diastereomeric) enrichment at the chiral centres identified hereinbefore. The use of such enantiomerically- (or diastereomerically-) enriched compounds of formula XLVIII in the formation of compounds of formula XLVII may have the advantage that a greater proportion of the product diol is obtained in a form (e.g. the trans-form) which facilitates the subsequent cyclisation, leading to a higher yield of compounds of formula I.

The formation of compounds of formula XLVII is preferably carried out using compounds of formula XLVIII in which $R^1$ represents $R^{1a}$, wherein $R^{1a}$ is as hereinbefore defined. The formation of compounds of formula XLVII is more preferably carried out using compounds of formula XLVIII in which $R^1$ represents —$S(O)_2R^9$ (e.g. wherein $R^9$ represents optionally substituted phenyl, such as 2- or 4-fluorophenyl, 2- or 4-chlorophenyl, 4-bromophenyl, 4-methylphenyl, 4-methoxyphenyl, 2- or 4-nitrophenyl, 2,4,6-trimethylphenyl and, especially, unsubstituted phenyl).

Preferred compounds of formula XXIV include those in which:
G represents CH;
A represents a direct bond;
B represents a direct bond;
$R^2$ represents H or $C_{1-6}$ alkyl;
$R^3$ represents H or $C_{1-6}$ alkyl;
$R^4$ is absent or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro.

We have found, surprisingly, that, when compounds of formula I are formed using this process (i.e. via compounds of formula XLVII), the employment of derivatives of formula XLVIII in which $R^1$ represents $R^{1a}$ (e.g. wherein $R^{1a}$ represents optionally-substituted benzenesulfonyl, such as described above), and benzylamine-type derivatives of formula XXIV (such as those described above), may have the advantage that, in the resultant compound of formula I, the presence of the $R^{1a}$ (e.g. —$S(O)_2R^9$) group and/or the benzylamine-type group allows for direct and facile replacement of that/those group(s) with other $R^1$ groups, and/or

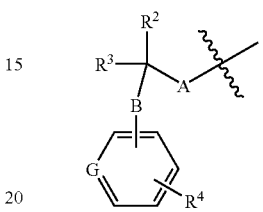

fragments, as appropriate, for example by employing reactions that are akin to "deprotection" reactions (see below), and subsequently performing coupling reactions (see, for example process steps (a), (c), (d) and (e)). We have found, if that benzenesulfonyl derivatives of formula XLVIII, and benzylamine-type derivatives of formula XXIV are employed, subsequent replacement steps may be made more straightforward (e.g. enabling the use of milder reaction conditions).

In this respect, certain compounds of the invention may further be employed as intermediates, useful in the manufacture of other compounds of the invention. Such compounds include, but are not limited to compounds of formula I in which:
$R^1$ represents —$S(O)_2R^9$, wherein $R^9$ represents optionally substituted phenyl, such as 2- or 4-fluorophenyl, 2- or 4-chlorophenyl, 4-bromophenyl, 4-methylphenyl, 4-methoxyphenyl, 2- or 4-nitrophenyl, 2,4,6-trimethylphenyl and, especially, unsubstituted phenyl;
$R^{41}$ to $R^{46}$ all represent H;
G represents CH;
A represents a direct bond;
B represents a direct bond;
$R^2$ represents H or $C_{1-6}$ alkyl;
$R^3$ represents H or $C_{1-6}$ alkyl;
$R^4$ is absent or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro.

Compounds of formula I that may, in particular, be employed as intermediates include, but are not limited to those in which:
$R^2$ and $R^3$ both represent H;
$R^4$ is absent; and/or
$R^9$ represents unsubstituted phenyl.

Further, compounds of formula I in which:
$R^{41}$ to $R^{46}$ all represent H;
$R^1$ represents straight- or branched-chain $C_{1-4}$ alkyl (e.g. $C_{1-3}$ alkyl such as methyl) terminated by $C(O)R^{5a}$ or —$N(H)C(O)OR^{10b}$;
$R^{5a}$ and $R^{10b}$ independently represent straight- or branched-chain $C_{2-6}$ alkyl (e.g. $C_{3-5}$ alkyl, such butyl (e.g. t-butyl));
$R^2$ represents H or OH;
$R^3$ represents H;
A represents $C_1$ alkylene or linear $C_2$ alkylene;

B represents —Z—, —Z—N(H)— or —Z—O— (in which latter two groups, Z is attached to the carbon atom bearing $R^2$ and $R^3$, and represents $C_1$ alkylene or linear $C_2$ alkylene);

G represents CH; and $R^4$ is a single cyano group in the para-position relative to B, may be prepared by a process which comprises the steps of:

(i) removal of the —$SO_2R^9$ group from a compound of formula I in which $R^1$ represents —$S(O)_2R^9$, wherein $R^9$ represents optionally substituted phenyl, $R^{41}$ to $R^{46}$ all represent H, G represents CH, A and B both represent direct bonds, $R^2$ and $R^3$ independently represent H or $C_{1-6}$ alkyl and $R^4$ is absent or represents one to three halo, methyl, methoxy or nitro groups, especially 2- or 4-fluoro, 2- or 4-chloro, 4-bromo, 4-methyl, 2,4,6-triethyl, 4-methoxy, or 2- or 4-nitro, to provide a compound of formula II as hereinbefore defined, in which $R^{41}$ to $R^{46}$ all represent H, G represents CH, A and B both represent direct bonds, $R^2$ and $R^3$ independently represent H or $C_{1-6}$ alkyl and $R^4$ is absent or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro, for example using standard deprotection conditions (e.g. in the presence of a standard deprotecting agent (such a hydrohalic acid (e.g. HBr, especially concentrated aqueous HBr) or a reducing, agent such as $LiAlH_4$), at or above room temperature (e.g. at reflux) with or without the presence of a solvent;

(ii) reaction of the resultant compound of formula II with a compound of formula III, as hereinbefore defined, in which $R^1$ represents straight- or branched-chain $C_{1-4}$ alkyl (e.g. $C_{1-3}$ alkyl, such as methyl) terminated by $C(O)R^{5a}$ or —$N(H)C(O)OR^{10b}$, in which $R^{5a}$ and $R^{10b}$ independently represent straight- or branched-chain $C_{2-6}$ alkyl (e.g. $C_{3-5}$ alkyl, such butyl (e.g. t-butyl)), to form a compound of formula I in which $R^1$ represents straight- or branched-chain $C_{1-4}$ alkyl (e.g. $C_{1-3}$ alkyl, such as methyl) terminated by $C(O)R^{5a}$ or —$N(H)C(O)OR^{10b}$, $R^{5a}$ and $R^{10b}$ independently represent straight- or branched-chain $C_{2-6}$ alkyl (e.g. $C_{3-5}$ alkyl, such butyl (e.g. t-butyl)), $R^{41}$ to $R^{46}$ all represent H, G represents CH, A and B both represent a direct bond, $R^2$ and $R^3$ independently represent H or $C_{1-6}$ alkyl and $R^4$ is absent or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro, for example under conditions described hereinbefore (see e.g. process (a)), e.g. in the presence of a suitable solvent (e.g. water, a lower alkyl alcohol, acetonitrile, or mixtures thereof and an appropriate base (e.g. sodium bicarbonate or potassium carbonate);

(iii) removal of the

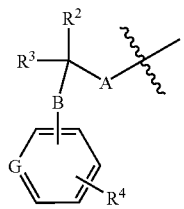

fragment from the resultant compound of formula I to provide a compound of formula VII in which $R^1$ represents straight- or branched-chain $C_{1-4}$ alkyl (e.g. $C_{1-3}$ alkyl such as methyl) terminated by $C(O)R^{5a}$ or —$N(H)C(O)OR^{10b}$, $R^{5a}$ and $R^{10b}$ independently represent straight- or branched-chain $C_{2-6}$ alkyl (e.g. $C_{3-5}$ alkyl, such butyl (e.g. t-butyl)), and $R^{41}$ to $R^{46}$ all represent H, for example under appropriate deprotection conditions, such as hydrogenation in the presence of a supported palladium catalyst (e.g. Pd/C), for example at room temperature in the presence of a suitable solvent (e.g. a lower alkyl alcohol, such as ethanol)); and (iv) reaction of the resultant compound of formula VII with a compound of formula VIII as hereinbefore defined, in which $R^2$ represents H or OH, $R^3$ represents H, A represents $C_1$ alkylene or linear $C_2$ alkylene, B represents —Z—, —Z—N(H)— or —Z—O— (in which latter two groups, Z is attached to the carbon atom bearing $R^2$ and $R^3$, and represents $C_1$ alkylene or linear $C_2$ alkylene), G represents CH and $R^4$ is a single cyano group in the para-position relative to B, and $L^2$ represents, for example, arenesulfonate (e.g. toluenesulfonate), for example under conditions described hereinbefore (see e.g. process (d)), such as at between room and reflux temperature, in the presence of a suitable base (e.g. potassium carbonate) and an appropriate organic solvent (e.g. a lower alkyl alcohol, such as ethanol).

The skilled person will appreciate that, if desired, the above steps may be performed in a different order to those that stated above, to provide the relevant compounds of formula I. For example, steps (iii) and (iv) may be carried out prior to steps (i) and (ii). Alternatively, steps (i) and (iii) (in either order) may be completed before steps (ii) and (iv) (in either order) are carried out. However, we prefer that the steps are performed in the above-stated order.

The process of making the compounds of formula I from compounds of formulae XLVIII and XXIV (i.e. via compounds of formula XLVII) may have the advantage that oxabispidine ring systems may be formed using fewer steps than methods described in the prior art, and, particularly, avoids the use of mercury-containing compounds (thereby eliminating the production of toxic, mercury-containing waste). This process offers a convenient synthetic route to key oxabispidine compounds, and allows differential protection at the nitrogen atoms.

Further, this process may have the advantage that compounds comprising the oxabispidine ring may be prepared in less time, more conveniently, and/or at a lower cost, than when prepared in processes described in the prior art.

Compounds of formulae III, V, VI, XI, XII, XIII, XVI, XVII, XVIII, XIX, XXI, XXII, XXIV, XXV, XXVII, XXVIII, XXIX, XXX, XXXA, XXXB, XXXC, XXXD, XXXE, XXXF, XXXG, XXXI, XXXII, XXXIIIA, XXXIIIB, XXXIVA, XXXIVB, XXXV, XXXVI, XLI, XLIII, XLIV and XLVI and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formulae I. For example, carbonyl may be reduced to hydroxy or alkylene, and hydroxy may be converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, sulfonamido (e.g. benzenesulfonamido), tert-butyloxycarbonyl, 9-fluorenyl-methoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are well known to those skilled in the art and as described hereinafter. For example, we have found that removal of an —$SO_2R^9$ group from an oxabispidine ring may take place conveniently by employment of an appropriate strong acid, such as a hydrohalic acid (especially HBr) e.g. as described hereinbefore.

The use of protecting groups is fully described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided: (a) a compound of formula II, as hereinbefore defined, or a protected derivative thereof, optionally in the form of a salt and/or a solvate; (b) a compound of formula IV, as hereinbefore defined, or a protected derivative thereof; (c) a compound of formula VII, as hereinbefore defined, or a protected derivative thereof (provided that $R^1$ does not represent —$S(O)_2R^9$, wherein $R^9$ represents unsubstituted phenyl). Preferred compounds of formula VII include those in which $R^1$ does not represent $C(O)OR^7$, in which $R^7$ is tert-butyl; (d) a compound of formula X, as hereinbefore defined, or a protected derivative thereof; (e) a compound of formula XIV, as hereinbefore defined, or a protected derivative thereof; (f) a compound of formula XV, as hereinbefore defined, or a protected derivative thereof; (g) a compound of formula XX, as hereinbefore defined, or a protected derivative thereof; (h) a compound of formula XXIII, as hereinbefore defined, or a protected derivative thereof, provided that $L^2$ does not represent iodo; (i) a compound of formula XXXIX, or a protected derivative thereof; and (j) a compound of formula XLII, or a protected derivative thereof.

Preferred compounds of formula II include those in which:

$R^{41}$ to $R^{46}$ all represent H;

G represents CH;

A represents a direct bond;

B represents a direct bond;

$R^2$ represents H or $C_{1-6}$ alkyl;

$R^3$ represents H or $C_{1-6}$ alkyl; and/or $R^4$ is absent or represents one to three halo, methyl, methoxy or nitro groups.

Particularly preferred compounds of formula II include those in which:

$R^2$ and $R^3$ both represent H, and $R^4$ is absent, optionally in the form of a sulfate, hemisulfate or, especially, a hydrochloride (such as a dihydrochloride) salt, which salt is optionally a hydrate (e.g. a hemihydrate).

Preferred compounds of formula VII include those which are not:

tert-butyl 9-oxa-3,7-diazabicyclo[3.3.1]nonane-3-carboxylate.

Preferred compounds of formula XLVII include those in which the group $R^1$ and the group

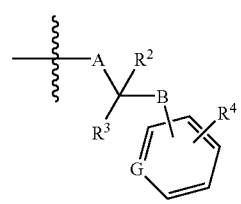

are different, and as such include those compounds of formula XLVII in which:

$R^1$ represents —$C(O)XR^7$, —$C(O)N(R^8)R^{5d}$ or —$S(O)_2R^9$ (wherein X, $R^{5d}$, $R^7$, $R^8$ and $R^9$ are as hereinbefore defined);

$R^2$ and $R^3$ do not together represent =O when A represents a direct bond.

Particularly preferred compounds of formula XLVII include those in which $R^1$ represents —$S(O)_2R^9$, wherein $R^9$ represents aryl (such as phenyl, particularly unsubstituted phenyl);

G represents CH;

A represents a direct bond;

B represents a direct bond;

$R^2$ represents H or $C_{1-6}$ alkyl;

$R^3$ represents H or $C_{1-6}$ alkyl;

$R^4$ is absent or represents one to three halo, methyl, methoxy or nitro groups, especially 2- or 4-fluoro, 2- or 4-chloro, 4-bromo, 4-methyl, 2,4,6-trimethyl, 4-methoxy, or 2- or 4-nitro.

Medical and Pharmaceutical Use

Compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization, thus prolonging the QT interval, and, in particular, to exhibit class III activity. Although compounds of the invention have been found to exhibit class III activity in is particular, in the treatment of arrhythmias, their mode(s) of activity is/are not necessarily restricted to this class.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.005 to 25.0 mg/kg body weight at oral administration and about 0.005 to 10.0 mg/kg body weight at parenteral administration. Preferable ranges of daily doses of the compounds of the invention in therapeutic treatment of humans are about 0.005 to 10.0 mg/kg body weight at oral administration and about 0.005 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects In Anaesthetised Guinea Pigs

Guinea pigs weighing between 660 and 1100 g were used. The animals were housed for at least one week before the experiment and had free access to food and tap water during that period.

Anaesthesia was induced by an intraperitoneal injection of pentobarbital (40 to 50 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (2 ms duration, twice the diastolic threshold) was performed with a custom-made constant current stimulator. The heart was paced at a frequency just above the normal sinus rate during 1 minute every fifth minute throughout the study.

The blood pressure, the MAP signal and the lead II ECG were recorded on a Mingograph inkjet recorder (Siemens-Elema, Sweden). All signals were collected (sampling frequency 1000 Hz) on a PC during the last 10 seconds of each pacing sequence and the last 10 seconds of the following minute of sinus rhythm. The signals were processed using a custom-made program developed for acquisition and analysis of physiological signals measured in experimental animals (see Axenborg and Hirsch, *Comput. Methods Programs Biomed.* 41, 55 (1993)).

The test procedure consisted of taking two basal control recordings, 5 minutes apart, during both pacing and sinus rhythm. After the second control recording, the first dose of the test substance was infused in a volume of 0.2 mL into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class III electrophysiological potency of the agent under investigation ($D_{10}$).

Test B

Glucocorticoid-treated Mouse Fibroblasts as a Model to Detect Blockers of the Delayed Rectifier K Current IC50 for K channel blockade was determined using a microtitre plate based screen method, based on membrane potential changes of glucocorticoid-treated mouse fibroblasts. The membrane potential of glucocorticoid-treated mouse fibroblasts was measured using fluorescence of the bisoxonol dye $DiBac_{4(3)}$, which could be reliably detected using a fluorescence laser imaging plate reader (FLIPR). Expression of a delayed rectifier potassium channel was induced in mouse fibroblasts by 24 hours exposure to the glucocorticoide dexamehasone (5 μM). Blockade of these potassium channels depolarised the fibroblasts, resulting in increased fluorescence of $DiBac_{4(3)}$.

Mouse ltk fibroblasts (L-cells) were purchased from American Type Culture Collection (ATCC, Manassa, Va.), and were cultured in Dulbeccos modified eagle medium supplemented with fetal calf serum (5% vol/vol), penicillin (500 units/mL), streptomycin (500 μg/mL) and L-alanine-L-glutamine (0.862 mg/mL). The cells were passaged every 3–4 days using trypsin (0.5 mg/mL in calcium-free phosphate buffered saline, Gibco BRL). Three days prior to experiments, cell-suspension was pipetted out into clear-bottom, black plastic, 96-well plates (Costar) at 25,000 cells/well.

The fluorescence probe $DiBac_{4(3)}$ (DiBac Molecular probes) was used to measure membrane potential. $DiBac_{4(3)}$ maximally absorbs at 488 nM and emits at 513 nM. $DiBac_{4(3)}$ is a bisoxonol, and thus is negatively charged at pH 7. Due to its negative charge, the distribution of $DiBac_{4(3)}$ across the membrane is dependent upon the transmembrane potential: if the cell depolarizes (i.e. the cell interior becomes less negative relative to cell exterior), the $DiBac_{4(3)}$ concentration inside the cell increases, due to electrostatic forces. Once inside the cell, $DiBac_{4(3)}$ molecules can bind to lipids and proteins, which causes an increase in fluorescence emission. Thus, a depolarization will be reflected by an increase in $DiBac_{4(3)}$ fluorescence. The change in $DiBac_{4(3)}$ fluorescence was detected by a FLIPR.

Prior to each experiment, the cells were washed 4 times in phosphate-buffered saline (PBS) to remove all culture media. The cells were then treated with 5 μM $DiBac_{4(3)}$ (in 180 μL of PBS) at 35° C. Once a stable fluorescence was reached (usually after 10 min), 20 μL of the test substance was added, using FLIPR's internal 96 well pipetting system. Fluorescence measurements were then taken every 20 sec for a further 10 min. All experiments were carried out at 35° C., due to the high temperature sensitivity of both delayed rectifier potassium channel conductance and $DiBac_{4(3)}$ fluorescence. Test substances were prepared in a second 96 well plate, in PBS containing 5 μM $DiBac_{4(3)}$. The concentration of substance prepared was 10 times that of the desired concentration in the experiment as an additional 1:10 dilution occurred during addition of substance during the experiment. Dofetilide (10 μM) was used as a positive control, i.e. to determine the maximum increase in fluorescence.

Curve-fitting, used to determine the IC50 values, was performed with the Graphpad Prism program (Graphpad Software Inc., San Diego, Calif.).

Test C

Metabolic Stability of Test Compounds

An in vitro screen was set up to determine the metabolic stability of the compounds of the invention.

The hepatic S-9 fraction from dog, man, rabbit and rat with NADPH as co-factor was used. The assay conditions were as follows: S-9 (3 mg/mL), NADPH (0.83 mM), Tris-HCl buffer (50 mM) at pH 7.4 and 10 μM of test compound.

The reaction was started by addition of test compound and terminated after 0, 1, 5, 15 and 30 minutes by raising the pH in the sample to above 10 (NaOH; 1 mM). After solvent extraction, the concentration of test compound was measured against an internal standard by LC (fluorescence/UV detection).

The percentage of test compound remaining after 30 minutes (and thus $t_{1/2}$) was calculated and used as a measure for metabolic stability.

The invention is illustrated by way of the following examples.

EXAMPLES

General Experimental Procedures

Mass spectra were recorded on one of the following instruments: a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and $^{13}$C NMR measurements were performed on a BRUKER ACP 300 and Varian 300, 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Synthesis of Intermediates

The following intermediates were not commercially available, and were therefore prepared by the methods described below.

Preparation A tert-Butyl
9-oxa-3,7-diazabicyclo[3.3.1]nonane-3-carboxylate
hydrochloride (i)
2,6-Bis(iodomethyl)-4-(phenylsulfonyl)morpholine The sub-title compound was prepared according to both of the following two methods:

(a) To a stirred mixture of water (835 mL), chloroform (1.25 L) and iodine (418.7 g, 1.65 mol) under an inert atmosphere (N$_2$) was added, portion-wise over a period of 30 min, 2,6-bis[(acetoxymercuri)methyl]-4-(phenylsulfonyl)morpholine (prepared as described in Chem. Ber. 96, 2827 (1963); 421.3 g, 0.55 mol), during which time the reaction mixture was warmed to reflux. After addition was complete, reflux was continued overnight before the mixture was allowed to cool to room temperature. The mixture was filtered and the chloroform layer separated. A saturated aqueous solution of Na$_2$S$_2$O$_3$ was added to the organic solution until the iodine colour disappeared. The organic layer was again separated, then dried (Na$_2$SO$_4$), filtered and concentrated in vacuo to yield 279.9 g (100%) of the sub-title compound as a light yellow crystalline solid. HPLC analysis indicated this product to be composed of 46% cis-isomer and 54% trans-isomer.

(b) Acetonitrile (50 mL) and then ether (150 mL) were added to triphenylphosphine (20.1 g, 77 mmol). Imidazole (5.24 g, 77 mmol) was added and the solution cooled to 5° C. Iodine (19.5 g, 77 mmol) was added, causing the temperature to rise to 17° C. A solution of 2,6-bis-(hydroxymethyl)4-(phenylsulfonyl)morpholine (Preparation L; 10.65 g, 37 mmol) in acetonitrile (50 mL) was added and the reaction stirred at room temperature for 22 hours. Aqueous sodium thiosulfate (5%, 100 mL) was added and the layers separated. The organic phase was washed with dilute sulfuric acid (100 mL) and then was concentrated under reduced pressure. The residue was purified by chromatography over silica (200 g), eluting with dichloromethane (1.5 L), to give a yellow oil. This was triturated with ether to give the title compound as a yellow solid (a 1:1 mixture of cis- and trans-isomers; 6.1 g, 37%). The ether wash contained impure product (1.90 g).

API MS: m/z=508[C$_{12}$H$_{15}$I$_2$NO$_3$S+H]$^+$.

(ii) 3-Benzyl-7-(phenylsulfonyl)-9-oxa-3,7-diazabicyclo[3.3.1]nonane

A mixture of benzylamine (173.3 g, 1.62 mol), cis- and trans-2,6-bis(iodomethyl)-4-(phenylsulfonyl)morpholine (from step (i)(a) above; 275 g, 0.54 mol), and sodium hydrogencarbonate (182.2 g, 2.17 mol) in acetonitrile (13.5 L) was refluxed for 24 h. After this time, an aliquot was removed and diluted with ethyl acetate. HPLC analysis of this sample indicated that approximately 9% of the cis-isomer of the starting material remained unreacted. Reflux was continued for a further 6 h, but this gave no change in the percentage of unreacted starting material (as indicated by HPLC). The reaction was then allowed to cool to rt before the mixture was filtered and the filtrate concentrated in vacuo. The resulting crude product was partitioned between dichloromethane and 0.5 N NaOH solution. The organic layer was separated, washed with brine, dried (Na$_2$SO$_4$), filtered and then concentrated in vacuo to afford a mixture of oil and crystals. This mixture was slurried in toluene (300 mL) and the crystalline product collected by filtration. The filter cake of crystals was rinsed with cold toluene (100 mL), and then dried in a vacuum oven overnight (40° C., 13.3 Pa (0.1 mmHg)) to give 61.7 g (31.9% yield, 72.8% conversion of the cis-isomer) of the sub-title compound.

API MS: m/z=359[C$_{19}$H$_{22}$N$_2$O$_3$S+H]$^+$.

(iii) 3-Benzyl-9-oxa-3,7-diazabicyclo[3.3.1]nonane
dihydrochloride

To a mixture of anhydrous THF (1.1 L) and pellets of LiAlH$_4$ (48.5 g, 1.2 mol) under an inert atmosphere (N$_2$) was added 3-benzyl-7-(phenyl-sulfonyl)-9-oxa-3,7-diazabicyclo[3.3.1]nonane (from step (ii) above; 61.7 g, 0.17 mol) in portions over a 30 min period. The mixture was refluxed for 48 h before being cooled to −10° C. The cooled mixture was then treated sequentially (and cautiously) with water (45.8 mL), 15% NaOH solution (45.8 mL) and then water (137.4 mL) again. The resulting mixture was filtered through Celite® and the filtrate set aside. The inorganic salts from the filter cake were transferred to a beaker and stirred with ethyl acetate (1 L) for 30 min. This slurry was then filtered through Celite® again. The two filtrates were combined and then concentrated in vacuo to afford an oil (32.2 g). This oil was dissolved in methanol (120 mL) and treated with a solution of HCl in IPA (100 mL), after which the solution pH was checked for acidity. After standing for 24 h, a crop of crystals was collected by filtration and dried to a constant weight of 26.8 g. A second crop of crystals (7 g) was later obtained by crystallisation of the remaining crude product from IPA, giving a total yield of 33.8 g (68%) of the sub-title compound.

$^1$H NMR (CD$_3$OD+4 drops D$_2$O): δ 2.70 (br d, 2H), 3.09 (d, 2H), 3.47 (br s, 4H), 3.60 (s, 2H), 4.12 (br s, 2H), 7.30–7.45 (m, 5H).

API MS: m/z=219[C$_{13}$H$_{18}$N$_2$O+H]$^+$.

(iv) tert-Butyl 7-benzyl-9-oxa-3,7-diazabicyclo
[3.3.1]nonane-3-carboxylate

A mixture of water (400 mL), dichloromethane (400 mL), sodium hydrogencarbonate (40.3 g, 0.48 mol) and 3-benzyl-9-oxa-3,7-diaza-bicyclo[3.3.1]nonane dihydrochloride (from step (iii) above; 33.7 g, 0.12 mol) was stirred rapidly for 10 min before di-tert-butyl dicarbonate (27.8 g, 0.13 mol) was added in portions. After addition was complete, the reaction was stirred for a further 2 h. The organic layer was separated, dried (Na$_2$SO$_4$), filtered and concentrated in vacuo to afford 39.6 g of an off-white crystalline solid. This material was used directly in the next step without any further purification.

$^1$H NMR (CD$_3$OD): δ 1.5 (s, 9H), 2.42 (br t, 2H), 2.88 (d, 2H), 3.18–3.28 (m, 2H), 3.38 (d, 2H), 3.80 (br d, 2H), 4.00 (d, 2H), 7.16–7.38 (m, 5H).

(v) tert-Butyl 7-benzyl-9-oxa-3,7-diazabicyclo[3.3.1]nonane-3-carboxylate hydrochloride A solution of tert-butyl 7-benzyl-9-oxa-3,7-diazabicyclo[3.3.1]nonane-3-carboxylate (39.5 g, 0.12 mol) in ethyl acetate (200 mL) was cooled to −10° C. under an inert atmosphere ($N_2$). A solution of HCl in diethyl ether (1 M) was added over the course of 1 h, during which time a precipitate formed. After addition was complete, the resulting mixture was stirred for a further 1 h before the crystalline precipitate was collected by filtration and dried in a vacuum oven (40° C., 13.3 Pa (0.1 mmHg)). This gave 42.6 g (100% from the compound of step (iii) above) of the sub-title compound as an off-white crystalline material.

API MS: m/z=219$[C_{18}H_{26}N_2O_3—C_5H_9O_2]^+$.

(vi) tert-Butyl 9-oxa-3,7-diazabicyclo[3.3.1]nonane-3-carboxylate hydrochloride A mixture of tert-butyl 7-benzyl-9-oxa-3,7-diazabicyclo[3.3.1]nonane-3-carboxylate hydrochloride (from step (vi) above; 42.6 g, 0.12 mol), 10% palladium on carbon (2.5 g) and methanol (450 mL) was subjected to hydrogenation at atmospheric pressure. Once the reaction was complete (as indicated by tlc), the mixture was filtered and the filtrate concentrated in vacuo to yield 31.6 g of an off-white crystalline product. This crude product was dissolved in hot acetonitrile (450 mL), filtered and the filtrate diluted with ethyl acetate (450 mL). After being allowed to stand at rt for 6 h, the mixture was filtered to remove the first crop of crystallised product (19.8 g). The mother liquor was then concentrated to near dryness to give a residue that was dissolved in hot acetonitrile (150 mL). Ethyl acetate (150 mL) was added to this solution and the mixture allowed to stand at room temperature overnight. A second crop of crystalline product (8.7 g) was then collected by filtration, and was found to have an identical $^1$H NMR spectrum and melting point to the first crop. The combined yield of title compound was therefore 28.5 g (89%). m.p.=207–208° C.

Preparation B

4-{[(2S)-2-Hydroxy-3-(9-oxa-3,7-diazabicyclo[3.3.1]non-3-yl)propyl]-oxy}benzonitrile

(i) 4-[(2S)-Oxiranylmethoxy]benzonitrile

Potassium carbonate (414 g) and (R)-(−)-epichlorohydrin (800 mL) were added to a stirred solution of p-cyanophenol (238 g) in 2.0 L MeCN and the reaction mixture was refluxed under an inert atmosphere for 2 h. The hot solution was filtered and the filtrate concentrated, giving a clear oil which was crystallised from di-iso-propyl ether giving the product in 90% yield.

(ii) tert-Butyl 7-[(2S)-3-(4-cyanophenoxy)-2-hydroxypropyl]-9-oxa-3,7-diazabicyclo[3.3.1]nonane-3-carboxylate A mixture of tert-butyl 9-oxa-3,7-diazabicyclo[3.3.1]nonane-3-carboxylate (prepared in an analogous fashion to the compound of Preparation A(vi) above; 0.72 g, 3.2 mmol) and 4-[(2S)-oxiranylmethoxy]benzonitrile (from step (i) above; 0.56 g, 3.2 mmol) in IPA/water (11 mL of 10:1) was stirred at 60° C. for 18 h. The solvent was then evaporated to give 1.3 g (100%) of the sub-title compound, which was used in the next step without further purification.

(iii) 4-{[(2S)-2-Hydroxy-3-(9-oxa-3,7-diazabicyclo[3.3.1]non-3-yl)propyl]-oxy}benzonitrile A solution of tert-butyl 7-[(2S)-3-(4-cyanophenoxy)-2-hydroxypropyl]-9-oxa-3,7-diazabicyclo[3.3.1]nonane-3-carboxylate (from step (ii) above; 1.0 g, 2.47 mmol) in ethyl acetate (13 mL) was cooled to 0° C. Ethyl acetate (26 mL) saturated with gaseous HCl was added, and the mixture stirred for 4 h at rt. The solvent was removed in vacuo before MeCN (25 mL), water (1.3 mL) and $K_2CO_3$ (2.0 g) were added. The resulting mixture was stirred overnight before $CHCl_3$ was added, and the mixture filtered through Celite®. The filtrate was concentrated in vacuo to give 682 mg (91%) of the title compound.

Preparation C

4-{[3-(9-Oxa-3,7-diazabicyclo[3.3.1]non-3-yl)propyl]amino}benzonitrile

(i) 4-[(3-Hydroxypropyl)amino]benzonitrile

A mixture of 4-fluorobenzonitrile (12.0 g, 99.1 mmol) and 3-amino-1-propanol (59.6 g, 793 mmol) was stirred at 80° C. under an inert atmosphere for 3 hours before water (150 mL) was added. The mixture was allowed to cool to rt, and was then extracted with diethyl ether. The organic layer was separated, dried ($Na_2SO_4$), filtered and concentrated in vacuo to yield 17 g (97%) of the title compound as an oil that crystallised upon standing.

(ii) 3-(4-Cyanoanilino)propyl 4-methylbenzenesulfonate

A cooled (0° C.) solution of 4-[(3-hydroxypropyl)amino]benzonitrile (from step (i) above; 17 g, 96.5 mmol) in dry MeCN (195 mL) was treated with triethylamine (9.8 g, 96.5 mmol) and then p-toluenesulfonyl chloride (20.2 g, 106 mmol). The mixture was stirred at 0° C. for 90 minutes before being concentrated in vacuo. Water (200 mL) was added to the residue, and the aqueous solution was extracted with DCM. The organic phase was dried ($Na_2SO_4$), filtered and concentrated in vacuo. The resulting residue was purified by crystallisation from iso-propanol to yield 24.6 g (77%) of the sub-title compound.

(iii) tert-Butyl 7-[3-(4-cyanoanilino)propyl]-9-oxa-3,7-diazabicyclo[3.3.1]-nonane-3-carboxylate The hydrochloride salt of tert-butyl 9-oxa-3,7-diazabicyclo[3.3.1]nonane-3-carboxylate (from Preparation A(vi) above; 1.1 g, 4.15 mmol) was mixed with MeCN (46 mL), water (2.5 mL) and $K_2CO_3$ (3.5 g, 25 mmol). The mixture was stirred for 4 h before $CHCl_3$ was added and the mixture was filtered through Celite®. The filtrate was concentrated in vacuo to give 0.933 g of the free base. This was then mixed with 3-(4-cyanoanilino)propyl 4-methylbenzenesulfonate (from step (ii) above; 2.1 g, 6.2 mmol) and $K_2CO_3$ (0.86 g, 6.2 mmol) in MeCN (18 mL). The resulting mixture was stirred overnight at 60° C. before being concentrated in vacuo. The residue was treated with DCM (250 mL) and 1 M NaOH (50 mL). The layers were separated and the DCM layer washed twice with aqueous $NaHCO_3$, before being dried ($Na_2SO_4$) and concentrated in vacuo. The product was purified by flash chromatography, eluting with a gradient of toluene:ethyl acetate:triethylamine (2:1:0 to 1000:1000:1), to give 1.47 g (91%) of the sub-title compound.

(iv) 4-{[3-(9-Oxa-3,7-diazabicyclo[3.3.1]non-3-yl) propyl]amino}-benzonitrile The title compound was obtained in 96% yield according to the procedure described in Preparation B(iii) above, using tert-butyl 7-[3-(4-cyanoanilino)propyl]-9-oxa-3,7-diazabicyclo[3.3.1]nonane-3-carboxylate (from step (iii) above) in place of tert-butyl 7-[(2S)-3-(4-cyanophenoxy)-2-hydroxypropyl]-9-oxa-3,7-diazabicyclo[3.3.1]nonane-3-carboxylate.

Preparation D

4-[2-(9-Oxa-3,7-diazabicyclo[3.3.1]non-3-yl)ethoxy] benzonitrile

(i) 4-(2-Bromoethoxy)benzonitrile

A mixture of 4-cyanophenol (35.7 g, 0.3 mol), $K_2CO_3$ (41.4 g, 0.3 mol) and 1,2-dibromoethane (561 g, 3.0 mol) in MeCN (450 mL) was stirred under reflux overnight. The mixture was filtered and evaporated to give 30.2 g (45%) of the sub-title compound, which was used without further purification.

(ii) tert-Butyl 7-[2-(4-cyanophenoxy)ethyl]-9-oxa-3,7-diazabicyclo[3.3.1]-nonane-3-carboxylate The sub-title compound was prepared in 85% yield according to the procedure described in Preparation C(iii) above, using 4-(2-bromoethoxy)-benzonitrile (0.8 g, 3.5 mmol, 1.03 eq.) and triethylamine (1.5 eq.) in place of 3-(4-cyanoanilino)propyl 4-methylbenzenesulfonate, and $K_2CO_3$, respectively.

(iii) 4-[2-(9-Oxa-3,7-diazabicyclo[3.3.1]non-3-yl) ethoxy]benzonitrile

The title compound was obtained in 95% yield according to the procedure described in Preparation B(iii) above, using tert-butyl 7-[2-(4-cyanophenoxy)ethyl]-9-oxa-3,7-diazabicyclo[3.3.1]nonane-3-carboxylate (from step (ii) above) in place of tert-butyl 7-[(2S)-3-(4-cyanophenoxy)-2-hydroxypropyl]-9-oxa-3,7-diazabicyclo[3.3.1]nonane-3-carboxylate.

Preparation E

4-[3-(9-Oxa-3,7-diazabicyclo[3.3.1]non-3-yl)propoxy]benzonitrile

(i) 4-(3-Bromopropoxy)benzonitrile 1,3-Dibromopropane (1.02 L, 10 mol) was added to a stirred suspension of p-cyanophenol (238 g, 2 mol), $K_2CO_3$ (276.4 g, 2 mol) in MeCN (2.7 L). The reaction mixture was refluxed for 4 h, filtered and concentrated. The residue was recrystallised from iso-propyl ether to give the sub-title compound in a 69% yield.

(ii) tert-Butyl 7-[3-(4-cyanophenoxy)propyl]-9-oxa-3,7-diazabicyclo-[3.3.1]nonane-3-carboxylate The sub-title compound was prepared in 97% yield according to the procedure described in Preparation C(iii) above, using 4-(3-bromo-propoxy)benzonitrile (from step (i) above) in place of 3-(4-cyanoanilino)-propyl 4-methylbenzenesulfonate.

(iii) 4-[3-(9-Oxa-3,7-diazabicyclo[3.3.1]non-3-yl) propoxy]benzonitrile

The title compound was obtained in 90% yield according to the procedure described in Preparation B(iii) above, using tert-butyl 7-[3-(4-cyano-phenoxy)propyl]-9-oxa-3,7-diazabicyclo[3.3.1]nonane-3-carboxylate (from step (ii) above) in place of tert-butyl 7-[(2S)-3-(4-cyanophenoxy)-2-hydroxypropyl]-9-oxa-3,7-diazabicyclo[3.3 1]nonane-3-carboxylate.

Preparation F

4-[2-(9-Oxa-3,7-diazabicyclo[3.3.1]non-3-yl)ethoxy] isophthalonitrile

(i) 4-(2-Bromoethoxy)isophthalonitrile

The sub-title compound was prepared in 64% yield according to the procedure described in Preparation D(i) above, using 4-hydroxy-isophthalonitrile in place of 4-cyanophenol.

(ii) tert-Butyl 7-[2-(2,4-dicyanophenoxy)ethyl]-9-oxa-3,7-diazabicyclo-[3.3.1]nonane-3-carboxylate The sub-title compound was prepared in 62.7% yield according to the procedure described in Preparation C(iii) above, using 4-(2-bromoethoxy)-isophthalonitrile (from step (i) above) in place of 3-(4-cyanoanilino)propyl 4-methylbenzenesulfonate.

(iii) 4-[2-(9-Oxa-3,7-diazabicyclo[3.3.1]non-3-yl) ethoxy]isophthalonitrile The title compound was obtained according to the procedure described in Preparation B(iii) above, using tert-butyl 7-[2-(2,4-dicyanophenoxy)ethyl]-9-oxa-3,7-diazabicyclo [3.3.1]nonane-3-carboxylate (from step (ii) above) in place of tert-butyl 7-[(2S)-3-(4-cyanophenoxy)-2-hydroxypropyl]-9-oxa-3,7-diazabicyclo[3.3.1]nonane-3-carboxylate.

Preparation G

4-[4-(9-Oxa-3,7-diazabicyclo[3.3.1]non-3-yl)butyl] benzonitrile

(i) 4-(3-Butenyl)benzonitrile

Magnesium (4.2 g, 173 mmol) was activated by washing with dilute HCl, water and acetone and was then dried in vacuo. $ZnBr_2$ (37 g, 165 mmol) was sublimed under reduced pressure (approx. 5–20 mmHg) by gentle heating in a glovebox. The glovebox was used as it was extremely humid in the lab. Mg and $ZnBr_2$ were mixed in a dry 3-necked flask under $N_2$ and dry THF (30 mL) was added. 4-Bromo-1-butene (25.1 g, 186 mmol) dissolved in dry THF (175 mL) was added dropwise to the Mg/$ZnBr_2$ slurry and, during the addition, the reaction mixture turned greyish and then black. Some heat was also evolved (>40° C.). After complete addition, the mixture was heated to 50° C. overnight. 4-Bromobenzonitrile (30.5 g, 167 mmol) was co-evaporated with toluene twice and was then dissolved in dry THF (250 ml) together with $Pd(PPh_3)_4$ (5 g, 4.3 mmol, 2.5 mole). The slurry was added to the Grignard reagent and the reaction mixture was stirred at room temperature overnight. HCl (500 mL, 3 M) was added dropwise to the reaction mixture, and the resulting solution was extracted with ether (1000+

3×500 mL), the combined ether solutions were washed with NaHCO$_3$ (satd. 3×250 mL), dried, filtered and evaporated. The crude product (29.7 g) was subjected to Dry-Flash chromatography (diameter 12 cm, height 5 cm, heptane: EtOAc (99:1 to 90:10)) to give 21.2 g of the sub-title compound contaminated with 4-bromobenzonitrile (about 20%). This material was used in the next step.

(ii) 4-(4-Hydroxybutyl)benzonitrile 4-(3-Butenyl)benzonitrile (from step (i) above, 10.8 g, 69 mmol) was dissolved in dry THF (140 mL) and was cooled to 0° C. BH$_3$—Me$_2$S complex (20 mL, 2 M) was added dropwise over 45 minutes at 0° C. and, after 7 hours, water (70 mL) and NaBO$_3$—4H$_2$O (25 g) were added and the mixture was stirred overnight before dilution with ether (700 mL) and brine (satd., 250 mL). After separation, the aqueous phase was extracted with ether (2×200 mL) and the combined extracts were dried, filtered and evaporated to give crude sub-title compound. Purification by flash chromatography on SiO$_2$ (300 g) with heptane:EtOAc (3:1 to 1:1) gave the sub-title compound (6.99 g).

(iii) 4-(4-Cyanophenyl)butyl methanesulfonate

Methanesulfonyl chloride (2.32 mL, 30 mmol) was added to a cooled is (0° C.), stirred solution of 4-(4-hydroxybutyl)benzonitrile (from step (ii) above, 5.2 g, 29.7 mmol) and triethylamine (4.35 mL) in dichloromethane (50 mL). The resulting mixture was stirred for 4 h before water (150 mL) was added, and the organic layer separated, dried and concentrated to give the sub-title compound. This product was used directly in the next step without further purification.

(iv) tert-Butyl 7-[4-(4-Cyanophenyl)butyl]-9-oxa-3,7-diazabicyclo[3.3.1]-nonane-3-carboxylate The sub-title compound was prepared in 69.3% yield according to the procedure described in Preparation C(iii) above, using 4-(4-cyanophenyl)-butyl methanesulfonate (from step (iii) above) in place of 3-(4-cyano-anilino)propyl 4-methylbenzenesulfonate.

(v) 4-[4-(9-Oxa-3,7-diazabicyclo[3.3.1]non-3-yl)butyl]benzonitrile

The title compound was obtained in 88% yield according to the procedure described in Preparation B(iii) above, using tert-butyl 7-[4-(4-cyanophenyl)butyl]-9-oxa-3,7-diazabicyclo[3.3.1]nonane-3-carboxylate (from step (iv) above) in place of tert-butyl 7-[(2S)-3-(4-cyanophenoxy)-2-hydroxypropyl]-9-oxa-3,7-diazabicyclo[3.3.1]nonane-3-carboxylate.

Preparation H

4-[1-(3,4-Dimethoxyphenoxy)-4-(9-oxa-3,7-diazabicyclo[3.3.1]non-3-yl)butyl]benzonitrile (i) 4-[1-(3,4-Dimethoxyphenoxy)-3-butenyl]benzonitrile A cooled (0° C.) mixture of 4-(1-hydroxy-3-butenyl) benzonitrile (14.6 g, 84.3 mmol) and 3,4-dimethoxyphenol (19.5 g, 125.4 mmol) in toluene (500 mL) was treated with tributylphosphine (32.14 mL of 97% purity, 25.6 g, 126.4 mmol), followed by 1,1'-(azodicarbonyl)dipiperidine (31.8 g, 126.4 mmol). After addition was complete, the reaction mixture thickened and the temperature rose to 15° C. Additional toluene was added (500 mL), and the mixture stirred at rt overnight. The precipitate of tributylphosphine oxide was then removed by filtration and the filtrate concentrated in vacuo to give 65.8 g of crude product. This was purified by chromatography on silica gel, eluting with toluene:methanol (98:2), to yield 17.9 g of the sub-title compound.

(ii) 4-[1-(3,4-Dimethoxyphenoxy)-4-hydroxybutyl]benzonitrile

Borane-methyl sulfide complex (2 M in ether, 11 mL, 22 mmol) was added dropwise to a cooled (−5° C.) solution of 4-[1-(3,4-dimethoxy-phenoxy)-3-butenyl]benzonitrile (from step (i) above; 17.6 g, 56.8 mmol) in dry THF (15 mL) over a period of 15 minutes (during which time the reaction temperature rose to 0° C.). The resulting mixture was stirred at between 0 and 10°0 C. for 1.5 h, before being allowed to warm to rt. Stirring was continued for a further 3.5 h at this temperature before water (22 mL) and sodium perborate tetrahydrate (11 g, 66 mmol) were added. The biphasic mixture was stirred for 2 h at rt before the water layer was separated and extracted with ether. The combined organic layers were washed with brine, dried and concentrated in vacuo. The resulting residue was purified by chromatography on silica gel, eluting with IPA:ethyl acetate:heptane (5:25:70) to yield 14.5 g (77%) of the sub-title compound.

(iii) 4-(4-Cyanophenyl)-4-(3,4-dimethoxyphenoxy) butyl methanesulfonate

A solution of methanesulfonyl chloride (3.4 mL, 5.0 g, 44 mmol) in DCM (15 mL) was added slowly to a cooled (−5° C.) mixture of 4-[1-(3,4-dimethoxyphenoxy)-4-hydroxybutyl]benzonitrile (from step (ii) above; 11 g, 34 mmol) and triethylamine (7 mL, 5.2 g, 50.6 mmol) in DCM (50 mL), during which addition the temperature did not rise above 2° C. Stirring was continued at between 0 and 5° C. for a further 2 h before water was added. The resulting organic layer was separated, and washed with water, separated again and then dried to give the sub-title compound in 100% yield.

(iv) tert-Butyl 7-[4-(4-cyanophenyl)-4-(3,4-dimethoxyphenoxy)butyl]-9-oxa-3,7-diazabicyclo[3.3.1]nonane-3-carboxylate The sub-title compound was prepared in 82% yield according to the procedure described in Preparation C(iii) above, using 4-(4-cyanophenyl)-4-(3,4-dimethoxyphenoxy) butyl methanesulfonate (from step (iii) above) in place of 3-(4-cyanoanilino)propyl 4-methylbenzenesulfonate.

(v) 4-[1-(3,4-Dimethoxyphenoxy)-4-(9-oxa-3,7-diazabicyclo[3.3.1]non-3-yl)butyl]benzonitrile The title compound was obtained in quantitative yield according to the procedure described in Preparation B(iii) above, using tert-butyl 7-[4-(4-cyanophenyl)4-(3,4-dimethoxyphenoxy)butyl]-9-oxa-3,7-diazabicyclo-[3.3.1] nonane-3-carboxylate (from step (iv) above) in place of tert-butyl 7-[(2S)-3-(4-cyanophenoxy)-2-hydroxypropyl]-9-oxa-3,7-diazabicyclo-[3.3 1]nonane-3-carboxylate.

Preparation I

4-{[3-(9-Oxa-3,7-diazabicyclo[3.3.1]non-3-yl)propyl]sulfonyl}benzonitrile (i) 4-[(3-Bromopropyl)sulfanyl]benzonitrile A mixture of 4-cyanothiophenol (20.8 g, 154 mmol), 1,3-dibromopropane (155 g, 0.77 mol) and $K_2CO_3$ (21.3 g, 154 mmol) in MeCN (300 mL) was refluxed overnight. Filtration and evaporation of the solvent gave a brown oil that crystallised when treated with EtOH. The crystals were isolated by filtration to give the sub-title compound (24.5 g, 62%).

(ii) 4-[(3-Bromopropyl)sulfonyl]benzonitrile

3-Chloroperoxybenzoic acid (44.9 g of 70%, 182 mmol) was added slowly to a cooled (0° C.) solution of 4-[(3-bromopropyl)sulfanyl]benzonitrile (from step (i) above; 23.4 g, 91 mmol) in DCM (250 mL). The mixture was then stirred at rt overnight, and the resulting precipitate filtered off. The filtrate was concentrated in vacuo to give a residue that was shown (by NMR analysis) to contain 25% sulfoxide in addition to the desired product. The residue was redissolved in DCM (250 mL), additional 3-chloroperoxybenzoic acid (5.6 g of 70%, 23 mmol) added, and the mixture stirred for 30 min. Dimethylsulfoxide (20 mmol) was added to destroy excess mCPBA before the DCM solution was washed with aqueous $NaHCO_3$, separated, dried and concentrated in vacuo. This gave the sub-title compound in 76% yield.

(iii) tert-Butyl 7-{3-[(4-cyanophenyl)sulfonyl]propyl}-9-oxa-3,7-diazabicyclo[3.3.1]nonane-3-carboxylate The sub-title compound was prepared in 64% yield according to the procedure described in Preparation C(iii) above, using 4-[(3-bromo-propyl)sulfonyl]benzonitrile (from step (ii) above) in place of 3-(4-cyano-anilino)propyl 4-methylbenzenesulfonate.

(iv) 4-{[3-(9-Oxa-3,7-diazabicyclo[3.3.1]non-3-yl)propyl]sulfonyl}-benzonitrile

The title compound was obtained in 84% yield according to the procedure is described in Preparation B(iii) above, using tert-butyl 7-{3-[(4-cyanophenyl)sulfonyl]propyl}-9-oxa-3,7-diazabicyclo[3.3.1]nonane-3-carboxylate (from step (iii) above) in place of tert-butyl 7-[(2S)-3-(4-cyanophenoxy)-2-hydroxypropyl]-9-oxa-3,7-diazabicyclo[3.3.1]nonane-3-carboxylate.

Preparation J tert-Butyl (1S)-2-(4-cyanophenoxy)-1-(9-oxa-3,7-diazabicyclo[3.3.1]non-3-ylmethyl)ethylcarbamate (i) 4-(2-Oxiranylmethoxy)benzonitrile The sub-title compound was prepared in 75% yield according to the procedure described in Preparation B(i) above, using epichlorohydrin in place of (R)-(−)-epichlorohydrin.

(ii) 4-[(3-Amino-2-hydroxypropyl)oxy]benzonitrile 4-(Oxiranylmethoxy)benzonitrile (from step (i) above; 100 g, 0.57 mol) was added to a mixture of concentrated aqueous ammonium hydroxide (500 mL) and iso-propanol (300 mL). The resulting slurry was stirred at room temperature for 3 days. The reaction mixture was filtered to remove the insoluble by-product, and the filtrate was concentrated in vacuo to give a crude product, which was crystallised from acetonitrile to yield 50 g (46%) of the sub-title compound.

(iii) tert-Butyl 3-(4-cyanophenoxy)-2-hydroxypropylcarbamate

A cooled (0° C.) solution of 4-[(3-amino-2-hydroxypropyl)oxy]benzonitrile (from step (ii) above; 44.6 g, 0.23 mol) in $THF:H_2O$ (1.5 L of 1:1) was treated with di-tert-butyl dicarbonate (53 g, 0.24 mol). The mixture was stirred at rt overnight, after which NaCl was added and the resulting organic layer separated. The water layer was extracted with ether and the combined organics were dried and concentrated in vacuo. The resulting oil (70 g) was filtered through a plug of silica, and then crystallised from diethyl ether:di-iso-propyl ether to yield 50 g of the sub-title compound.

(iv) 2-[(tert-Butoxycarbonyl)amino]-1-[(4-cyanophenoxy)methyl]ethyl methanesulfonate Methanesulfonyl chloride (22.3 g 0.195 mol) was added over the course of 1.5 hours to a cooled (0° C.) solution of tert-butyl 3-(4-cyano-phenoxy)-2-hydroxypropylcarbamate (from step (iii) above; 51.2 g, 0.177 mol) and 4-(dimethylamino)pyridine (1.3 g, 10.6 mmol) in pyridine (250 mL), kept under an inert atmosphere. The reaction mixture was stirred for 2 h at rt before water and DCM were added. The organic layer was separated, washed with water, dried ($MgSO_4$) and concentrated in vacuo to yield 68.1 g (100%) of the sub-title compound.

(v) tert-Butyl 2-[(4-cyanophenoxy)methyl]-1-aziridinecarboxylate

A cooled (0° C.) solution of 2-[(tert-butoxycarbonyl)amino]-1-[(4-cyanophenoxy)methyl]ethyl methanesulfonate (from step (iv) above; 30.6 g, 82.6 mmol) and tetrabutylammonium hydrogensulfate (3 g, 8.8 mmol) in DCM (100 mL) was treated with 50 wt. % aqueous NaOH (60 mL) under an inert atmosphere. The resulting mixture was stirred, and the temperature was slowly allowed to rise to rt over for 4 h, and then extracted with ether. The organic layer was washed with water and concentrated in vacuo to give a residue that was purified by column chromatography (dichloromethane eluent). Crystallisation from diethyl ether: di-iso-propyl ether gave the sub-title compound in quantitative yield.

(vi) tert-Butyl (2S)-2-[(4-cyanophenoxy)methyl]-1-aziridinecarboxylate

The sub-title compound was prepared according to the procedures described in steps (i) to (v) above for the synthesis of tert-butyl 2-[(4-cyanophenoxy)methyl]-1-aziridinecarboxylate, but using (S)-(+)-epichlorohydrin in place of epichlorohydrin in step (i).

(vii) 3-Benzyl-7-(tert-butyl) 9-oxa-3,7-diazabicyclo[3.3.1]nonane-3,7-dicarboxylate The hydrochloride salt of tert-butyl 9-oxa-3,7-diazabicyclo[3.3.1]nonane-3-carboxylate (from Preparation A(vi) above; 2.17 g, 8.2 mmol) was dissolved in $CHCl_3$ (25 mL) and the mixture was cooled to 0° C. Triethylamine (2.1 g, 20.6 mmol) was added, followed by N-(benzyloxy-carbonyloxy)succinimide (2.24 g. 9.0 mmol), and the mixture stirred at rt for 24 h. The reaction mixture was washed with water (4×15 mL), before the organic layer was separated, dried (MgSO$_4$) and concentrated in vacuo. This gave the sub-title compound (4.4 g, containing some TEA) which was used in the next step without further purification.

(viii) Benzyl 9-oxa-3,7-diazabicyclo[3.3.1]nonane-3-carboxylate

The title compound was obtained in 55% yield according to the procedure described in Preparation B(iii) above, using 3-benzyl-7-(tert-butyl) 9-oxa-3,7-diazabicyclo[3.3.1]nonane-3,7-dicarboxylate (from step (vii) above) in place of tert-butyl 7-[(2S)-3-(4-cyanophenoxy)-2-hydroxypropyl]-9-oxa-3,7-diazabicyclo[3.3.1]nonane-3-carboxylate.

(ix) Benzyl 7-[(2S)-2-[(tert-butoxycarbonyl)amino]-3-(4-cyanophenoxy)-propyl]-9-oxa-3,7-diazabicyclo [3.3.1]nonane-3-carboxylate The sub-title compound was obtained in 71% yield according to the procedure described in Preparation B(ii) above, using benzyl 9-oxa-3,7-diazabicyclo[3.3.1]nonane-3-carboxylate (from step (viii) above) and tert-butyl (2S)-2-[(4-cyanophenoxy)methyl]-1-aziridinecarboxylate (from step (vi) above) in place of tert-butyl 9-oxa-3,7-diazabicyclo[3.3.1]nonane-3-carboxylate and 4-[(2S)-oxiranylmethoxy]benzonitrile, respectively.

(x) tert-Butyl (1S)-2-(4-cyanophenoxy)-1-(9-oxa-3,7-diazabicyclo[3.3.1]-non-3-ylmethyl)ethylcarbamate A solution of benzyl 7-[(2S)-2-[(tert-butoxycarbonyl)amino]-3-(4-cyanophenoxy)propyl]-9-oxa-3,7-diazabicyclo[3.3.1]nonane-3-carboxylate (from step (ix) above; 2.55 g, 4.7 mmol) in 95% ethanol (50 mL) was hydrogenated over 5% Pd/C (0.8 g) at 30 kPa. When the quantity of hydrogen calculated for complete reaction had been consumed, the reaction was stopped. The mixture was filtered through Celite®, and the filtrate concentrated in vacuo. The resulting residue was purified by chromatography on silica, eluting with CHCl$_3$:ammoniacal methanol (95:5), to yield the title compound 1.39 g (75%).

Preparation K

4-{[2-Hydroxy-3-(9-oxa-3,7-diazabicyclo[3.3.1]non-3-yl)propyl]oxy}-benzonitrile The title compound was prepared according to the method described in preparation B above, using epichlorohydrin in place of (R)-(−)-epichloro-hydrin in step (i).

Preparation L

2,6-Bis(hydroxymethyl)-4-(phenylsulfonyl)morpholine

(i) N,N-Bis(2-oxiranylmethyl)benzenesulfonamide

This reaction is very exothermic so care must be taken if the reaction is scaled up. Acetonitrile (400 mL) and (±)-epichlorohydrin (100 mL, 118.3 g, 0.78 mol) were added to benzenesulfonamide (50.0 g, 0.32 mol), followed by cesium carbonate (228 g, 0.70 mol). The mixture was heated at reflux for 15 hours with mechanical stirring. After cooling to room temperature water was added (250 mL) and the organic phase separated and concentrated under reduced pressure. The residual oil was chromatographed over silica (300 g), eluting with dichloromethane (1 L) and then dichloromethane:ethyl acetate (3 L of 19:1), to give the sub-title compound as an oil (39.4 g, 46%).

$^1$H NMR (400 MHz, CDCl$_3$): δ 2.55–2.65 (2H, m), 2.79 (2H, t, J 4.4), 3.10–3.22 (4H, m), 3.58–3.73 (2H, m), 7.50–7.56 (2H, m), 7.58–7.63 (1H, m), 7.83–7.87 (2H, m).

(ii) 2,6-Bis(hydroxymethyl)-4-(phenylsulfonyl)morpholine

Tetrahydrofuran (40 mL) was added to N,N-bis(2-oxiranylmethyl)benzene-sulfonamide (from step (i) (alternative A) above; 10 g, 37.1 mmol), followed by dilute sulfuric acid (10 mL of 1 M), and the mixture stirred for 6 days (reaction is complete within 1 day). Solid sodium chloride (3 g) and ethyl acetate (40 mL) were added, and the mixture stirred for 1 hour. The organic phase was separated and washed with aqueous ammonium chloride (10 mL of 10%). The organic phase was concentrated under reduced pressure before toluene was added (50 mL). The mixture was concentrated again to leave the title compound as a crude oil (10.65 g). This material was employed directly in subsequent reactions without any further purification.

Preparation M cis-2,6-Bis(hydroxymethyl)-4-(phenylsulfonyl)morpholine

(i) Chirally enriched N,N-bis(2-oxiranylmethyl)benzenesulfonamide

This reaction is very exothermic so care must be taken if the reaction is scaled up. Acetonitrile (100 mL) and (R)-(−)-epichlorohydrin (47 mL, 55.6 g, 0.60 mol) were added to benzenesulfonamide (20.0 g, 0.127 mol), followed by cesium carbonate (83 g, 0.255 mol). The mixture was heated at reflux for 6 hours with mechanical stirring and then was stirred overnight at room temperature. Water was added (100 mL), the organic phase separated and then concentrated under reduced pressure. The residual oil was chromatographed over silica, eluting with dichloromethane then dichloromethane:ethyl acetate (19:1), to give the sub-title compound as an oil (14.8 g, 43%).

(ii) cis-2,6-Bis(hydroxymethyl)-4-(phenylsulfonyl)morpholine

Tetrahydrofuran (60 mL) was added to chirally-enriched N,N-bis(2-oxiranylmethyl)benzenesulfonamide (from step (i) above; 14.8 g, 55 mmol), followed by dilute sulfuric acid (15 mL of 1 M), and the mixture stirred for 3 days. Solid sodium chloride (11 g) was added and the mixture stirred for 1 hour. The organic phase was separated and concentrated under reduced pressure to give crude product (22.4 g). The material was purified by column chromatography over silica, eluting with dichloromethane:ethanol (19:1), to give the title compound (4 g, 25%) and an impure fraction that was a 2:1 mixture of cis- and trans- isomers (8 g, 75%).

The cis-isomer is also ultimately formed as the major product if (S)-(+)-epichlorohydrin is used in step (i) in place of (R)-(−)-epichlorohydrin.

Preparation N

3,3-Dimethyl-1-(9-oxa-3,7-diazabicyclo[3.3.1]non-3-yl)-2-butanone

(i) N,N-Bis(2-oxiranylmethyl)benzenesulfonamide

The following is an alternative preparation to that described in Preparation L(i) above.

Water (2.5 L, 10 vol.) followed by epichlorohydrin (500 mL, 4 eq.) were added to benzenesulfonamide (250 g, 1 eq.). The reactants were heated to 40° C. Aqueous sodium hydroxide (130 g in 275 mL of water) was added such that the temperature of the reaction remained between 40° C. and 43° C. This took approximately 2 hours. (The rate of sodium hydroxide addition needs to be slower at the start of the addition than at the end in order to keep within the temperature range stated.) After the addition of sodium hydroxide was complete, the reaction was stirred at 40° C. for 2 hours, then at ambient temperature overnight. The excess epichlorohydrin was removed as a water azeotrope by vacuum distillation (ca. 40 mbar, internal temp 30° C.), until no more epichlorohydrin distilled. Dichloromethane (1L) was added and the mixture stirred rapidly for 15 minutes. The phases were allowed to separate (this took 10 minutes although totally clear phases are obtained after standing overnight). The phases were separated and the dichloromethane solution used in the subsequent step below.

$^1$H NMR (400 MHz, CDCl$_3$): δ 2.55–2.65 (2H, m), 2.79 (2H, t, J 4.4), 3.10–3.22 (4H, m), 3.58–3.73 (2H, m), 7.50–7.56 (2H, m), 7.58–7.63 (1H, m), 7.83–7.87 (2H, m).

(ii) 5-Benzyl-3,7-dihydroxy-1-phenylsulfonyl-1,5-diazacyclooctane

IMS (2.5 L, 10 vol) was added to the dichloromethane solution from step (i) above. The solution was distilled until the internal temperature reached 70° C. Approximately 1250 mL of solvent was collected. More IMS (2.5 L, 10 vol) was added followed by benzylamine (120 mL, 0.7 eq.) in one portion (no exotherm seen), and the reaction was heated at reflux for 6 hours (no change from 2 hour sampling point). More benzylamine was added (15 mL) and the solution was heated for a further 2 hours. The IMS was distilled off (ca. 3.25 L) and toluene was added (2.5 L). More solvent was distilled (ca. 2.4 L) and then further toluene added (1 L). The head temperature was now 110° C. A further 250 mL of solvent was collected at 110° C. Theoretically, this left the product in ca. 2.4 L of toluene at 110° C. This solution was used in the next step.

$^1$H NMR (400 MHz, CDCl$_3$): δ 7.83–7.80 (4H, m, ArH), 7.63–7.51 (6H, m, ArH), 7.30–7.21 (10H, ArH), 3.89–3.80 (4H, m, CH(a)+CH(b)), 3.73 (2H, s, CH$_2$Ph(a)), 3.70 (2H, s, CH$_2$Ph(b)), 3.59 (2H, dd, CHHNSO$_2$Ar(a)), 3.54 (2H, dd, CHHNSO$_2$Ar(b)), 3.40 (2H, dd, CHHNSO$_2$Ar(b)), 3.23 (2H, dd, CHHNSO$_2$Ar(a)), 3.09–2.97 (4H, m, CHHNBn(a)+CHHNBn(b)), 2.83 (2H, dd, CHHNBn(b)), 2.71 (2H, dd, CHHNBn(a)).

(Data taken from purified material comprising a 1:1 mixture of trans- (a), and cis-diol (b))

(iii) 3-Benzyl-7-(phenylsulfonyl)-9-oxa-3,7-diazabicyclo[3.3.1]nonane

The following is an alternative preparation to that described in Preparation A(ii) above.

The toluene solution from the previous step (ii) above was cooled to 50° C. Anhydrous methanesulfonic acid (0.2 L) was added. This caused a temperature rise from 50° C. to 64° C. After 10 minutes, methanesulfonic acid was added (1 L) and the reaction heated to 110° C. for 5 hours. Toluene was then distilled from the reaction; 1.23 L was collected. (Note that the internal temperature should not be allowed higher than 110° C. at any stage otherwise the yield will be decreased.) The reaction was then cooled to 50° C. and a vacuum applied to remove the rest of the toluene. Heating to 110° C. and 650 mbar allowed a further 0.53 L to be removed. (If the toluene can be removed at a lower temperature and pressure then that is beneficial.) The reaction was then left to cool to 30° C. and deionised water (250 mL) was added. This caused the temperature to rise from 30° C. to 45° C. More water (2.15 L) was added over a total time of 30 minutes such that the temperature was less than 54° C. The solution was cooled to 30° C. and then dichloromethane (2 L) was added. With external cooling and rapid stirring, the reaction mixture was basified by adding aqueous sodium hydroxide (10 M, 2 L) at a rate that kept the internal temperature below 38° C. This took 80 minutes. The stirring was stopped and the phases separated in 3 minutes. The layers were partitioned. IMS (2 L) was added to the dichloromethane solution and distillation started. Solvent (2.44 L) was collected until the head temperature reached 70° C. Theoretically, this left the product in 1.56 L of IMS. The solution was then allowed to cool to ambient temperature overnight with slow stirring. The solid product that precipitated was filtered and washed with IMS (0.5 L) to give a fawn-coloured product that, on drying at 50° C., in vacuum, gave 50.8 g (8.9% over 3 steps). 20.0 g of this product was dissolved in acetonitrile (100 mL) at reflux to give a pale yellow solution. After cooling to ambient temperature, the crystals that formed were collected by filtration and washed with acetonitrile (100 mL). The product was dried in vacuo at 40° C. for 1 hour to give 17.5 g (87%) of sub-title compound.

$^1$H NMR (400 MHz, CDCl$_3$): δ 7.18–7.23 (10H, m), 3.86–3.84 (2H, m), 3.67 (2H, d), 3.46 (2H, s), 2.91 (2H, d), 2.85 (2H, dd), 2.56 (2H, dd).

(iv) 3-Benzyl-9-oxa-3,7-diazabicyclo[3.3.1]nonane×2 HCl

This is an alternative preparation to that described in Preparation A(iii) above.

Concentrated hydrobromic acid (1.2 L, 3 rel. vol.) was added to solid 3-benzyl-7-(phenylsulfonyl)-9-oxa-3,7-diazabicyclo[3.3.1]nonane (400 g, see step (iii) above) and the mixture was heated to reflux under a nitrogen atmosphere. The solid dissolved in the acid at 95° C. After heating the reaction for 8 hours, HPLC analysis showed that the reaction was complete. The contents were cooled to room temperature. Toluene (1.2 L, 3 rel. vol.) was added and the mixture stirred vigorously for 15 minutes. Stirring was stopped and the phases were partitioned. The toluene phase was discarded along with a small amount of interfacial material. The acidic phase was returned to the original reaction vessel and sodium hydroxide (10 M, 1.4 L, 3.5 rel. vol.) was added in one portion. The internal temperature rose from 30° C. to 80° C. The pH was checked to ensure it was >14. Toluene (1.6 L, 4 rel. vol.) was added and the temperature fell from 80° C. to 60° C. After vigorous stirring for 30 minutes, the phases were partitioned. The aqueous layer was discarded along with a small amount of interfacial material. The toluene phase was returned to the original reaction vessel, and 2-propanol (4 L, 10 rel. vol.) was added. The temperature was adjusted to between 40° C. and 45° C. Concentrated hydrochloric acid (200 ml) was added over 45 minutes such that the temperature remained at between 40° C. and 45° C. A white precipitate formed. The mixture was stirred for 30 minutes and then cooled to 7° C. The product was collected by filtration, washed with 2-propanol (0.8 L, 2 rel vol.), dried by suction and then further dried in a vacuum oven at 40° C. Yield=297 g (91%).

$^1$H NMR (CD$_3$OD+4 drops D$_2$O): δ 2.70 (br d, 2H), 3.09 (d, 2H), 3.47 (br s, 4H), 3.60 (s, 2H), 4.12 (br s, 2H), 7.30–7.45 (m, 5H). API MS: m/z=219[C$_{13}$H$_{18}$N$_2$O+H]$^+$.

(v) 3,3-Dimethyl-1-[9-oxa-7-(phenylmethyl)-3,7-diazabicyclo[3.3.1]non-3-yl]-2-butanone Water (500 mL, 5 vol.) followed by 1-chloropinacolone (45.8 mL, 1 eq.) were added to sodium bicarbonate (114.2 g, 4 eq.). A solution of 3-benzyl-9-oxa-3,7-diazabicyclo[3.3.1]nonane×2 HCl (100.0 g; see step (iv) above) in water (300 mL, 3 vol.) was added slowly, so that the evolution of carbon dioxide was controlled (20 mins.). The reaction mixture was heated at 65 to 70° C. for 4 hours. After cooling to ambient temperature, dichloromethane (400 mL, 4 vol.) was added and, after stirring for 15 minutes, the phases were separated. The aqueous phase was washed with dichloromethane (400 mL, 4 vol.) and the organic extracts combined. The solution was distilled and solvent collected (550 mL). Ethanol (1 L) was added and the distillation continued. Further solvent was collected (600 mL). Ethanol (1 L) was added and the distillation continued. Further solvent was collected (500 mL) (the head temperature was now 77° C.). This solution (theoretically containing 1150 mL of ethanol) was used directly in the next step.

$^1$H NMR (400 MHz, CDCl$_3$): δ 1.21 (9H, s), 2.01–2.59 (2H, m), 2.61–2.65 (2H, m), 2.87–2.98 (4H, m), 3.30 (2H, s), 3.52 (2H, s), 3.87 (2H, br s), 7.26 (2H, d, J 7.6), 7.33 (1H, dd, J 7.6, 7.6), 7.47 (2H, d, J 7.6).

(vi) 3,3-Dimethyl-1-(9-oxa-3,7-diazabicyclo[3.3.1]non-3-yl)-2-butanone

Palladium on charcoal (44 g, 0.4 wt. eq. of 61% wet catalyst, Johnson Matthey Type 440L) was added to the ethanol solution from the previous step (v) above. The mixture was hydrogenated at 4 bar. The reaction was considered complete after 5 hours. The catalyst was removed by filtration and washed with ethanol (200 mL). The combined ethanol filtrates were used in Example 3 below. Solution assay gave 61.8 g of title product in ethanol (theoretically 1.35 L; measured 1.65 L). A portion of the product was isolated and purified. Analysis was performed on the purified product.

$^1$H NMR (300 MHz, CDCl$_3$): δ 1.17 (9H, s), 2.69 (2H, dt, J 11.4, 2.4), 2.93 (2H, d, J 10.8), 3.02 (2H, d, J 13.8), 3.26 (2H, s), 3.32 (2H, dt, J 14.1), 3.61 (2H, br s).

Preparation O 2-(4-Acetyl-1-piperazinyl)ethyl 1H-imidazole-1-carboxylate (i) 1-[4-(2-Hydroxyethyl)-1-piperazinyl]-1-ethanone A solution of 2-(1-piperazinyl)-1-ethanol (6.5 g, 0.05 mol) in DCM (5 mL) was treated with acetic acid anhydride (5.1 g, 0.05 mol), added dropwise. During addition, the reaction temperature rose from 22 to 60° C. The reaction mixture was evaporated several times with toluene to yield 5.6 g (65%) of the sub-title compound.

(ii) 2-(4-Acetyl-1-piperazinyl)ethyl 1H-imidazole-1-carboxylate

A solution of 1,1'-carbonyldiimidazole (5 g, 31 mmol) in DCM (200 mL) was treated with a solution of 1-[4-(2-hydroxyethyl)-1-piperazinyl]-1-ethanone (from step (i) above; 5 g, 29 mmol) in DCM (50 mL). The reaction mixture was stirred at rt overnight before water was added. The layers were separated, and the organic layer was washed with water, dried lo and concentrated in vacuo to yield 7.4 g (96%) of the title compound.

Preparation P

1-[4-(3-Bromopropyl)-1-piperazinyl]-1-ethanone

A mixture of 1-(1-piperazinyl)-1-ethanone (6.7 g, 0.052 mol), dibromopropane (330 mL, excess) and K$_2$CO$_3$ (10.2 g, 0.079 mol) was stirred at rt for 4 h. The mixture was washed with 4×100 mL of water, and the organic phase (diluted with DCM) was acidified with aqueous hydrobromic acid (7 mL of 62% HBr dissolved in 150 mL of water). The organic layer was separated and washed with water (2×50 mL). The combined water layers were extracted with ether, neutralised (to pH 7) with 13 mL of 10 M NaOH, and then extracted with DCM. The combined organic layers were dried and concentrated in vacuo to give 4.1 g (32%) of the title compound.

Preparation Q 3-(Ethylsulfonyl)propyl 4-methylbenzenesulfonate (i) 3-(Ethylsulfonyl)-1-propanol A solution of 3-(ethylthio)-1-propanol (13 g, 0.11 mol) in acetic acid (40 mL) was treated with H$_2$O$_2$ (30% in water, 12.2 g, 0.11 mol), added dropwise. The mixture was stirred for 2 h at rt, before being concentrated in vacuo. NMR analysis showed that the resulting residue consisted of 40% of the desired product and 60% of the corresponding O-acetate. The acetate was hydrolysed by dissolving the reaction mixture in 200 mL of methanol and adding 3 g of NaOH (dissolved in a small amount of water). This mixture was stirred overnight at rt, then concentrated in vacuo. The resulting crude product was dissolved in DCM, and insoluble material was filtered off. The DCM was removed by evaporation to give 13.4 g (88%) of the sub-title compound.

(ii) 3-(Ethylsulfonyl)propyl 4-methylbenzenesulfonate

A mixture of 3-(ethylsulfonyl)-1-propanol (from step (i) above; 13.4 g, 88 mmol) and p-toluenesulfonyl chloride (16.8 g, 88 mmol) in DCM (150 mL) was treated with TEA (13.4 g, 132 mmol), added dropwise. The resulting mixture was stirred at rt for 3 h before being washed with aqueous ammonium chloride solution. The organic layer was then separated, dried and concentrated in vacuo. The product was crystallised from ether containing a small amount of DCM to yield 17.9 g (66%) of the title compound.

Preparation R tert-Butyl 2-bromoethylcarbamate

Sodium bicarbonate (6.15 g, 0.073 mol) and di-t-butyl dicarbonate (11.18 g, 0.051 mol) were dissolved in a mixture of $H_2O$ (50 mL) and dichloromethane (150 mL), then cooled to 0° C. 2-Bromoethylamine hydrobromide (10.0 g, 0.049 mol) was added slowly as a solid, and the reaction was stirred overnight at 25° C. The dichloromethane layer was separated, washed with $H_2O$ (200 mL) and washed with a solution of potassium hydrogensulfate (150 mL, pH=3.5). The organic layer was dried ($Na_2SO_4$) and concentrated in vacuo. The crude oil was chromatographed on silica gel, eluting with dichloromethane to afford 7.87 g (72%) of the sub-title compound as a clear, colorless oil.

$^1$H NMR (300 MHz, $CDCl_3$) δ 4.98 (bs, 1H), 3.45–3.57 (m, 4H), 1.47 (s, 9H)

API-MS: (M+1-$C_5H_8O_2$) 126 m/z

Preparation S 2-(3,5-Dimethyl-1H-pyrazol-1-yl)ethyl 4-methylbenzenesulfonate

A cooled (0° C.) mixture of 2-(3,5-dimethyl-1H-pyrazol-1-yl)-1-ethanol (0.48 g, 3.4 mmol) and triethylamine (0.47 mL, 3.4 mmol) in MeCN (5 mL) was treated with 4-methylbenzenesulfonyl chloride (0.72 g, 3.8 mmol), after which the mixture was kept cool in a refrigerator for 2 days. The mixture was then concentrated in vacuo to give a residue which was purified by chromatography on silica gel, eluting with ethyl acetate:hexane (1:1), to give 0.46 g (46%) of the title compound.

Preparation T 4-(2-Bromoethoxy)phenyl tert-butyl ether

A solution of KOH (0.224 g, 4 mmol) in MeOH (3 mL) was added, over the course of 30 min, to a warmed (70° C.) mixture of 1,2-dibromoethane (3 g, 0.016 mol) and 4-(tert-butoxy)phenol (0.66 g, 0.004 mol). The mixture was stirred at 70° C. for 15 h before water and $CHCl_3$ were added. The layers were separated, the organic layer washed with 10% aqueous NaOH and then dried ($Na_2SO_4$) and concentrated in vacuo to give 0.32 g (28%) of the sub-title compound.

Preparation U

3-Benzyl-7-(phenylsulfonyl)-9-oxa-3,7-diazabicyclo [3.3.1]nonane via Chirally-Enriched 5-Benzyl-3,7-dihydroxy-1-phenylsufonyl-1,5-diaza-cyclooctane (i) Chirally-Enriched N,N-Bis(2-oxiranylmethyl)benzenesulfonamide The following is an alternative procedure to that described in Preparation M(i) above:

Water (100 mL, 10 vol) followed by (S)-epichlorohydrin (20 mL, 4 eq.) were added to benzenesulfonamide (10 g, 1 eq.). The reactants were heated to 40° C. Aqueous sodium hydroxide (10 M, 13 mL) was added over one hour, such that the temperature of the reaction mixture remained between 37° C. and 43° C. The reaction was then stirred at 40° C. for 2 hours and at ambient temperature overnight. The excess epichlorohydrin was removed as a water azeotrope by vacuum distillation (ca. 30 mbar, internal temp 30° C.) until no more epichlorohydrin distilled. Dichloromethane (200 mL) was added and the mixture was stirred rapidly for 15 minutes. The mixture was then separated and the dichloromethane layer was concentrated in vacuo to give a colourless oil, which was used in the next step without further purification.

$^1$H NMR (400 MHz, $CDCl_3$): δ 7.51–7.87 (m, 5H), 3.65–3.54 (4H, m), 3.24–3.08 (4H, m), 2.82–2.77 (1H, m), 2.61–2.55 (1H, m).

(ii) Chirally-Enriched 5-Benzyl-3,7-dihydroxy-1-phenylsufonyl-1,5-diaza-cyclooctane The crude product from step (i) above was dissolved in ethanol (200 mL) and treated at room temperature with benzylamine (6.9 mL, 1 equiv.) in one portion (no exotherm was observed). The mixture was heated to reflux for 4 hours, and was then stirred at ambient temperature overnight. The solvent was removed in vacuo to give a viscous, colourless oil which was used in the subsequent step without further purification.

$^1$H NMR (400 MHz, $CDCl_3$): δ 7.83–7.80 (2H, m, ArH), 7.63–7.51 (3H, m, ArH), 7.30–7.21 (5H, ArH), 3.89–3.80 (2H, m, CH), 3.73 (2H, s, $CH_2Ph$), 3.59 (2H, dd, $CHHNSO_2Ar$), 3.23 (2H, dd, $CHHNSO_2Ar$), 3.09–2.97 (2H, m, CHHNBn), 2.71 (2H, dd, CHHNBn).

(iii) 3-Benzyl-7-(phenylsulfonyl)-9-oxa-3,7-diazabicyclo[3.3.1]nonane

The crude product from step (ii) above was dissolved in warm toluene (150 mL) and treated with anhydrous methanesulfonic acid (50 mL). Toluene (105 mL) was removed from the mixture by distillation at reduced pressure (28 mbar). The remaining mixture was then heated to 110° C. for 6.5 h. The mixture was allowed to cool to 30° C. and the remaining toluene removed by distillation under reduced pressure (25 mbar). The mixture was cooled in an ice/water bath to 40° C. and then treated with water (100 mL), which caused the internal temperature to rise to 70° C. After cooling to 20° C. dichloromethane (80 mL) was added. The mixture was basified by the portionwise addition of aqueous sodium hydroxide solution (10 M, 80 mL), such that the internal temperature remained below 30° C. This took 20 minutes. The dicholoromethane layer was separated and evaporated nearly to dryness in vacuo. Methanol (50 mL) was added and the solvent was again removed in vacuo. The resulting solid was suspended in MeOH (50 mL) and filtered. The filter cake was washed with methanol (20 mL) and the resulting solid dried by air suction to give the title compound as a white crystalline solid (3.46 g, 15% over 3 steps).

The following intermediates were either commercially available or were prepared according to published methods:
ethyl isocyanate;
1-butanesulfonyl chloride;
1-chloropinacolone;
3,4-dimethoxyphenethyl methanesulfonate;
1-(chloromethyl)cyclopropane;
2-bromo-1-(2,3-dihydro-1,4-benzodioxin-6-yl)-1-ethanone;
5-(2-chloroethyl)-4-methyl-1,3-thiazole;
2-chloro-N-isopropylacetamide;
1-bromo-2-(2-methoxyethoxy)ethane;
4-fluorobenzyl bromide;
2-bromo-4'-methoxyacetophenone;
2-chloro-1-(4-fluorophenyl)-1-ethanone;
2-(bromomethyl)tetrahydro-2H-pyran;

1-bromo-3,3-dimethylbutane;
chloroacetone;
N,N-diethylchloroacetamide;
4-chloro-1-(4-fluorophenyl)-1-butanone;
4-(bromomethyl)benzonitrile;
1-(bromomethyl)-2,4-difluorobenzene;
4-(difluoromethoxy)benzyl bromide;
1-(2-bromoethyl)pyrrole;
1-(4-bromophenyl)-3-chloro-1-propanone;
2-bromo-1,1-difluoroethane;
1-(2-bromoethoxy)benzene;
2-(chloromethyl)imidazo[1,2-a]pyridine;
4-(2-chloroethyl)-1H-imidazole;
2-bromo-1-[4-(1-pyrrolidinyl)phenyl]-1-ethanone;
2-chloro-1-(4-hydroxyphenyl)-1-ethanone;
2-bromo-1-(4-methylphenyl)-1-ethanone;
2-bromo-1-(4-methoxyphenyl)-1-ethanone;
2-bromo-1-(2,3-dihydro-1,4-benzodioxin-6-yl)-1-ethanone;
6-(2-chloroacetyl)-2H-1,4-benzoxazin-3(4H)-one;
N-(tert-butyl)-N'-(2-chloroethyl)urea;
1-(chloromethyl)benzene; and
tert-butyl 2-(bromomethyl)-1-pyrrolidinecarboxylate.

Synthesis of Compounds of Formula I

EXAMPLE 1

4-{2-[7-(3,3-Dimethyl-2-oxobutyl)-9-oxa-3,7-diazabicyclo[3.3.1]non-3-yl]ethyl}benzonitrile

(i) tert-Butyl 7-(3,3-dimethyl-2-oxobutyl)-9-oxa-3,7-diazabicyclo[3.3.1]-nonane-3-carboxylate A mixture of tert-butyl 9-oxa-3,7-diazabicyclo[3.3.1]nonane-3-carboxylate hydrochloride (Preparation A; 0.26 g, 1.0 mmol) and $K_2CO_3$ (1.45 g, 10.5 mmol) in MeCN (8 mL) was treated with 1-chloropinacolone (0.216 g, 1.6 mmol), and the mixture stirred at 40° C. overnight. The following morning, the temperature was raised to 50° C. for 4 h before the solids were filtered off from the mixture and the filtrate concentrated in vacuo. The crude product was dissolved in DCM and the solution was added to an ion-exchange solid phase extraction plug (10 g CBA (carboxylic acid on silica support)). After 1 h, the plug was washed with DCM (15 mL), after which the product was finally eluted with dichloromethane:MeOH:TEA (90:5:5). The solvents were evaporated to give 0.276 g (85.5%) of the sub-title compound.

(ii) 3,3-Dimethyl-1-(9-oxa-3,7-diazabicyclo[3.3.1]non-3-yl)-2-butanone

The following is an alternative preparation to that described in Preparation N(v) above:

A solution of tert-butyl 7-(3,3-dimethyl-2-oxobutyl)-9-oxa-3,7-diaza-bicyclo[3.3.1]nonane-3-carboxylate (from step (i) above; 0.265 g, 0.812 mmol) in ethyl acetate (10 mL) was treated, at 0° C., with ethyl acetate saturated with gaseous hydrochloric acid. The mixture was stirred at 0° C. for 5 h, and then evaporated. Acetonitrile (15 mL) and $K_2CO_3$ (1 g, 7.2 mmol) were added, and the mixture was stirred overnight before being filtered and evaporated to yield 0.159 g (86%) of the sub-title compound.

(iii) 4-Cyanophenethyl methanesulfonate

Methanesulfonyl chloride (18.6 g, 164 mmol) was added to a stirred solution of 4-(2-hydroxyethyl)benzonitrile (20 g, 136 mmol) and triethylamine (20.6 g, 204 mmol) in DCM (200 mL) at 0° C. The reaction mixture was stirred at rt until the reaction was complete (as indicated by tlc). Water (200 mL) was added and the organic layer was separated, dried and concentrated to give the sub-title compound in a quantitative yield.

(iv) 4-{2-[7-(3,3-Dimethyl-2-oxobutyl)-9-oxa-3,7-diazabicyclo[3.3.1]non-3-yl]ethyl}benzonitrile A mixture of 3,3-dimethyl-1-(9-oxa-3,7-diazabicyclo[3.3.1]non-3-yl)-2-butanone (from step (ii) above; 56 mg, 0.25 mmol), TEA (0.35 mL, 2.5 mmol) and MeCN (2 mL) was treated with 4-cyanophenethyl methanesulfonate (see step (iii) above; 84 mg, 0.37 mmol). The resulting mixture was stirred at 50° C. for 24 h. The solvents were removed by evaporation, the crude product was dissolved in DCM and then the solution was added to an ion-exchange solid-phase extraction plug (2 g, CBA (carboxylic acid on silica support)). After 1 h, the plug was washed with DCM (15 mL), after which the product was finally eluted with DCM: MeOH:TEA (90:5:5), to give 84 mg (95%) of the title compound.

MS (ES): m/z=355.9 $(M)^+$.

EXAMPLE 2

7-[4-(4-Cyanophenyl)-4-(3,4-dimethoxyphenoxy) butyl]-N-ethyl-9-oxa-3,7-diazabicyclo[3.3.1]nonane-3-carboxamide A solution of ethyl isocyanate (18.8 mg, 0.25 mmol) in MeCN (2 mL) was added, together with $K_2CO_3$ (34.5 mg, 0.25 mmol), to a solution of 4-[1-(3,4-dimethoxyphenoxy)-4-(9-oxa-3,7-diazabicyclo[3.3.1]non-3-yl)-butyl]benzonitrile (Preparation H; 109.4 mg, 0.25 mmol) in chloroform (0.5 mL). The reaction mixture was stirred at rt for 4 days before being added to a solid phase extraction plug ($SiO_2$, 0.5 g). The plug was washed with $CHCl_3$:MeCN (2.5 mL of 80:20), and the product was finally eluted with $CHCl_3$:MeOH (3×2.5 mL of 95:5) to give the title compound.

MS (ES): m/z=508.3 $(M)^+$.

EXAMPLE 3

4-({3-[7-(3,3-Dimethyl-2-oxobutyl)-9-oxa-3,7-diazabicyclo[3.3.1]non-3-yl]propyl}amino)benzonitrile Alternative A A mixture of 4-{[3-(9-oxa-3,7-diazabicyclo[3.3.1]non-3-yl)propyl]amino}-benzonitrile (Preparation C; 5.73 g, 0.02 mol), $K_2CO_3$ (11.05 g, 0.08 mol) in MeCN (300 mL) was treated with 1-chloropinacolone (4.44 g, 0.032 mol). The mixture was stirred at 50° C. overnight before DCM was added and the mixture filtered. The filter cake was then washed with a mixture of DCM and MeCN before the solvent was evaporated from the filtrate. The resulting residue was purified by chromatography on silica, eluting with a gradient of ethyl acetate methanol:ammoniacal methanol (95:5:0 to 95:0:5), to give the title compound (5.8 g, 73.9%).

Alternative B—Preparation via Benzenesulfonic Acid Salt (i) 4-({3-[7-(3,3-Dimethyl-2-oxobutyl)-9-oxa-3,7-diazabicyclo[3.3.1]non-3-yl]propyl}amino)benzonitrile, benzenesulfonic acid salt monohydrate Potassium carbonate (56.6 g, 1.5 equiv) and 3-(4-cyanoanilino)propyl-4-methylbenzenesulfonate (see Preparation C(ii) above, 90.3 g, 1 equiv) were added to the ethanol solution of 3,3-dimethyl-1-(9-oxa-3,7-diazabicyclo[3.3.1]non-3-yl)-2-butanone (see Preparation N; 61.8 g from assay in 1.65 L). The reaction was heated at 80° C. for 4 hours. An assay showed some reactant remained (8.3 g), so more 3-(4-cyanoanilino)propyl-4-methylbenzenesulfonate (12.2 g) was added, and the resultant was heated at 80° C. for 4 hours. Solvent (1.35 L) was distilled, then isopropyl acetate (2.5 L) added. Solvent (2.51 L) was removed. Isopropyl acetate (2.5 L) was added. Solvent (0.725 L) was removed. The internal temperature was now at 88° C. Solvent (0.825 L) was removed, leaving the product as an isopropylacetate solution (theoretically in 2.04 L). After cooling to 34° C., water (0.5 L) was added. There was a black suspension, possibly of Pd, in the mixture. The pH of the aqueous phase was 11. Sodium hydroxide (1 M, 0.31 L) was added, so that the temperature was less than 25° C., and the mixture was stirred vigourously for 5 minutes. The pH of the aqueous phase was 12. The phases were separated and the aqueous phase discarded. More water (0.5 L) was added, and the phases were separated. The aqueous phase was discarded. The remaining ester solution was filtered to remove suspended particles, and the filtrate was then made up to exactly 2 L. The solution was then split into 2×1 L portions.

(In order to avoid producing sub-title product comprising a high palladium content, the following treatment may be performed: Deloxan® resin (12.5 g, 25 wt %) was added to the solution of the free base (1 L), and the mixture heated at reflux with vigorous stirring for 5 hours. The solution was then cooled to room temperature, and was stirred for 2 days. The resin was removed by filtration.)

An assay was performed to calculate the required amount of benzenesulfonic acid, to make the benzenesulfonate salt.

A solution of benzenesulfonic acid (20.04 g, 1 eq., assuming acid was pure monohydrate) in isopropyl acetate (200 mL) was added over 5 minutes (better to add slower if possible) with vigorous stirring to the solution of the free base (1 L) and a pale yellow precipitate formed. The temperature rose from 18° C. to 22° C. After 10 minutes, the mixture was cooled to 10° C. and the product collected by filtration. The product was washed with isopropyl acetate (250 mL), sucked dry on the filter then dried under vacuum at 40° C. for 2 days to give 59.0 g (61% from 3-benzyl-9-oxa-3,7-diazabicyclo[3.3.1]nonane×2HCl).

(The crude benzenesulfonate salt was alternatively prepared by the addition of a 70% (w/w) aqueous solution of benzenesulfonic acid to an ethanolic solution of the free base.)

The crude sub-title product is isolated as a monohydrate. Ethanol (500 mL) and water (250 mL) were added to crude sub-title compound (50.0 g). The solution was heated to 75° C. Material was all dissolved at 55° C. The solution was held at 75° C. for 5 minutes, then cooled to 5° C. over 1 hour. Precipitation started at 18° C. The cold solution was filtered and the filtrate washed with ethanol:water (2:1; 150 mL), sucked dry on the filter, and then dried in vacuo at 40° C. to give pure sub-title product (41.2 g, 82%).

(This recrystallisation may be carried out with greater volumes of solvent if necessary to fit the reaction vessels e.g. EtOH:water 2:1, 45 vol. (gave 62% recovery) EtOH:water 6:1, 35 vol. (gave 70% recovery).)

The sub-title product was isolated as the monohydrate following the rescrystallisation (as determined by single crystal X-ray diffraction).

(ii) 4-({3-[7-(3,3-Dimethyl-2-oxobutyl)-9-oxa-3,7-diazabicyclo[3.3.1]non-3-yl]propyl}amino)benzonitrile Crude benzenesulfonate salt (50.0 g, 1.0 equiv, from step (i) above) was added to aqueous sodium hydroxide (1M, 500 mL) washing in with dichloromethane (1.0 L, 20 vol). The combined mixture was stirred for 15 minutes. The layers were then separated and a small amount of interfacial material was left with the upper aqueous layer. Ethanol (500 mL, 10 vol) was added to the dichloromethane solution and then solvent was removed by distillation (1.25 L). The still head temperature was now at 78° C. The solution was allowed to cool to below reflux and ethanol (250 mL, 5 vol.) was added. Solvent was removed (250 mL). This warm solution was diluted with ethanol to 890 mL, 17.8 vol. (25 vol. assuming 100% conversion to free base). After heating to reflux the solution was cooled slowly. At 5° C. a seed of title compound was added. Crystallisation began and the mixture was stirred at 5° C. for 30 minutes. The product was collected by filtration and washed with ethanol (2×50 mL, 2×1 vol.). The product was then dried in a vacuum oven at 40° C. for 60 hours to give an off-white powder (26.3 g; 74%).

$^1$H NMR (400 MHz, CDCl$_3$): δ 7.86–7.82 (2H, m), 7.39–7.32 (3H. m), 7.30–7.26 (2H, m), 6.47 (2H, m), 4.11–4.07 (4H, m), 3.70 (2H, s), 3.36–3.33 (4H, m), 3.26 (2H, t), 3.12 (2H, d), 2.90 (2H, d), 2.28–2.21 (2H, m), 1.06 (9H, s).

$^{13}$C NMR (CDCl$_3$): δ 24.07, 26.38, 41.52, 43.52, 56.17, 56.47, 63.17, 68.46, 96.61, 111.64, 121.03, 133.43.

MS (ES): m/z=385.1 (M+H)$^+$.

EXAMPLE 4

4-{3-[7-(4-Fluorobenzyl)-9-oxa-3,7-diazabicyclo[3.3.1]non-3-yl]-2-hydroxypropoxy}benzonitrile A solution of 4-fluorobenzyl bromide (14.17 mg, 0.075 mmol) in DCM (0.5 mL) of was added, together with TEA (20 mg, 0.2 mmol) to a solution of 4-{[2-hydroxy-3-(9-oxa-3,7-diazabicyclo[3.3.1]non-3-yl)-propyl]oxy}benzonitrile (Preparation K; 15.2 mg, 0.05 mmol) in MeCN (0.5 mL). The mixture was stirred at 50° C. for 4 days before being concentrated in vacuo. The resulting residue was dissolved in CHCl$_3$ and added to a solid-phase extraction plug (CBA, 0.4 g). The plug was washed with CHCl$_3$ (4×0.3 mL), and the product was finally eluted with CHCl$_3$:MeOH:TEA (5×0.3 mL of 8:1:1) to give the title compound.

MS (ES): m/z=412.5 (M+H)$^+$.

EXAMPLE 5

4-(2-{7-[2-(4-Methoxyphenyl)-2-oxoethyl]-9-oxa-3,7-diazabicyclo[3.3.1]-non 3-yl}ethoxy)benzonitrile A mixture of 4-[2-(9-oxa-3,7-diazabicyclo[3.3.1]non-3-yl)ethoxy]benzonitrile (Preparation D; 68.3 mg, 0.25 mmol), 2-bromo-4'-methoxyaceto-phenone (68.7 mg, 0.3 mmol) and TEA (37.94 mg, 0.37 mmol) in DMF (2.5 mL) was stirred at rt for 2 days, and then (as reaction was found to be incomplete) at 50° C. for 24 h. The solvent was evaporated and the residue dissolved in a mixture of MeCN (2.5 mL) and H$_2$O (0.13 mL). Potassium carbonate (100 mg, 0.72 mmol) was added, and the mixture was stirred overnight at rt. The mixture was then filtered and the filtrate concentrated in vacuo. The resulting crude product was dissolved in DCM (2 mL), which solution was added to an ion-exchange solid-phase extraction plug (CBA, 2 g). After 80 min, the product was eluted with DCM:MeCN (4:1) and then with DCM:MeOH:TEA (8:1:1), to give an impure material. This material was purified on a silica plug, eluting with CHCl$_3$ (2 mL), CHCl$_3$:CH$_3$CN (3×2.5 mL of 4:1), and then with CHCl$_3$:MeOH (10:1), to give 71.5 mg (67.9%) of the title compound.

MS (ES): m/z=422.4 (M+H)$^+$.

$^{13}$C NMR (CDCl$_3$): δ 55.47, 55.89, 56.27, 57.17, 66.57, 66.81, 67.41, 102.99, 113.57, 115.73, 119.29, 131.56, 134.32, 162.09, 163.21, 196.25.

EXAMPLE 6

4-[((2S)-2-Amino-3-{7-[2-(1H-pyrrol-1-yl)ethyl]-9-oxa-3,7-diazabicyclo-[3.3.1]non-3-yl}propyl)oxy]benzonitrile A mixture of tert-butyl (1S)-2-(4-cyanophenoxy)-1-(9-oxa-3,7-diaza-bicyclo[3.3.1]non-3-ylmethyl)ethylcarbamate (Preparation J; 100.62 mg, 0.25 mmol), 1-(2-bromoethyl)pyrrole (52.21 mg, 0.30 mmol) and TEA (37.9 mg, 0.375 mmol) in DMF (2.5 mL) was stirred at rt for 2 days and then at 50° C. for 1 day. The solvent was evaporated and the resulting residue dissolved in ethyl acetate (0.5 mL). Ethyl acetate saturated with gaseous hydrochloric acid (2 mL) was added, and the reaction mixture stirred for 1.5 h at rt. The solvent was evaporated and the resulting residue dissolved in a mixture of MeCN (2.5 mL) and H$_2$O (0.13 mL). Potassium carbonate (100 mg, 0.72 mmol) was added, and the mixture stirred overnight at rt. The mixture was filtered and the filtrate concentrated in vacuo. The resulting crude product was dissolved in DCM (2 mL), which solution was added to a ion-exchange solid-phase extraction plug (CBA, 2 g). After 80 min, the product was eluted with DCM:MeCN (4×2 mL of 4:1), followed by DCM:MeOH:TEA (8:1:1), to give 89.7 mg (90.7%) of the title compound.

MS (ES): m/z=396.0 (M)$^+$.

EXAMPLE 7 tert-Butyl 2-{7-[3-(4-cyanoanilino)propyl]-9-oxa-3,7-diazabicyclo[3.3.1]-non-3-yl}ethylcarbamate To a solution of tert-butyl 2-bromoethylcarbamate (4.21 g, 0.019 mol; see Preparation R above) in DMF (65 mL) was added 4-{[3-(9-oxa-3,7-diazabicyclo[3.3.1]non-3-yl)propyl]amino}benzonitrile (see Preparation C above, 4.48 g, 0.016 mol) and triethylamine (3.27 mL, 0.024 mol). The mixture was stirred overnight at 35° C. and then concentrated in vacuo. The residue was dissolved in dichloromethane (80 mL) and washed with saturated sodium chloride. The aqueous layer was extracted with dichloromethane (1×150 mL). The combined organic extracts were dried (Na$_2$SO$_4$) and concentrated in vacuo. The crude red-brown oil was chromatographed (×2) on silica gel eluting with chloroform:methanol:conc. NH$_4$OH (9:1:0.02) to afford 3.75 g (56%) of the title compound.

$^1$H NMR (300 MHz, CD$_3$OD) δ 7.37–7.40 (d, J=8.8 Hz, 2H), 6.64–6.67 (d, J=8.8 Hz, 2H), 3.94 (bs, 2H), 3.21–3.31 (m, 4H), 3.01 (bs, 4H), 2.47–2.59 (m, 8H), 1.90 (bs, 2H), 1.39 (s, 9H)

$^{13}$C NMR (75 MHz, CD$_3$OD) δ 158.5, 134.7, 121.9, 113.2, 97.7, 80.3, 69.2, 58.8, 58.1, 57.5, 57.3, 41.9, 38.3, 28.9, 26.2.

API-MS: (M +1)=430 m/z

EXAMPLE 8 tert-Butyl 2-{7-[4-(4-cyanophenyl)butyl]-9-oxa-3,7-diazabicyclo[3.3.1]-non-3-yl}ethylcarbamate Triethylamine (2.2 mL, 0.016 mol) and tert-butyl 2-bromoethylcarbamate (see Preparation R above, 2.83 g, 0.013 mol) were added to a solution of 4-[4-(9-oxa-3,7-diazabicyclo[3.3.1]non-3-yl)butyl]benzonitrile (see Preparation G above, 3.0 g, 0.011 mol) in DMF (50 mL). The mixture was stirred for 24 h at 54° C., cooled to 25° C., and concentrated in vacuo. The residue was dissolved in chloroform and washed with saturated sodium chloride. The aqueous layer was separated and extracted with chloroform (2×150 mL). The combined organic layers were dried (Na$_2$SO$_4$) and concentrated in vacuo. The resulting material was chromatographed on silica gel, eluting first with chloroform:acetonitrile:conc. ammonium hydroxide (9:1:0.02) until the higher R$_f$ impurities were removed. Then the eluent was switched to chloroform:methanol:conc. ammonium hydroxide (9:1:0.02). This afforded 2.76 g (61%) of the title compound.

$^1$H NMR (300 MHz, CD$_3$OD) δ 7.62–7.64 (d, J=8.1 Hz, 2H), 7.38–7.40 (d, J=8.1 Hz, 2H), 3.84 (s, 2H), 3.14–3.18 (t, J=6.0 Hz, 2H), 2.83–2.93 (m, 4H), 2.72–2.77 (t, J=6.9 Hz, 2H), 2.30–2.50 (m, 8H), 1.64–1.68 (m, 4H), 1.43 (s, 9H).

$^{13}$C NMR (75 MHz, CD$_3$OD) δ 158.4, 149.6, 133.4, 130.7, 120.1, 110.7, 79.9, 69.8, 61.1, 58.7, 57.7, 57.1, 38.0, 36.9, 30.2, 29.0, 26.7.

EXAMPLE 9 tert-Butyl 2-{7-[(2S)-3-(4-cyanophenoxy)-2-hydroxypropyl]-9-oxa-3,7-di-azabicyclo[3.3.1]non-3-yl}ethylcarbamate Triethylamine (8.56 mL, 0.061 mol) and tert-butyl 2-bromoethyl-carbamate (see Preparation R above, 11.0 g, 0.049 mol) were added to a solution of 4-{[(2S)-2-hydroxy-3-(9-oxa-3,7-diazabicyclo[3.3.1]non-3-yl)-propyl]oxy}benzonitrile (see preparation B above, 12.41 g, 0.038 mol) in DMF (100 mL). The mixture was stirred for 20 h at 40° C., then concentrated in vacuo. The residue was dissolved in chloroform (100 mL), and washed with saturated sodium chloride. The aqueous layer was separated and extracted with chloroform (2×150 mL). The combined organic layers were dried (Na$_2$SO$_4$) and concentrated in vacuo.

The crude brown oil was chromatographed (×2) on silica gel, eluting first with chloroform:methanol (9:1), then with chloroform:methanol:conc. ammonium hydroxide (9:1:0.05) to afford 4.13 g (24%) of the title compound.

$^1$H NMR (300 MHz, CD$_3$OD) δ 7.62–7.69 (d, J=8.0 Hz, 2H), 7.09–7.14 (d, J=8.0 Hz, 2H), 4.00–4.17 (m, 3H), 3.87 (s, 2H), 3.18–3.24 (m, 2H), 2.88–3.03 (m, 4H), 2.65–2.70 (m, 2H), 2.47–2.55 (m, 4H), 2.31–2.39 (m, 2H), 1.41 (s, 9H).

$^{13}$C NMR (75 MHz, CD$_3$OD) δ 163.9, 158.3, 135.3, 120.2, 116.7, 104.9, 80.0, 72.1, 70.1, 69.9, 67.0, 60.6, 60.2, 58.4, 57.8, 55.7, 38.31, 28.99.

API-MS: (M+1)=447 m/z.

EXAMPLE 10

4-(2-{7-[4-(4-Pyridinyl)butyl]-9-oxa-3,7-diazabicyclo[3.3.1]non-3-yl}-ethoxy)benzonitrile

(i) 4-(4-Chlorobutyl)pyridine

4-Methylpyridine (8.4 g, 90 mmol) and THF (40 mL) were mixed in dry glassware, flushed with nitrogen and cooled to −60° C. n-BuLi (1.6 M solution, 61.9 mL, 99 mmol) was added dropwise over 1.5 h. The temperature was not allowed to exceed −50° C. The mixture was then allowed to reach rt, THF (20 mL) was added and the mixture was then stirred at 45° C. for 2 h. Additional THF (20 mL) was added. This mixture was cooled to 0° C. and added dropwise through a cooled dropping funnel to a 65° C. solution of 3-bromo-1-chloropropane (14.9 g, 94.5 mmol) in THF (15 mL). The reaction mixture was slowly allowed to reach 0° C. overnight. Water (90 mL) was added, and the mixture was stirred for 10 min. The organic layer was separated and dried ($Na_2SO_4$) to give the sub-title compound in 97.6% yield.

(ii) 4-(2-{7-[4-(4-Pyridinyl)butyl]-9-oxa-3,7-diazabicyclo[3.3.1]non-3-yl}-ethoxy)benzonitrile 4-[2-(9-Oxa-3,7-diazabicyclo[3.3.1]non-3-yl)ethoxy]benzonitrile (0.80 g, 2.92 mmol, see preparation D above) was dissolved in MeCN (30 mL) and mixed with 4-(4-chlorobutyl)pyridine (0.74 g, 4.39 mmol, from step (i) above) and $K_2CO_3$ (1.62 g, 11.71 mmol). 1 drop of $Br_2$ was added and the mixture was refluxed for 24 h. The mixture was filtered and evaporated. Purification by chromatography on silica, eluting with DCM:4% MeOH (satd. with ammonia), gave 0.68 g (57.2%) of the title compound.

$^{13}C$ NMR ($CDCl_3$) δ 25.78, 27.82, 34.92, 56.28, 56.50, 57.63, 58.99, 66.57, 68.11, 103.94, 115.20, 119.07, 123.75, 133.88, 149.57, 151.35, 161.91.

EXAMPLE 11 tert-Butyl 2-{7-[4-(4-pyridinyl)butyl]-9-oxa-3,7-diazabicyclo[3.3.1]non-3-yl}ethylcarbamate

(i) tert-Butyl 7-[4-(4-pyridinyl)butyl]-9-oxa-3,7-diazabicyclo[3.3.1]-nonane-3-carboxylate tert-Butyl 9-oxa-3,7-diazabicyclo[3.3.1]nonane-3-carboxylate (1.35 g, 5.9 mmol, see Preparation A and Preparation C(iii) above) was mixed with 4-(4-chlorobutyl)pyridine (1.35 g, 7.37 mmol, see Example 10(i) above), $Br_2$ (0.094 g, 0.59 mmol) and $K_2CO_3$ (3.26 g, 23.6 mmol). The mixture was refluxed under argon for 3 days. The reaction mixture was filtered, evaporated and purified by chromatography (DCM, 2–5% MeOH) giving 0.97 g (44%) of the sub-title compound.

$^{13}C$ NMR ($CDCl_3$) δ 25.83, 27.78, 28.48, 35.09, 45.80, 47.16, 56.57, 57.42, 58.99, 67.47, 67.72, 79.00, 123.88, 149.60, 151.26, 154.49

(ii) 3-[4-(4-Pyridinyl)butyl]-9-oxa-3,7-diazabicyclo[3.3.1]nonane tert-Butyl 7-[4-(4-pyridinyl)butyl]-9-oxa-3,7-diazabicyclo[3.3.1]nonane-3-carboxylate (0.9 g, 2.5 mmol, from step (i) above) was dissolved in ethylacetate, and then treated with ethylacetate saturated with HCl at 0° C. The mixture was stirred for 1 h at 0° C., and then at rt overnight. The solvent was evaporated. $CH_3CN$ (100 mL) and water (2 mL) were added together with $K_2CO_3$ (3.22 g). The mixture was stirred overnight. Filtration and evaporation gave the sub-title compound in 94% yield.

(iii) tert-Butyl 2-{7-[4-(4-pyridinyl)butyl]-9-oxa-3,7-diazabicyclo[3.3.1]-non-3-yl}ethylcarbamate 3-[4-(4-Pyridinyl)butyl]-9-oxa-3,7-diazabicyclo[3.3.1]nonane (0.25 g, 0.96 mmol, from step (ii) above), tert-butyl 2-bromoethylcarbamate (0.26 g, 0.98 mmol, see Preparation R above) and $K_2CO_3$ (0.4 g, 2.9 mmol) were mixed in $CH_3CN$ (10 mL) and stirred at 50° C. overnight. The reaction mixture was filtered, evaporated and purified by chromatography on silica (DCM:6% MeOH (satd. with $NH_3$)). Additional purification by extraction with ether: $KHSO_4$, basification of the organic phase and extraction with DCM gave the title compound in 51% yield.

$^{13}C$ NMR ($CD_3OD$) δ 26.65, 28.86, 29.38, 36.02, 38.00, 56.93, 57.58, 58.47, 60.93, 69.85, 79.93, 125.65, 149.85, 154.43, 158.40.

EXAMPLE 12

The following compounds were prepared, from appropriate intermediates (such as those described hereinbefore), according to or by analogy with methods described herein and/or by standard solid or solution phase combinatorial chemistry techniques (mass spectra of the compounds, where recorded, are in brackets):

4-{3-[7-(3,3-dimethyl-2-oxobutyl)-9-oxa-3,7-diazabicyclo[3.3.1]non-3-yl]-2-hydroxypropoxy}benzonitrile (m/z=402.5);

4-{3-[7-(3,4-dimethoxyphenethyl)-9-oxa-3,7-diazabicyclo[3.3.1]non-3-yl]-2-hydroxypropoxy}benzonitrile (m/z=467.2);

4-{2-[7-(3,3-dimethyl-2-oxobutyl)-9-oxa-3,7-diazabicyclo[3.3.1]non-3-yl]-ethoxy}benzonitrile (m/z=371.2);

4-({3-[7-(butylsulfonyl)-9-oxa-3,7-diazabicyclo[3.3.1]non-3-yl]propyl}amino)benzonitrile (m/z=406.2);

4-({3-[7-(3,4-dimethoxyphenethyl)-9-oxa-3,7-diazabicyclo[3.3.1]non-3-yl]propyl}amino)benzonitrile (m/z=450.3);

4-[4-[7-(butylsulfonyl)-9-oxa-3,7-diazabicyclo[3.3.1]non-3-yl]-1-(3,4-dimethoxyphenoxy)butyl]benzonitrile (m/z=557.3);

4-{1-(3,4-dimethoxyphenoxy)-4-[7-(3,3-dimethyl-2-oxobutyl)-9-oxa-3,7-diazabicyclo[3.3.1]non-3-yl]butyl}benzonitrile (m/z=535.3);

4-[4-[7-(3,4-dimethoxyphenethyl)-9-oxa-3,7-diazabicyclo[3.3.1]non-3-yl]-1-(3,4-dimethoxyphenoxy)butyl]benzonitrile (m/z=601.3);

2-(4-acetyl-1-piperazinyl)ethyl 7-[3-(4-cyanophenoxy)-2-hydroxypropyl]-9-oxa-3,7-diazabicyclo[3.3.1]nonane-3-carboxylate (m/z=501.3);

7-[3-(4-cyanophenoxy)-2-hydroxypropyl]-N-ethyl-9-oxa-3,7-diazabicyclo[3.3.1]nonane-3-carboxamide (m/z=374.2);

4-{3-[7-(butylsulfonyl)-9-oxa-3,7-diazabicyclo[3.3.1]non-3-yl]-2-hydroxypropoxy}benzonitrile (m/z=423.4);

2-(4-acetyl-1-piperazinyl)ethyl 7-[2-(4-cyanophenoxy)ethyl]-9-oxa-3,7-diazabicyclo[3.3.1]nonane-3-carboxylate (m/z=471.2);

7-[2-(4-cyanophenoxy)ethyl]-N-ethyl-9-oxa-3,7-diazabicyclo[3.3.1]nonane-3-carboxamide (m/z=344.2);

4-{2-[7-(butylsulfonyl)-9-oxa-3,7-diazabicyclo[3.3.1]non-3-yl]ethoxy}benzonitrile (m/z=393.2);

4-{2-[7-(3,4-dimethoxyphenethyl)-9-oxa-3,7-diazabicyclo[3.3.1]non-3-yl]ethoxy}benzonitrile (m/z=437.2);

2-(4-acetyl-1-piperazinyl)ethyl 7-[3-(4-cyanoanilino)propyl]-9-oxa-3,7-diazabicyclo[3.3.1]nonane-3-carboxylate (m/z=484.3);

7-[3-(4-cyanoanilino)propyl]-N-ethyl-9-oxa-3,7-diazabicyclo[3.3.1]nonane-3-carboxamide (m/z=357.2);

2-(4-acetyl-1-piperazinyl)ethyl 7-[4-(4-cyanophenyl)-4-(3,4-dimethoxyphenoxy)butyl]-9-oxa-3,7-diazabicyclo[3.3.1]nonane-3-carboxylate (m/z=635.3);

4-{3-[7-(cyclopropylmethyl)-9-oxa-3,7-diazabicyclo[3.3.1]non-3-yl]-2-hydroxypropoxy}benzonitrile (m/z=358.5);

4-(3-{7-[2-(2,3-dihydro-1,4-benzodioxin-6-yl)-2-oxoethyl]-9-oxa-3,7-diazabicyclo[3.3.1]non-3-yl}-2-hydroxypropoxy)benzonitrile (m/z=480.5);

4-(3-{7-[3-(4-acetyl-1-piperazinyl)propyl]-9-oxa-3,7-diazabicyclo[3.3.1]non-3-yl}-2-hydroxypropoxy)benzonitrile (m/z=472.5);

2-{7-[3-(4-cyanophenoxy)-2-hydroxypropyl]-9-oxa-3,7-diazabicyclo[3.3.1]non-3-yl}-N-isopropylacetamide (m/z=403.5);

4-(3-{7-[3-(ethylsulfonyl)propyl]-9-oxa-3,7-diazabicyclo[3.3.1]non-3-yl}-2-hydroxypropoxy)benzonitrile (m/z=438.5);

4-(2-hydroxy-3-{7-[2-(2-methoxyethoxy)ethyl]-9-oxa-3,7-diazabicyclo[3.3.1]non-3-yl}propoxy)benzonitrile (m/z=406.5);

4-(2-hydroxy-3-{7-[2-(4-methoxyphenyl)-2-oxoethyl]-9-oxa-3,7-diazabicyclo[3.3.1]non-3-yl}propoxy)benzonitrile (m/z=452.5);

4-({3-[7-(cyclopropylmethyl)-9-oxa-3,7-diazabicyclo[3.3.1]non-3-yl]-propyl}amino)benzonitrile (m/z=341.5);

4-[(3-{7-[2-(2,3-dihydro-1,4-benzodioxin-6-yl)-2-oxoethyl]-9-oxa-3,7-diazabicyclo[3.3.1]non-3-yl}propyl)amino]benzonitrile (m/z=463.5);

4-[(3-{7-[2-(4-methyl-1,3-thiazol-5-yl)ethyl]-9-oxa-3,7-diazabicyclo[3.3.1]non-3-yl}propyl)amino]benzonitrile (m/z=412.5);

4-[(3-{7-[3-(4-acetyl-1-piperazinyl)propyl]-9-oxa-3,7-diazabicyclo[3.3.1]non-3-yl}propyl)amino]benzonitrile (m/z=455.6);

2-{7-[3-(4-cyanoanilino)propyl]-9-oxa-3,7-diazabicyclo[3.3.1]non-3-yl}-N-isopropylacetamide (m/z=386.5);

4-[(3-{7-[3-(ethylsulfonyl)propyl]-9-oxa-3,7-diazabicyclo[3.3.1]non-3-yl}propyl)amino]benzonitrile (m/z=421.5);

4-[(3-{7-[2-(2-methoxyethoxy)ethyl]-9-oxa-3,7-diazabicyclo[3.3.1]non-3-yl}propyl)amino]benzonitrile (m/z=389.5);

4-({3-[7-(4-fluorobenzyl)-9-oxa-3,7-diazabicyclo[3.3.1]non-3-yl]propyl}amino)benzonitrile (m/z=395.5);

4-[(3-{7-[2-(4-methoxyphenyl)-2-oxoethyl]-9-oxa-3,7-diazabicyclo[3.3.1]non-3-yl}propyl)amino]benzonitrile (m/z=435.5);

4-{2-[7-(cyclopropylmethyl)-9-oxa-3,7-diazabicyclo[3.3.1]non-3-yl]ethoxy}benzonitrile (m/z=328.4);

4-(2-{7-[2-(2,3-dihydro-1,4-benzodioxin-6-yl)-2-oxoethyl]-9-oxa-3,7-diazabicyclo[3.3.1]non-3-yl}ethoxy)benzonitrile (m/z=450.5);

4-(2-{7-[2-(4-methyl-1,3-thiazol-5-yl)ethyl]-9-oxa-3,7-diazabicyclo[3.3.1]non-3-yl}ethoxy)benzonitrile (m/z=399.5);

4-(2-{7-[3-(4-acetyl-1-piperazinyl)propyl]-9-oxa-3,7-diazabicyclo[3.3.1]non-3-yl}ethoxy)benzonitrile (m/z=442.5);

2-{7-[2-(4-cyanophenoxy)ethyl]-9-oxa-3,7-diazabicyclo[3.3.1]non-3-yl}-N-isopropylacetamide (m/z=373.5);

4-(2-{7-[3-(ethylsulfonyl)propyl]-9-oxa-3,7-diazabicyclo[3.3.1]non-3-yl}ethoxy)benzonitrile (m/z=408.5);

4-(2-{7-[2-(2-methoxyethoxy)ethyl]-9-oxa-3,7-diazabicyclo[3.3.1]non-3-yl}ethoxy)benzonitrile (m/z=376.5);

4-{2-[7-(4-fluorobenzyl)-9-oxa-3,7-diazabicyclo[3.3.1]non-3-yl]ethoxy}benzonitrile (m/z=382.5);

4-({3-[7-(3,3-dimethyl-2-oxobutyl)-9-oxa-3,7-diazabicyclo[3.3.1]non-3-yl]propyl}sulfonyl)benzonitrile (m/z=434.5);

4-({3-[7-(cyclopropylmethyl)-9-oxa-3,7-diazabicyclo[3.3.1]non-3-yl]propyl}sulfonyl)benzonitrile (m/z=390.5);

4-[(3-{7-[2-(2,3-dihydro-1,4-benzodioxin-6-yl)-2-oxoethyl]-9-oxa-3,7-diazabicyclo[3.3.1]non-3-yl}propyl)sulfonyl]benzonitrile (m/z=512.4);

4-[(3-{7-[2-(4-methyl-1,3-thiazol-5-yl)ethyl]-9-oxa-3,7-diazabicyclo[3.3.1]non-3-yl}propyl)sulfonyl]benzonitrile (m/z=461.4);

4-[(3-{7-[3-(4-acetyl-1-piperazinyl)propyl]-9-oxa-3,7-diazabicyclo[3.3.1]non-3-yl}propyl)sulfonyl]benzonitrile (m/z=504.5);

2-(7-{3-[(4-cyanophenyl)sulfonyl]propyl}-9-oxa-3,7-diazabicyclo[3.3.1]non-3-yl)-N-isopropylacetamide (m/z=435.5);

4-[(3-{7-[3-(ethylsulfonyl)propyl]-9-oxa-3,7-diazabicyclo[3.3.1]non-3-yl}propyl)sulfonyl]benzonitrile (m/z=470.4);

4-[(3-{7-[2-(2-methoxyethoxy)ethyl]-9-oxa-3,7-diazabicyclo[3.3.1]non-3-yl}propyl)sulfonyl]benzonitrile (m/z=438.5);

4-({3-[7-(4-fluorobenzyl)-9-oxa-3,7-diazabicyclo[3.3.1]non-3-yl]propyl}sulfonyl)benzonitrile (m/z=444.4);

4-[(3-{7-[2-(4-methoxyphenyl)-2-oxoethyl]-9-oxa-3,7-diazabicyclo[3.3.1]non-3-yl}propyl)sulfonyl]benzonitrile (m/z=484.4);

4-[(3-{7-[2-(4-fluorophenyl)-2-oxoethyl]-9-oxa-3,7-diazabicyclo[3.3.1]non-3-yl}propyl)amino]benzonitrile (m/z=423.4);

4-(2-{7-[2-(4-fluorophenyl)-2-oxoethyl]-9-oxa-3,7-diazabicyclo[3.3.1]non-3-yl}ethoxy)benzonitrile (m/z=410.4);

4-{2-[7-(tetrahydro-2H-pyran-2-ylmethyl)-9-oxa-3,7-diazabicyclo[3.3.1]non-3-yl]ethoxy}benzonitrile (m/z=372.4);

4-(3-{7-[2-(4-fluorophenyl)-2-oxoethyl]-9-oxa-3,7-diazabicyclo[3.3.1]non-3-yl}-2-hydroxypropoxy)benzonitrile (m/z=440.4);

4-{2-hydroxy-3-[7-(tetrahydro-2H-pyran-2-ylmethyl)-9-oxa-3,7-diazabicyclo[3.3.1]non-3-yl]propoxy}benzonitrile (m/z=402.4);

4-({3-[7-(2-fluoro-3,3-dimethylbutyl)-9-oxa-3,7-diazabicyclo[3.3.1]non-3-yl]propyl}amino)benzonitrile (m/z=389.3);

4-({3-[7-(2-hydroxy-3,3-dimethylbutyl)-9-oxa-3,7-diazabicyclo[3.3.1]non-3-yl]propyl}amino)benzonitrile (m/z=387.0);

4-({3-[7-(3,3-dimethylbutyl)-9-oxa-3,7-diazabicyclo[3.3.1]non-3-yl]propyl}amino)benzonitrile (m/z=371.01);

4-({3-[7-(2-oxopropyl)-9-oxa-3,7-diazabicyclo[3.3.1]non-3-yl]propyl}amino)benzonitrile (m/z=342.92);

4-(2-{7-[3-(4-cyanoanilino)propyl]-9-oxa-3,7-diazabicyclo[3.3.1]non-3-yl}ethoxy)benzonitrile (m/z=431.9);

4-(2-{7-[2-(4-cyanophenoxy)ethyl]-9-oxa-3,7-diazabicyclo[3.3.1]non-3-yl}ethoxy)benzonitrile (m/z=418.9);

4-{7-[2-(4-cyanophenoxy)ethyl]-9-oxa-3,7-diazabicyclo[3.3.1]non-3-yl}ethyl)benzonitrile (m/z=402.9);

4-{4-[7-(3,3-dimethyl-2-oxobutyl)-9-oxa-3,7-diazabicyclo[3.3.1]non-3-yl]butyl}benzonitrile (m/z=383.9);

4-{2-[7-(2-phenoxyethyl)-9-oxa-3,7-diazabicyclo[3.3.1]non-3-yl]ethoxy}benzonitrile (m/z=393.9);

2-{7-[2-(4-cyanophenoxy)ethyl]-9-oxa-3,7-diazabicyclo[3.3.1]non-3-yl}-N,N-diethylacetamide (m/z=387.0);

4-[(3-{7-[4-(4-fluorophenyl)-4-oxobutyl]-9-oxa-3,7-diazabicyclo[3.3.1]non-3-yl}propyl)amino]benzonitrile (m/z=450.9);

4-({7-[3-(4-cyanoanilino)propyl]-9-oxa-3,7-diazabicyclo[3.3.1]non-3-yl}methyl)benzonitrile (m/z=401.9);

4-{2-[7-(2,4-difluorobenzyl)-9-oxa-3,7-diazabicyclo[3.3.1]non-3-yl]ethoxy}benzonitrile (m/z=400.0);

4-[(3-{7-[4-(difluoromethoxy)benzyl]-9-oxa-3,7-diazabicyclo[3.3.1]non-3-yl}propyl)amino]benzonitrile (m/z=442.9);

4-[(3-{7-[2-(1H-pyrrol-1-yl)ethyl]-9-oxa-3,7-diazabicyclo[3.3.1]non-3-yl}propyl)amino]benzonitrile (m/z=379.9);

4-[(3-{7-[3-(4-bromophenyl)-3-oxopropyl]-9-oxa-3,7-diazabicyclo[3.3.1]non-3-yl}propyl)amino]benzonitrile (m/z=496.8);

4-{2-[7-(2,2-difluoroethyl)-9-oxa-3,7-diazabicyclo[3.3.1]non-3-yl]ethoxy}benzonitrile (m/z=337.8);

4-({3-[7-(2-phenoxyethyl)-9-oxa-3,7-diazabicyclo[3.3.1]non-3-yl]propyl}amino)benzonitrile (m/z=407.4);

4-(2-{7-[2-(1H-pyrrol-1-yl)ethyl]-9-oxa-3,7-diazabicyclo[3.3.1]non-3-yl}ethoxy)benzonitrile (m/z=367.4);

4-[((2S)-3-{7-[(2S)-3-(4-cyanophenoxy)-2-hydroxypropyl]-9-oxa-3,7-diazabicyclo[3.3.1]non-3-yl}-2-hydroxypropyl)oxy]benzonitrile;

4-[((2S)-2-hydroxy-3-{7-[2-(1H-pyrrol-1-yl)ethyl]-9-oxa-3,7-diazabicyclo[3.3.1]non-3-yl}propyl)oxy]benzonitrile (m/z=397.4);

4-{2-[7-(3,3-dimethyl-2-oxobutyl)-9-oxa-3,7-diazabicyclo[3.3.1]non-3-yl]ethoxy}isophthalonitrile (m/z=397.4);

4-(2-{7-[2-(4-methoxyphenyl)-2-oxoethyl]-9-oxa-3,7-diazabicyclo[3.3.1]non-3-yl}ethoxy)isophthalonitrile (m/z=447.4);

4-(2-{7-[2-(1H-pyrrol-1-yl)ethyl]-9-oxa-3,7-diazabicyclo[3.3.1]non-3-yl}ethoxy)isophthalonitrile (m/z=392.4);

tert-butyl 2-{7-[2-(2,4-dicyanophenoxy)ethyl]-9-oxa-3,7-diazabicyclo[3.3.1]non-3-yl}ethylcarbamate (m/z=442.4);

4-({(2S)-2-amino-3-[7-(3,3-dimethyl-2-oxobutyl)-9-oxa-3,7-diazabicyclo[3.3.1]non-3-yl]propyl}oxy)benzonitrile (m/z=401.0);

4-[((2S)-2-amino-3-{7-[2-(4-methoxyphenyl)-2-oxoethyl]-9-oxa-3,7-diazabicyclo[3.3.1]non-3-yl}propyl)oxy]benzonitrile (m/z=451.0);

4-{3-[7-(3,3-dimethyl-2-oxobutyl)-9-oxa-3,7-diazabicyclo[3.3.1]non-3-yl]propoxy}benzonitrile (m/z=386.4);

4-(3-{7-[2-(4-fluorophenyl)-2-oxoethyl]-9-oxa-3,7-diazabicyclo[3.3.1]non-3-yl}propoxy)benzonitrile (m/z=424.4);

4-(3-{7-[2-(1H-pyrrol-1-yl)ethyl]-9-oxa-3,7-diazabicyclo[3.3.1]non-3-yl}propoxy)benzonitrile (m/z=381.4);

4-(4-{7-[2-(1H-pyrrol-1-yl)ethyl]-9-oxa-3,7-diazabicyclo[3.3.1]non-3-yl}butyl)benzonitrile (m/z=379.4);

4-{[(2S)-3-(7-{2-[4-(tert-butoxy)phenoxy]ethyl}-9-oxa-3,7-diazabicyclo[3.3.1]non-3-yl)-2-hydroxypropyl]oxy}benzonitrile (m/z=496.6);

4-[((2S)-3-{7-[2-(3,5-dimethyl-1H-pyrazol-1-yl)ethyl]-9-oxa-3,7-diazabicyclo[3.3.1]non-3-yl}-2-hydroxypropyl)oxy]benzonitrile (m/z=426.5);

4-{3-[7-(imidazo[1,2-a]pyridin-2-ylmethyl)-9-oxa-3,7-diazabicyclo[3.3.1]non-3-yl]propoxy}benzonitrile (m/z=418.5);

4-{3-[7-(2-phenoxyethyl)-9-oxa-3,7-diazabicyclo[3.3.1]non-3-yl]propoxy}benzonitrile (m/z=408.5);

4-(3-{7-[2-(3,5-dimethyl-1H-pyrazol-1-yl)ethyl]-9-oxa-3,7-diazabicyclo[3.3.1]non-3-yl}propoxy)benzonitrile (m/z=410.5);

4-({3-[7-(imidazo[1,2-a]pyridin-2-ylmethyl)-9-oxa-3,7-diazabicyclo[3.3.1]non-3-yl]propyl}amino)benzonitrile (m/z=417.5);

4-({3-[7-(2,4-difluorobenzyl)-9-oxa-3,7-diazabicyclo[3.3.1]non-3-yl]propyl}amino)benzonitrile (m/z=413.5);

4-{[3-(7-{2-[4-(tert-butoxy)phenoxy]ethyl}-9-oxa-3,7-diazabicyclo[3.3.1]non-3-yl)propyl]amino}benzonitrile (m/z=479.6);

4-{2-[7-(imidazo[1,2-a]pyridin-2-ylmethyl)-9-oxa-3,7-diazabicyclo[3.3.1]non-3-yl]ethoxy}benzonitrile (m/z=404.5);

tert-butyl 2-{7-[2-(4-cyanophenoxy)ethyl]-9-oxa-3,7-diazabicyclo[3.3.1]non-3-yl}ethylcarbamate (m/z=417.5);

4-{[3-(7-{2-[4-(tert-butoxy)phenoxy]ethyl}-9-oxa-3,7-diazabicyclo[3.3.1]non-3-yl)propyl]sulfonyl}benzonitrile (m/z=528.5);

4-[(3-{7-[2-(3,5-dimethyl-1H-pyrazol-1-yl)ethyl]-9-oxa-3,7-diazabicyclo[3.3.1]non-3-yl}propyl)sulfonyl]benzonitrile (m/z=458.5);

4-({3-[7-(2,4-difluorobenzyl)-9-oxa-3,7-diazabicyclo[3.3.1]non-3-yl]propyl}sulfonyl)benzonitrile (m/z=462.0);

4-{2-[7-(imidazo[1,2-a]pyridin-2-ylmethyl)-9-oxa-3,7-diazabicyclo[3.3.1]non-3-yl]ethoxy}isophthalonitrile (m/z=429.0);

4-[2-(7-{2-[4-(tert-butoxy)phenoxy]ethyl}-9-oxa-3,7-diazabicyclo[3.3.1]non-3-yl)ethoxy]isophthalonitrile (m/z=491.6);

4-(2-{7-[2-(3,5-dimethyl-1H-pyrazol-1-yl)ethyl]-9-oxa-3,7-diazabicyclo[3.3.1]non-3-yl}ethoxy)isophthalonitrile (m/z=421.5);

4-(4-{7-[2-(1H-imidazole-4-yl)ethyl]-9-oxa-3,7-diazabicyclo[3.3.1]non-3-yl}butyl)benzonitrile (m/z=380.1);

4-{4-[7-(imidazo[1,2-a]pyridin-2-ylmethyl)-9-oxa-3,7-diazabicyclo[3.3.1]non-3-yl]butyl}benzonitrile (m/z=416.5);

4-{4-[7-(2-phenoxyethyl)-9-oxa-3,7-diazabicyclo[3.3.1]non-3-yl]butyl}benzonitrile (m/z=406.5);

4-(4-{7-[2-(3,5-dimethyl-1H-pyrazol-1-yl)ethyl]-9-oxa-3,7-diazabicyclo[3.3.1]non-3-yl}butyl)benzonitrile (m/z=408.6);

4-[3-(7-{2-oxo-2-[4-(1-pyrrolidinyl)phenyl]ethyl}-9-oxa-3,7-diazabicyclo[3.3.1]non-3-yl)propoxy]benzonitrile (m/z=475);

4-(3-{7-[2-(4-hydroxyphenyl)-2-oxoethyl]-9-oxa-3,7-diazabicyclo[3.3.1]non-3-yl}propoxy)benzonitrile (m/z=422);

4-(3-{7-[2-(4-methylphenyl)-2-oxoethyl]-9-oxa-3,7-diazabicyclo[3.3.1]non-3-yl}propoxy)benzonitrile (m/z=420);

4-(3-{7-[2-(4-methoxyphenyl)-2-oxoethyl]-9-oxa-3,7-diazabicyclo[3.3.1]non-3-yl}propoxy)benzonitrile (m/z=436);

4-(3-{7-[2-(2,3-dihydro-1,4-benzodioxin-6-yl)-2-oxoethyl]-9-oxa-3,7-diazabicyclo[3.3.1]non-3-yl}propoxy)benzonitrile (m/z=464);

4-(2-{7-[2-(2,6-dimethylphenoxy)-1-methylethyl]-9-oxa-3,7-diazabicyclo[3.3.1]non-3-yl}ethoxy)benzonitrile (m/z=436);

4-(3-{7-[2-oxo-2-(3-oxo-3,4-dihydro-2H-1,4-benzoxazin-6-yl)ethyl]-9-oxa-3,7-diazabicyclo[3.3.1]non-3-yl}propoxy)benzonitrile (m/z=477);

tert-butyl 2-{7-[3-(4-cyanophenoxy)propyl]-9-oxa-3,7-diazabicyclo[3.3.1]non-3-yl}ethylcarbamate (m/z=431);

N-(tert-butyl)-N'-(2-{7-[3 (4-cyanophenoxy)propyl]-9-oxa-3,7-diazabicyclo[3.3.1]non-3-yl}ethyl)urea (m/z=430);

tert-butyl 2-({7-[2-(4-cyanophenoxy)ethyl]-9-oxa-3,7-diazabicyclo[3.3.1]non-3-yl}methyl)-1-pyrrolidinecarboxylate (m/z=457);

4-{[3-(7-benzyl-9-oxa-3,7-diazabicyclo[3.3.1]non-3-yl)pro-pyl]amino}benzonitrile (m/z=377);

4-[(3-{7-[3-(4-cyanoanilino)propyl]-9-oxa-3,7-diazabicyclo [3.3.1]non-3-yl}propyl)amino]benzonitrile (m/z=445);

tert-butyl 2-{7-[2-(4-nitrophenoxy)ethyl]-9-oxa-3,7-diaz-abicyclo[3.3.1]non-3-yl}ethylcarbamate (m/z=437);

tert-butyl 2-[7-(2-{4-[(methylsulfonyl)amino] phenoxy}ethyl)-9-oxa-3,7-diazabicyclo[3.3.1]non-3-yl] ethylcarbamate;

tert-butyl 2-{7-[2-(4-aminophenoxy)ethyl]-9-oxa-3,7-diaz-abicyclo[3.3.1]non-3-yl}ethylcarbamate;

4-({3-[7-(phenylsulfonyl)-9-oxa-3,7-diazabicyclo[3.3.1] non-3-yl]propyl}amino)benzonitrile; and 4-({3-[7-(3,3-dimethyl-2-oxobutyl)-9-oxa-3,7-diazabicyclo [3.3.1]non-3-yl]propyl}amino)benzamide.

EXAMPLE 13

Title compounds of the above Examples were tested in Test A above and were found to exhibit $D_{10}$ values of more than 6.0.

Abbreviations

| | | |
|---|---|---|
| Ac | = | acetyl |
| API | = | atmospheric pressure ionisation (in relation to MS) |
| aq. | = | aqueous |
| br | = | broad (in relation to NMR) |
| Bt | = | benzotriazole |
| t-BuOH | = | tert-butanol |
| CI | = | chemical ionisation (in relation to MS) |
| mCPBA | = | meta-chloroperoxybenzoic acid |
| d | = | doublet (in relation to NMR) |
| DBU | = | diazabicyclo[5.4.0]undec-7-ene |
| DCM | = | dichloromethane |
| dd | = | doublet of doublets (in relation to NMR) |
| DMAP | = | 4-dimethylaminopyridine |
| DMF | = | N,N-dimethylformamide |
| DMSO | = | dimethylsulfoxide |
| EDC | = | 1-[3-(dimethylamino)propyl]-3-ethylcarbodiimide |
| Et | = | ethyl |
| EtOAc | = | ethyl acetate |
| eq. | = | equivalents |
| ES | = | electrospray (in relation to MS) |
| FAB | = | fast atom bombardment (in relation to MS) |
| h | = | hour(s) |
| HCl | = | hydrochloric acid |
| HEPES | = | 4-(2-hydroxyethyl)-1-piperazineethanesulfonic acid |
| HPLC | = | high performance liquid chromatography |
| IMS | = | industrial methylated spirits |
| IPA | = | iso-propyl alcohol (propan-2-ol) |
| m | = | multiplet (in relation to NMR) |
| Me | = | methyl |
| MeCN | = | acetonitrile |
| MeOH | = | methanol |
| min. | = | minute(s) |
| m.p. | = | melting point |
| MS | = | mass spectroscopy |
| NADPH | = | nicotinamide adenine dinucleotide phosphate, reduced form |
| OAc | = | acetate |
| Pd/C | = | palladium on carbon |
| q | = | quartet (in relation to NMR) |
| rt | = | room temperature |
| s | = | singlet (in relation to NMR) |
| t | = | triplet (in relation to NMR) |
| TEA | = | triethylamine |
| THF | = | tetrahydrofuran |
| tlc | = | thin layer chromatography |

Prefixes n-, s-, i-, t- and tert- have their usual meanings: normal, secondary, iso, and tertiary.

What is claimed is:

1. A process for the preparation of a compound of formula I

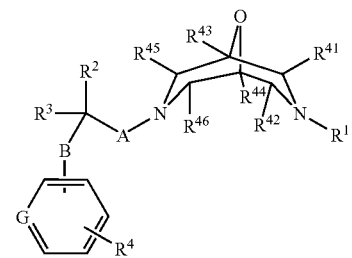

wherein $R^1$ represents $C_{1-12}$ alkyl which alkyl group is optionally substituted and—or terminated by one or more groups selected from halo, cyano, nitro, aryl, $Het^1$, —C(O)$R^{5a}$, —O$R^{5b}$, —N($R^6$)$R^{5c}$, —C(O)X$R^7$, —C(O)N($R^8$)$R^{5d}$, and —S(O)$_2R^9$, or $R^1$ represents —C(O)X$R^7$, —C(O)N($R^8$)$R^{5d}$ or —S(O)$_2R^9$;

$R^{5a}$ to $R^{5d}$ independently represent, at each occurrence, H, $C_{1-6}$ alkyl which alkyl group is optionally substituted and/or terminated by one or more substituents selected from —OH, halo, cyano, nitro, aryl and $Het^2$, aryl and $Het^3$, or $R^{5d}$, together with $R^8$, represents $C_{3-6}$ alkylene which alkylene group is optionally interrupted by an O atom and/or is optionally substituted by one or more $C_{1-3}$ alkyl groups;

$R^6$ represents H, $C_{1-6}$ alkyl which alkyl group is optionally substituted and/or terminated by one or more substituents selected from —OH, halo, cyano, nitro and aryl, aryl, —C(O)$R^{10a}$, —C(O)O$R^{10b}$ or —C(O)N(H)$R^{10c}$;

$R^{10a}$, $R^{10b}$ and $R^{10c}$ independently represent $C_{1-6}$ alkyl optionally substituted and/or terminated by one or more substituents selected from —OH, halo cyano, nitro and aryl, aryl, or $R^{10a}$ represents H;

$R^7$ represents $C_{1-12}$ alkyl which alkyl group is optionally substituted and/or terminated by one or more substituents selected from —OH, halo, cyano, nitro, aryl, $C_{1-6}$ alkoxy and $Het^4$;

$R^8$ represents H, $C_{1-12}$ alkyl, $C_{1-6}$ alkoxy which alkyl and alkoxy groups are optionally substituted and/or terminated by one or more substituents selected from —OH, halo, cyano, nitro, $C_{1-4}$ alkyl and $C_{1-4}$ alkoxy, —D-aryl, —D-aryloxy, —D-Het$^5$, —D—N(H)C(O)$R^{11a}$, —D—S(O)$_2R^{12a}$, —D—C(O)$R^{11b}$, —D—C(O)O$R^{12b}$, —D—C(O)N($R^{11c}$)$R^{11d}$, or $R^8$, together with $R^{5d}$, represents $C_{3-6}$ alkylene which alkylene group is optionally interrupted by an O atom and/or is optionally substituted by one or more $C_{1-3}$ alkyl groups;

$R^{11a}$ to $R^{11d}$ independently represent H, $C_{1-6}$ alkyl which alkyl group is optionally substituted and/or terminated by one or more substituents selected from —OH, halo, cyano, nitro and aryl, aryl, or $R^{11c}$ and $R^{11d}$ together represent $C_{3-6}$ alkylene;

$R^9$, $R^{12a}$ and $R^{12b}$ independently represent $C_{1-6}$ alkyl which alkyl group is optionally substituted and/or terminated by one or more substituents selected form —OH, halo, cyano, nitro and aryl, or aryl;

D represents a direct bond or $C_{1-6}$ alkylene;

X represents O or S;

$R^2$ represents H, halo, $C_{1-6}$ alkyl, —$OR^{13}$, —E—$N(R^{14})$ $R^{15}$ or, together with $R^3$, represents =O;

$R^3$ represents H, $C_{1-6}$ alkyl or, together with $R^2$, represents =O;

$R^{13}$ represents H, $C_{1-6}$ alkyl, —E-aryl, —E-$Het^6$, —$C(O)R^{16a}$, —$C(O)OR^{16b}$ or —$C(O)N(R^{17a})R^{17b}$;

$R^{14}$ represents H, $C_{1-6}$ alkyl, —E-aryl, —E-$Het^6$, —$C(O)R^{16a}$, —$C(O)OR^{16b}$, —$S(O)_2R^{16c}$, —$[C(O)]_pN(R^{17a})R^{17b}$ or —$C(NH)NH_2$;

$R^{15}$ represents H, $C_{1-6}$ alkyl, —E-aryl or —$C(O)R^{16d}$;

$R^{16a}$ to $R^{16d}$ independently represent, at each occurrence when used herein, $C_{1-6}$ alkyl which alkyl group is optionally substituted and/or terminated by one or more substituents selected from halo, aryl and $Het^7$, aryl, $Het^8$, or $R^{16a}$ and $R^{16d}$ independently represent H;

$R^{17a}$ and $R^{17b}$ independently represent, at each occurrence when used herein, H or $C_{1-6}$ alkyl which alkyl group is optionally substituted and/or terminated by one or more substituents selected from halo, aryl and $Het^9$, aryl, $Het^{10}$, or together represent $C_{3-6}$ alkylene, optionally interrupted by an O atom;

E represents, at each occurrence when used herein, a direct bond or $C_{1-4}$ alkylene;

p represents 1 or 2;

$Het^1$ to $Het^{10}$ independently represent five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, —$N(R^{18a})R^{18b}$, —$C(O)R^{18c}$, —$C(O)OR^{18d}$, —$C(O)N(R^{18e})R^{18f}$, —$N(R^{18g})C(O)R^{18h}$ and —$N(R^{18i})S(O)_2R^{18j}$;

$R^{18a}$ to $R^{18j}$ independently represent $C_{1-6}$ alkyl, aryl or $R^{18a}$ to $R^{18j}$ independently represent H;

A represents a direct bond, —J—, —J—$N(R^{19})$—or —J—O—in which latter two groups, $N(R^{19})$—or O—is attached to the carbon atom bearing $R^2$ and $R^3$;

B represents —Z—, —Z—$N(R^{20})$—, —$N(R^{20})$—Z—, —Z—$S(O)_n$—, —Z—O— in which latter two groups, Z is attached to the carbon atom bearing $R^2$ and $R^3$, —$N(R^{20})C(O)O$—Z—in which latter group, —$N(R^{20})$ is attached to the carbon atom bearing $R^2$ and $R^3$, or —$C(O)N(R^{20})$—in which latter group, —C(O) is attached to the carbon atom bearing $R^2$ and $R^3$;

J represents $C_{1-6}$ alkylene optionally substituted by one or more substituents selected from —OH, halo and amino;

Z represents a direct bond or $C_{1-4}$ alkylene;

n represents 0, 1 or 2;

$R^{19}$ and $R^{20}$ independently represent H or $C_{1-6}$ alkyl;

G represents CH or N;

$R^4$ represents one or more optional substituents selected from —OH, cyano, halo, nitro, $C_{1-6}$ alkyl which alkyl group is optionally terminated by —$N(H)C(O)OR^{21a}$, $C_{1-6}$ alkoxy, —$N(R^{22a})R^{22b}$, —$C(O)R^{22c}$, —$C(O)OR^{22d}$, —$C(O)N(R^{22e})R^{22f}$, —$N(R^{22g})C(O)R^{22h}$, —$N(R^{22i})C(O)N(R^{22j})R^{22k}$, —$N(R^{22m})S(O)_2R^{21b}$, —$S(O)_2R^{21c}$, and/or —$OS(O)_2R^{21d}$;

$R^{21a}$ to $R^{21d}$ independently represent $C_{1-6}$ alkyl;

$R^{22a}$ and $R^{22b}$ independently represent H, $C_{1-6}$ alkyl or together represent $C_{3-6}$ alkylene, resulting in a four- to seven-membered nitrogen-containing ring;

$R^{22c}$ or $R^{22m}$ independently represent H or $C_{1-6}$ alkyl; and $R^{41}$ to $R^{46}$ independently represent H or $C_{1-3}$ alkyl;

wherein each aryl and aryloxy group, unless otherwise specified, is optionally substituted; or a pharmaceutically acceptable derivative thereof, which process comprises:

(a) reaction of a compound of formula II,

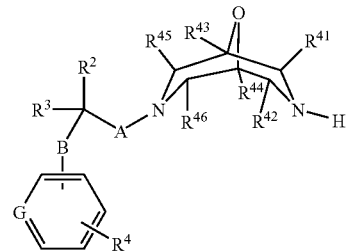

II

wherein $R^2$, $R^3$, $R^4$, $R^{41}$ to $R^{46}$, A, B and G are as defined above, with a compound of formula III, $R^1$—$L^1$    III wherein $L^1$ represents a leaving group and $R^1$ and $R^7$ are as defined above;

(b) for compounds of formula I in which $R^1$ represents —$C(O)XR^7$ or —$C(O)N(R^8)R^{5d}$, reaction of a compound of formula IV,

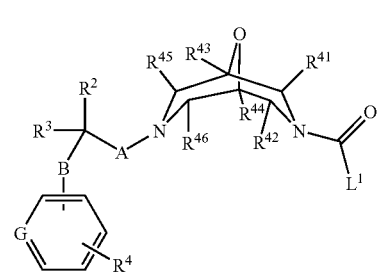

IV

wherein $R^2$, $R^3$, $R^4$, $R^{41}$ to $R^{46}$, A, B and G are as defined above and $L^1$ is as defined above, with a compound of formula V, $R^{24}$—H    V wherein $R^{24}$ represents —$XR^7$ or —$N(R^8)R^{5d}$ and $R^{5d}$, $R^7$, $R^8$ and X are as defined above;

(c) for compounds in which $R^1$ represents —C(O)N(H)$R^8$, reaction of a compound of formula II, as defined above, with a compound of formula VI,

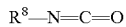

$R^8$—N=C=O    VI wherein $R^8$ is as defined above;

(d) reaction of a compound of formula VII,

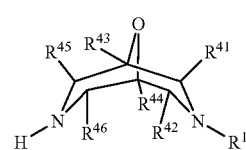

VII wherein $R^1$ and $R^{41}$ to $H^{46}$ are as defined above, with a compound of formula VIII,

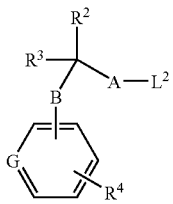

VIII wherein $L^2$ represents a leaving group and $H^2$, $H^3$, $R^4$, A, B and G are as defined above;

(e) for compounds of formula I in which A represents $CH_2$ and $R^2$ represents —OH or —N(H)$R^{14}$, reaction of a compound of formula VII, as defined above, with a compound of formula IX,

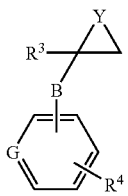

IX wherein Y represents O or N($R^{14}$) and $R^3$, $R^4$, $R^{14}$, B and G are as defined above;

(f) for compounds of formula I in which B represents —Z—O—, reaction of a compound of formula X,

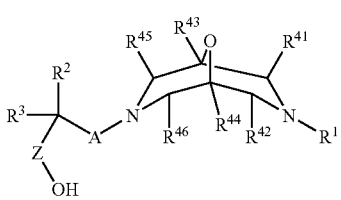

X wherein $R^1$, $R^2$, $R^3$, $R^{41}$ to $R^{46}$, A and Z are as defined above, with a compound of formula XI,

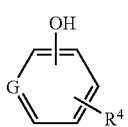

XI wherein $R^4$ and G are as defined above;

(g) for compounds of formula I in which G represents N and B represents —Z—O—, reaction of a compound of formula X, as defined above, with a compound of formula XII,

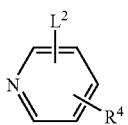

XII wherein $R^4$ is as defined above and $L^2$ is as defined above;

(h) for compounds of formula I in which $R^2$ represents —O$R^{13}$, in which $R^{13}$ represents $C_{1-6}$ alkyl, —E-aryl or —E-Het$^6$, reaction of a compound of formula I in which $R^2$ represents OH with a compound of formula XIII, $R^{13a}OH$  XIII wherein $R^{13a}$ represents $C_{1-6}$ alkyl, —E-aryl or E-Het$^6$, and E and Het$^6$ are as defined above;

(i) for compounds of formula I in which $R^2$ represents —O$R^{13}$, in which $R^{13}$ represents $C_{1-6}$ alkyl, —E-aryl or —E-Het$^6$, reaction of a compound of formula XIV,

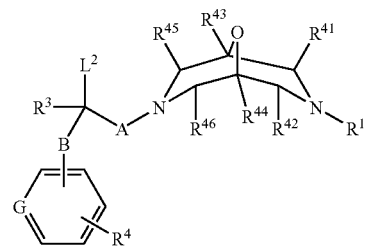

XIV wherein $R^1$, $R^3$, $R^4$, $R^{41}$ to $R^{46}$, A, B and G are as defined above and $L^2$ is as defined above, with a compound of formula XIII, as defined above;

(j) for compounds of formula I in which $R^2$ represents —E—$NH_2$, reduction of a compound of formula XV,

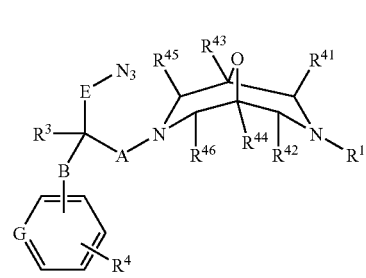

XV wherein $R^1$, $R^3$, $R^4$, $R^{41}$ to $R^{46}$, A, B, E and G are as defined above;

(k) for compounds of formula I in which $R^2$ represents —E—N($R^{14}$)$R^{15}$, wherein $R^{14}$ represents $C_{1-6}$ alkyl, —E-aryl, —E-Het$^6$, —C(O)$R^{16a}$, —C(O)O$R^{16b}$, —S(O)$_2R^{16c}$ or —C(O)N($R^{17a}$)$R^{17b}$, reaction of a compound of formula I in which $R^2$ represents E—N(H)$R^{15}$ with a compound of formula XVI, $R^{14a}$—$L^1$  XVI wherein $R^{14a}$ represents $C_{1-6}$ alkyl, —E-aryl, —E-Het$^6$, —C(O)$R^{16a}$, —C(O)O$R^{16b}$b, —S(O)$_2R^{16c}$ or —C(O)N($R^{17a}$)$R^{17b}$, and $R^{16a}$, $R^{16b}$, $R^{16c}$, $R^{17a}$, $R^{17b}$, Het$^6$ and E are as defined above and $L^1$ is as defined above;

(l) for compounds of formula I in which $R^2$ represents —E—N($R^{15}$)C(O)N(H)$R^{17a}$, reaction of a compound of formula I in which $R^2$ represents —E—N(H)$R^{15}$ with a compound of formula XVII, $R^{17a}$—N=C=O  XVII wherein $R^{17a}$ is as defined above;

(m) for compounds of formula I in which $R^2$ represents —E—N(H)[C(O)]$_2$NH$_2$, reaction of a compound of formula I in which $R^2$ represents —E—NH$_2$ with oxalic acid diamide;

(n) for compounds of formula I in which $R^2$ represents —E—N(H)C(NH)NH$_2$, reaction of a compound of formula I in which $R^2$ represents —E—NH$_2$ with a compound of formula XVIII,

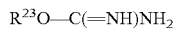  XVIII or an N-protected derivative thereof, wherein $R^{23}$ is as defined above;

(o) for compounds of formula I in which $R^2$ represents —OR$^{13}$, in which $R^{13}$ represents —C(O)R$^{16a}$, —C(O)OR$^{16b}$ or —C(O)N(R$^{17a}$)R$^{17b}$, reaction of a compound of formula I in which $R^2$ represents —OH with a compound of formula XIX,

  XIX wherein $R^{13b}$ represents —C(O)R$^{16a}$, —C(O)OR$^{16b}$ or —C(O)N(R$^{17a}$)R$^{17b}$, $L^3$ represents a leaving group and $R^{16a}$, $R^{16b}$, $R^{17a}$ and $R^{17b}$ are as defined above;

(p) for compounds of formula I in which $R^2$ represents H or —OH and $R^3$ represents H, reduction of a compound of formula I in which $R^2$ and $R^3$ together represent =O;

(q) for compounds of formula I in which $R^2$ represents halo, substitution of a corresponding compound of formula I in which $R^2$ represents —OH, using an appropriate halogenating agent;

(r) for compounds of formula I in which $R^2$ and $R^3$ represent H, A represents —J— and B represents —N(R$^{20}$)—Z— (wherein —N(R$^{20}$) is attached to the carbon atom bearing $R^2$ and $R^3$), reaction of a compound of formula XX,

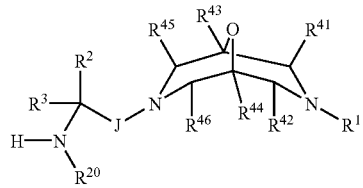  XX wherein $R^1$, $R^2$, $R^3$, $R^{20}$, $R^{41}$ to $R^{46}$ and J are as defined above, with a compound of formula XXI,

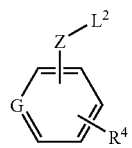  XXI wherein $R^4$, G and Z are as defined above and $L^2$ is as defined above;

(s) for compounds of formula I in which A represents C$_2$ alkylene and $R^2$ and $R^3$ together represent =O, reaction of a compound of formula VII, as defined above, with a compound of formula XXII,

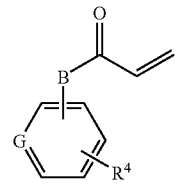  XXII wherein B, G and $R^4$ are as defined above;

(t) for compounds of formula I in which $R^1$ represents —C(O)XR$^7$, —C(O)N(R$^8$)R$^{5d}$ or —S(O)$_2$R$^9$, reaction of a compound of formula XXIII,

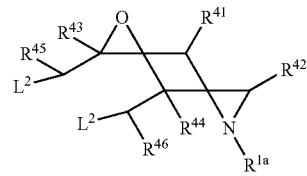  XXIII wherein $R^{1a}$ represents —C(O)XR$^7$, —C(O)N(R$^8$)R$^{5d}$ or —S(O)$_2$R$^9$ and $R^{5d}$, $R^7$, $R^8$, $R^9$ and $R^{41}$ to $R^{46}$ are as defined above and $L^2$ is as defined above, with a compound of formula XXIV,

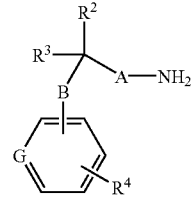  XXIV wherein $R^2$, $R^3$, $R^4$, A, B and G are as defined above;

(u) for compounds of formula I which are oxabispidine-nitrogen N-oxide derivatives, oxidation of the corresponding oxabispidine nitrogen of a corresponding compound of formula I; or (v) for compounds of formula I which are C$_{1-4}$ alkyl quaternary ammonium salt derivatives, in which the alkyl group is attached to a oxabispidine nitrogen, reaction, at the oxabispidine nitrogen, of a corresponding compound of formula I with a compound of formula XXV,

  XXV wherein $R^{25}$ represents C$_{1-4}$ alkyl and $L^4$ is a leaving group.

* * * * *